(12) United States Patent
Tveita

(10) Patent No.: US 11,186,641 B2
(45) Date of Patent: Nov. 30, 2021

(54) FUSION PROTEINS TARGETING TUMOUR ASSOCIATED MACROPHAGES FOR TREATING CANCER

(71) Applicant: OSLO UNIVERSITETSSYKEHUS HF, Oslo (NO)

(72) Inventor: Anders Tveita, Oslo (NO)

(73) Assignee: OSLO UNIVERSITETSSYKEHUS HF, Oslo (NO)

(*) Notice: Subject to any disclaimer, the term of this patent is extended or adjusted under 35 U.S.C. 154(b) by 215 days.

(21) Appl. No.: 16/085,126

(22) PCT Filed: Mar. 16, 2017

(86) PCT No.: PCT/IB2017/000388
§ 371 (c)(1),
(2) Date: Sep. 14, 2018

(87) PCT Pub. No.: WO2017/158436
PCT Pub. Date: Sep. 21, 2017

(65) Prior Publication Data
US 2019/0023795 A1    Jan. 24, 2019

Related U.S. Application Data

(60) Provisional application No. 62/309,704, filed on Mar. 17, 2016.

(51) Int. Cl.
| | | |
|---|---|---|
| C07K 16/28 | (2006.01) | |
| C07K 14/715 | (2006.01) | |
| C07K 16/40 | (2006.01) | |
| C12N 15/62 | (2006.01) | |
| A61P 35/00 | (2006.01) | |
| A61K 38/20 | (2006.01) | |
| A61K 39/00 | (2006.01) | |
| A61K 38/00 | (2006.01) | |

(52) U.S. Cl.
CPC .......... C07K 16/2851 (2013.01); A61K 38/20 (2013.01); A61P 35/00 (2018.01); C07K 14/7155 (2013.01); C07K 16/28 (2013.01); C07K 16/2896 (2013.01); C07K 16/40 (2013.01); C12N 15/62 (2013.01); A61K 38/00 (2013.01); A61K 2039/505 (2013.01); A61K 2039/572 (2013.01); C07K 2317/22 (2013.01); C07K 2317/569 (2013.01); C07K 2319/00 (2013.01)

(58) Field of Classification Search
CPC .... C07K 16/28; C07K 16/2896; C07K 16/40; C07K 2319/00; A61P 35/00; A61K 38/20; A61K 2039/505
See application file for complete search history.

(56) References Cited

U.S. PATENT DOCUMENTS

| | | | | |
|---|---|---|---|---|
| 2011/0262348 | A1* | 10/2011 | Movahedi | A61K 47/6899 424/1.49 |
| 2012/0301394 | A1* | 11/2012 | Movahedi | B82Y 5/00 424/1.49 |
| 2013/0101608 | A1* | 4/2013 | Satijn | A61P 35/00 424/178.1 |
| 2016/0175459 | A1* | 6/2016 | Gey | C07K 16/2818 424/85.2 |

FOREIGN PATENT DOCUMENTS

| | | |
|---|---|---|
| EP | 2687231 | 1/2014 |
| WO | 2013/174537 | 11/2013 |
| WO | 2014/170032 | 10/2014 |
| WO | WO2016018528 | * 2/2015 |
| WO | 2015/103928 | 7/2015 |
| WO | 2017/003044 | 1/2017 |

OTHER PUBLICATIONS

International Search Report and Written Opinion, International Patent Application No. PCT/IB2017/000388, dated Jun. 14, 2017.
Cieslewicz et al. "Targeted delivery of proapoptotic peptides to tumor-associated macrophages improved survival" Proceedings National Academy of Sciences PNAS, vol. 110, No. 40, Sep. 17, 2013, pp. 15919-15924.
Zhang, X. et al. "Hydrazinocurcumin Encapsuled Nanoparticles "Re-Educate" Tumor-Associated Macrophages . . . " PLOS One, vol. 8, No. 6, Jun. 25, 2013, p. e65896.
Meng Xu et al. "Intratumoral Delivery of IL-21 Overcomes Anti-Her2/Neu Resistance through Shifting Tumor-Associated Macrophages from M2 to M1 Phenotype" The Journal of Immunology, vol. 194, No. 10, May 15, 2015, pp. 4997-5006.
Alberto Mantovani et al. "Tumour-associated macrophages as treatment targets in oncology" Nature Reviews Clinical Oncology, Jan. 24, 2017, pp. 1-18.

* cited by examiner

*Primary Examiner* — Lei Yao
(74) *Attorney, Agent, or Firm* — Casimir Jones, S.C.; J. Mitchell Jones

(57) ABSTRACT

The present invention relates to cancer immunotherapy. In particular, provided herein are fusion proteins for targeting tumor associated macrophages with immunostimulatory agents.

2 Claims, 12 Drawing Sheets

Specification includes a Sequence Listing.

FIG. 1A
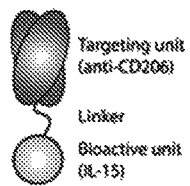
FIG. 1B
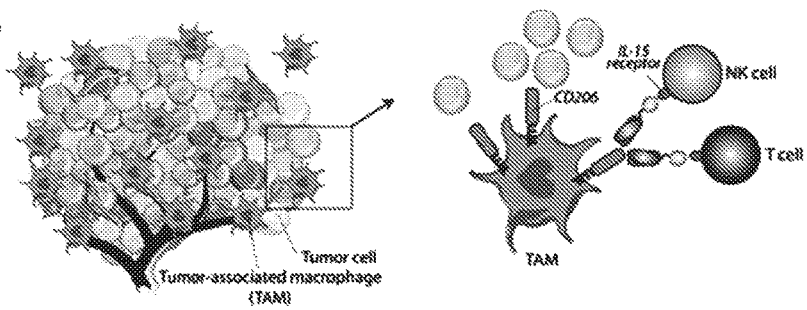
FIG. 2A
FIG. 2B
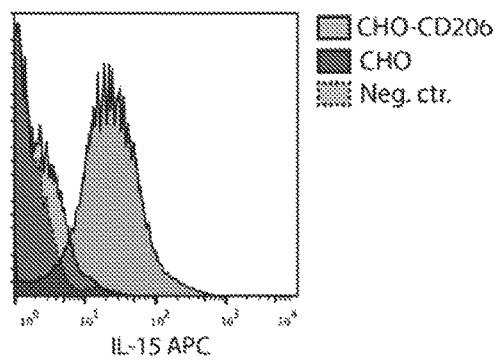
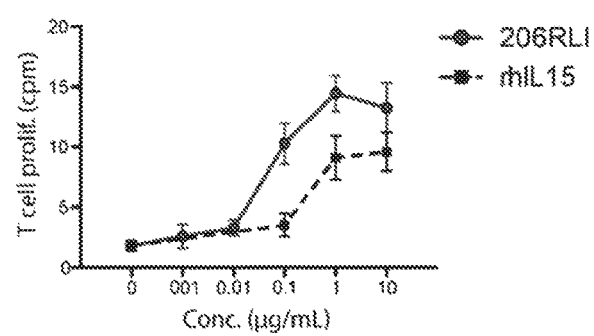

FIG. 11A
FIG. 11B
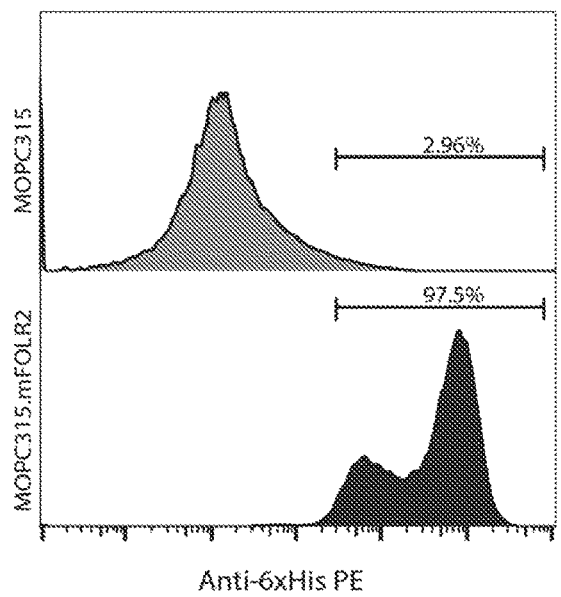
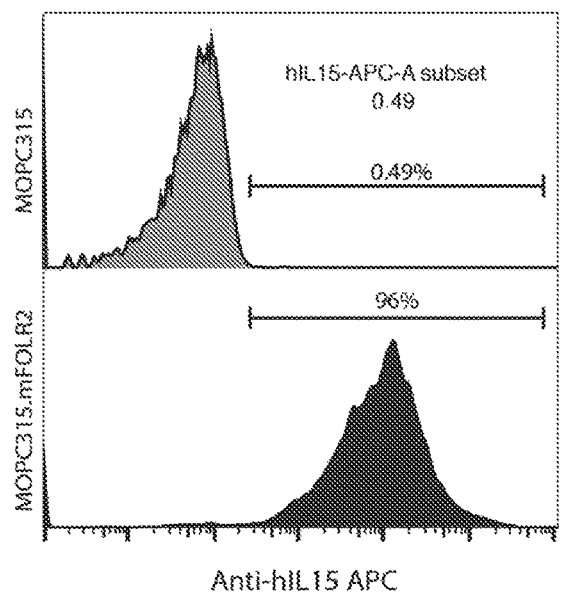

FUSION PROTEINS TARGETING TUMOUR ASSOCIATED MACROPHAGES FOR TREATING CANCER

CROSS REFERENCE TO RELATED APPLICATIONS

This application is a Section 371 U.S. national stage entry of International Patent Application No. PCT/IB2017/000388, International Filing Date Mar. 16, 2017, which claims the benefit of U.S. Provisional Application Ser. No. 62/309,704, filed Mar. 17, 2016, which are incorporated herein by reference in their entireties.

SEQUENCE LISTING

The text of the computer readable sequence listing filed herewith, titled "34589-252_ST25", created Mar. 9, 2021, having a file size of 188,000 bytes, is hereby incorporated by reference in its entirety.

FIELD OF THE INVENTION

The present invention relates to cancer immunotherapy. In particular, provided herein are fusion proteins for targeting tumor associated macrophages with immunostimulatory agents.

BACKGROUND OF THE INVENTION

Despite advances in our understanding and management of cancer, the majority of cancer patients will still die of the disease. For many patient groups, prognosis is dire, with few or no available curative treatment regimens. Furthermore, resistance development and disease relapse is commonplace. There is therefore an unmet need for the development of novel therapeutics founded on fundamentally different mechanisms of action.

The ability of the immune system to fight cancer has been clearly demonstrated in recent years, highlighted by the massive clinical and commercial success of the immune checkpoint inhibitors. One of the key advantages offered by these drugs is that they have the potential to treat several cancer types and are supplied in an off-the-shelf manner. In contrast to personalized immunotherapies such as adoptive T-cell therapy or dendritic cell (DC) vaccines, they do not rely on customization for each patient. On the downside, only 10-30% of patients respond adequately, and checkpoint inhibitors have a challenging safety profile.

Tumor Associated Macrophages (TAMs) represent up to 50% of the tumor mass. TAMs constitute an extremely heterogeneous population; they originate from blood monocytes, which differentiate into distinct macrophage types, schematically identified as M1 (or classically activated) and M2 (or alternatively activated). It is now generally accepted that TAM have an M2 phenotype and show mostly pro-tumoral functions, promoting tumor cell survival, proliferation, and dissemination. High levels of TAM are often, although not always, correlated with a bad prognosis, and recent studies have also highlighted a link between their abundance and the process of metastasis. This pathological evidence has been confirmed also at gene level, where molecular signatures associated with poor prognosis in lymphomas and breast carcinomas include genes characteristic of macrophages.

What is needed in the art are additional agents and methods that can be used to treat many different types of cancer and tumors.

SUMMARY OF THE INVENTION

The present invention relates to cancer immunotherapy. In particular, provided herein are fusion proteins for targeting tumor associated macrophages with immunostimulatory agents.

For example, in some embodiments, the present invention provides a fusion protein, comprising an immunostimulatory agent (e.g., IL15 polypeptide or fragment thereof) fused to a targeting unit that targets the immunostimulatory agent to a tumor associated macrophage. In some embodiments, the targeting unit binds to CD206. In some embodiments, targeting unit is an immunoglobulin or fragment thereof that specifically binds to CD206. In some embodiments, the immunoglobulin is a single domain antibody (sdAb) or a single chain variable fragments (scFv), although other antibodies or antibody fragments are specifically contemplated. In some embodiments, the immunostimulatory agent is the sushi domain of IL15 receptor alpha (IL15ra-sushi). In some embodiments, a CD206 specific sdAb is fused to the IL15ra-sushi via a linker to serve as the therapeutic molecule 206RLI. The present invention is not limited to particular immunostimulatory agents. Examples include, but are not limited to, cytokines (e.g., interferon alpha, interferon gamma, interleukin-21, interleukin-17, interleukin-18, interleukin-27, TNF-α, interleukin 2, interleukin 7, interleukin 12); costimulatory ligands (e.g., 41bb, CD80, CD86); and antibody fragments with agonistic or antagonistic activity against immune checkpoints (e.g., anti-PD1, anti-CTLA4, etc). The present invention is not limited to particular targeting units or targets. Examples include, but are not limited to, mannose receptor (CD206), folate receptor beta (FOLR2) and leugmain (LGMN).

Accordingly, in some embodiments, the targeting unit binds to a protein selected from the group consisting CD206, FOLR2, LGMN, CD204, CD163, and CD301. In some embodiments, the targeting unit is an antigen binding protein that specifically binds to the CD206. In some embodiments, the antigen binding protein is selected from the group consisting of an immunoglobulin single variable domain and a single chain variable fragment (scFv). In some embodiments, the immunoglobulin single variable domain is a nanobody. In some embodiments, the nanobody binds to CD206. In some embodiments, the nanobody is selected from the group consisting of nanobodies having an amino acid sequence selected from the group consisting of SEQ ID NOs: SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, 108, and 112 and nanobodies that have at least 80% identity to the sequences. In some embodiments, the nanobody has a CDR1, CDR2 and/or CDR3 or a variant thereof from the list of CDRs for nanobodies that bind CD206 in Table 1. In some embodiments, the immunoglobulin single variable domain binds to FOLR2. In some embodiments, the immunoglobulin single variable domain has an amino acid sequence selected from the group consisting of SEQ ID NO: 122 and single domain antibody fragments that have at least 80% identity to the sequence. In some embodiments, the nanobody has a CDR1, CDR2 and/or CDR3 or a variant thereof from the list of CDRs for nanobodies that bind FOLR2 in Table 1.

In some embodiments, the immunostimulatory agent is selected from the group consisting of an interleukin, an interferon and a tumor necrosis factor. In some embodiments, the interleukin is selected from the group consisting of IL-1β, IL-2, IL-7, IL-8, IL-12, IL-15, IL-17, IL-18, IL-21, IL-23, IL-27 and IL-33. In some embodiments, the interleukin is selected from the group consisting of an IL15 polypeptide, IL15 alpha receptor or fragment or fusion thereof. In some embodiments, the interferon is selected from the group consisting of IL-1β, IL-2, IL-7, IL-8, IL-12, IL-15, IL-17, IL-18, IL-21, IL-23, IL-27 and IL-33. In some embodiments, the tumor necrosis factor is selected from the group consisting of CD40L, EDA, FASL, LTA, LTB, RANKL, OX40L, TNF, TNFSF7, TNFSF8, TNFSF9, TNFSF12, TNFSF13, TNFSF13B, F18, TRAIL, BAFF, 4-1BBL, and 4-1BB.

In some embodiments, the targeting unit and the immunostimulatory agent are connected by a linker. In some embodiments, the linker has an amino acid sequence selected from the group consisting of SEQ ID NO:109, SEQ ID NO:110 and SEQ ID NO:147.

In some embodiments, the fusion protein has an amino acid sequence encoded by a nucleic acid sequence selected from the group consisting of SEQ ID NOs:1, 138-146 and 153-170 and sequences having at least 80% identity to the amino acid sequences.

Further embodiments provide a nucleic acid encoding the fusion protein and vectors comprising the nucleic acid.

Still further embodiments provide a pharmaceutical composition comprising the fusion protein described herein. In some embodiments, the pharmaceutical composition further comprise at least one of a pharmaceutically acceptable carrier, adjuvant, or diluent.

In some embodiments, the present invention provides antigen binding proteins comprising a CDR1, CDR2 and/or CDR3 and CDRs having at least 80% identity to the CDR1, CDR2, and/or CDR3 from an immunoglobulin single variable domain amino acid sequence that binds to CD206 or FOLR2 as identified in Table 1. In some embodiments, the antigen binding protein binds to CD206. In some embodiments, the antigen binding protein binds to FOLR2.

In some embodiments, the antigen binding protein is selected from the group consisting of an immunoglobulin or fragment thereof, a humanized immunoglobulin or fragment thereof, a single chain antibody (scFV), and an immunoglobulin single variable domain. In some embodiments, the antigen binding protein is an immunoglobulin single variable domain. In some embodiments, the immunoglobulin single variable domain is derived from a camelid antibody. In some embodiments, the immunoglobulin single variable domain comprises a nanobody sequence ($V_HH$).

In some embodiments, the immunoglobulin single variable domain has an amino acid sequence selected from the group consisting of SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, and 108 and sequences having at least 80% identity to the sequences. In some embodiments, the immunoglobulin single variable domain comprises an amino acid sequence that comprises 4 framework regions (FR) and 3 complementarity determining regions (CDR) according to the following formula (1): FR1-CDR1-FR2-CDR2-FR3-CDR3-FR4 (1); or any suitable fragment thereof.

In some embodiments, the antigen binding protein is fused to a moiety selected from the group consisting of an immunostimulatory agent, a toxin, a cytotoxic drug, an enzyme capable of converting a prodrug into a cytotoxic drug, a radionuclide, a cytotoxic cell; and wherein the domain is fused to the moiety directly or through a linker. In some embodiments, the antigen binding protein is fused, either directly or through a linker, to a detectable label.

In some embodiments, the present invention provides a nucleic acid encoding the antigen binding protein or fusion as described above. In some embodiments, the present invention provides a vector comprising the described nucleic acid sequences. In some embodiments, the present invention provides a pharmaceutical composition comprising the antigen binding protein or fusion as described above. In some embodiments, the pharmaceutical compositions further comprise at least one of a pharmaceutically acceptable carrier, adjuvant, or diluent.

Additional embodiments provide a methods of inducing a cancer specific immune response, comprising: administering a fusion protein as described herein to a subject diagnosed with cancer under conditions such that the subject generates or amplifies a pre-existing immune response to cancer cells in the subject. In some embodiments, the cancer is, for example, lung cancer, breast cancer, pancreatic cancer, prostate cancer, melanoma or multiple myeloma. In some embodiments, the immune response kills the cancer cells. In some embodiments, the immune response results in tumor regression.

Yet other embodiments provide a method of treating cancer, comprising: administering a fusion protein as described herein to a subject diagnosed with cancer under conditions such that the cancer is reduced or eliminated. In some embodiments, the subject generates an immune response to the cancer. In some embodiments, the conditions such that the cancer is reduced or eliminated comprise regression of a tumor. In some embodiments, the cancer is selected from the group consisting of lung cancer, breast cancer, pancreatic cancer, prostate cancer, melanoma and multiple myeloma.

Still further embodiments provide the use of the fusion proteins described herein to generate a cancer specific immune response in a subject. In some embodiments, the cancer is, for example, lung cancer, breast cancer, pancreatic cancer, prostate cancer, melanoma or multiple myeloma. In some embodiments, the immune response kills the cancer cells. In some embodiments, the immune response results in tumor regression.

In some embodiments, the present invention provides the use of the fusion proteins described herein to treat cancer in a subject. In some embodiments, the subject generates an immune response to the cancer. In some embodiments, the conditions such that the cancer is reduced or eliminated comprise regression of a tumor. In some embodiments, the cancer is selected from the group consisting of lung cancer, breast cancer, pancreatic cancer, prostate cancer, melanoma and multiple myeloma.

Additional embodiments are described herein.

DESCRIPTION OF THE DRAWINGS

FIG. 1. Schematic overview of exemplary fusion proteins. FIG. 1A. An engineered protein comprising a targeting unit (an antibody fragment) connected to an immunostimulatory cytokine (interleukin 15; IL15) through a flexible linker. FIG. 1B. Schematic overview of a typical tumor, where cancer cells are embedded in a network of supporting cells and blood vessels. The targeting unit of the protein binds to a surface structure (CD206) that is expressed on a class of cells; tumor-associated macrophages (TAMs), which are abundantly present within tumors in most types of human cancer. Administration of the fusion protein results in specific binding to the cell surface of these cells. This leads to accumulation of IL15 within the tumor, which serves to activate tumor-infiltrating immune cells (T-cells and NK cells) to kill cancer cells.

FIG. 2A. An SDS-PAGE gel showing crude 206RLI product of the expected size (38 kDa) produced by this approach is shown in the right.

FIG. 2B. Flow cytometry verification of binding of the purified 206RLI compound to cells engineered to express human CD206 (blue), showing negligible binding to control cells (red). C. T cell proliferation assay showing the ability of purified 206RLI to stimulate growth of human CD4+ T cells isolated from blood of healthy donors. Of note, biological activity is found to be superior to that of recombinant interleukin 15 (rhIL15)

FIG. 11. Results of flow cytometry showing binding of the CL10scFv-IL15RLI fusion protein to mFOLR2-expressing NS0 cells.

DEFINITIONS

Figure 3A:
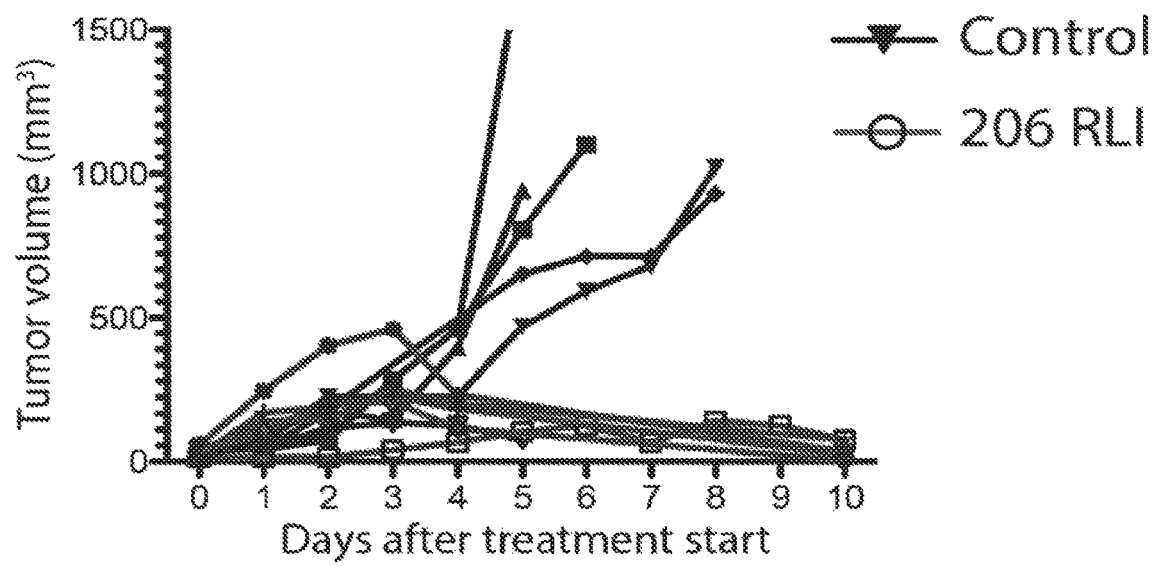
FIG. 3A. 206RLI treatment leads to the formation of a central necrotic ulceration within the tumors within a few days, and a rapid and dramatic shrinkage of tumors.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and/or molecular screening tests.

As used herein, the term "initial diagnosis" refers to a test result of initial cancer diagnosis that reveals the presence or absence of cancerous cells (e.g., using a biopsy and histology).

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

Staging of cancer can also be based on the revised criteria of TNM staging by the American Joint Committee for Cancer (AJCC) published in 1988. Staging is the process of describing the extent to which cancer has spread from the site of its origin. It is used to assess a patient's prognosis and to determine the choice of therapy. The stage of a cancer is determined by the size and location in the body of the primary tumor, and whether it has spread to other areas of the body. Staging involves using the letters T, N and M to assess tumors by the size of the primary tumor (T); the degree to which regional lymph nodes (N) are involved; and the absence or presence of distant metastases (M)—cancer that has spread from the original (primary) tumor to distant organs or distant lymph nodes. Each of these categories is further classified with a number 1 through 4 to give the total stage. Once the T, N and M are determined, a "stage" of I, II, III or IV is assigned. Stage I cancers are small, localized and usually curable. Stage II and III cancers typically are locally advanced and/or have spread to local lymph nodes. Stage IV cancers usually are metastatic (have spread to distant parts of the body) and generally are considered inoperable.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

As used herein, the term "co-administration" refers to the administration of at least two agent(s) (e.g., a composition described herein and a chemotherapeutic agent) or therapies to a subject. In some embodiments, the co-administration of two or more agents/therapies is concurrent. In other embodiments, a first agent/therapy is administered prior to a second agent/therapy. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "antigen binding agent (e.g., "antigen-binding protein" or protein mimetic such as an apatamer) refers to proteins that bind to a specific antigen. "Antigen-binding proteins" include, but are not limited to, immunoglobulins, including polyclonal, monoclonal, chimeric, single chain, single domain, and humanized antibodies, Fab fragments, F(ab')2 fragments, and Fab expression libraries. Various procedures known in the art are used for the production of polyclonal antibodies. For the production of antibody, various host animals can be immunized by injection with the peptide or protein containing the desired epitope including but not limited to rabbits, mice, rats, sheep, goats, llamas, alpacas, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, Gerbu adjuvant and potentially useful human adjuvants such as BCG (Bacille Calmette-Guerin) and *Corynebacterium parvum*.

As used herein, the term "Tumor Associated Macrophage" or "TAM" refers to cells of macrophage lineage that are found in close proximity to or within tumor masses.

As used herein, the term "targeting unit that targets the immunostimulatory agent to a tumor associated macrophage" refers to a targeting unit (e.g., antigen binding protein) that specifically interacts with a tumor-associated macrophage (e.g., by specifically binding to a cell surface receptor or molecule on the surface of a tumor associated macrophage). In some embodiments, the targeting unit does not specifically bind to non-tumor associated macrophage or cells. In some embodiments, the targeting unit specifically binds to CD206.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

In some embodiments, monoclonal antibodies are generrated using the ABL-MYC method (See e.g., U.S. Pat. Nos. 5,705,150 and 5,244,656, each of which is herein incorporated by reference) (Neoclone, Madison, Wis.). ABL-MYC is a recombinant retrovirus that constitutively expresses v-abl and c-myc oncogenes. When used to infect antigen-activated splenocytes, this retroviral system rapidly induces antigen-specific plasmacytomas. ABL-MYC targets antigen-stimulated (Ag-stimulated) B-cells for transformation.

In some embodiments, biopanning as described in Pardon et al, Nat Protoc. 2014 March; 9(3):674-93 is used to generate single domain antibodies. In some embodiments, to generate murine scFv units, phage-based biopanning strategies, of which there are several published protocols available, are used.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, phage display biopanning, and immunoelectrophoresis assays, etc.) etc.

As used herein, the term "immunostimulatory agent" refers to any agent that stimulates an immune response. In some embodiments, the immune response is a cellular immune response (e.g., against a tumor associated macrophage). In some embodiments, the immunostimulatory agent is a cytokine (e.g., IL15 or a fragment thereof).

DETAILED DESCRIPTION OF THE INVENTION

The present invention relates to cancer immunotherapy. In particular, provided herein are fusion proteins for targeting tumor associated macrophages (TAMs, also known as tumor infiltrating macrophages) with immunostimulatory agents.

The ability of the immune system to fight cancer has been clearly demonstrated in recent years, highlighted by the massive clinical and commercial success of the immune checkpoint inhibitors. One of the key advantages offered by these drugs is that they have the potential to treat several cancer types and are supplied in an off-the-shelf manner. In contrast to personalized immunotherapies such as adoptive T-cell therapy or dendritic cell (DC) vaccines, they do not rely on customization for each patient. On the downside, only a minority of patients respond adequately, and checkpoint inhibitors have a challenging safety profile.

The present invention encompasses a new universal therapeutic concept that also targets a wide range of tumors and are supplied in an off-the-shelf manner, but which has a radically different mechanism of action. Whereas the checkpoint inhibitors require a pre-existing anti-tumor immune response in the patient, the present technology induces an in situ anti-tumor inflammatory focal immune response in the cancer tissue through targeted delivery of an immunostimulatory agent (e.g., as a non-limiting example, the highly pro-inflammatory cytokine IL15). Data presented herein shows complete eradication of large, established, tumors in mice within a few days without any signs of toxicity. See, e.g., example 2 and FIGS. 1-3.

Accordingly, provided herein are recombinant fusion proteins comprising of a targeting unit that binds to a protein displayed on or associated with TAMs linked to an immunostimulatory agent.

The fusion protein serves as a means of delivering an immunostimulatory agent directly to the tumor site with a high degree of specificity and selectivity, thereby locally activating the immune system to kill tumor cells. Since the targeted structure (e.g., as a non-limiting example, CD206) is not directly located on malignant cells, but on a cell type present in the majority of all tumors (e.g., the TAM), the compound is contemplated to be active against a wide variety of cancer types.

In contrast to conventional anti-cancer drugs, the fusion proteins of the present invention are not in themsleves toxic, but work by stimulating immune cells to infiltrate, activate and divide within the tumor. The side effects of the treatment are therefore very mild compared to cytotoxic agents, which inevitably cause damage to healthy tissue. Moreover, the drug may have less off-target effects than checkpoint inhibitors, which may cause severe autoimmune pathology and tissue destruction due to their systemic activity.

Developing tumors are dependent on recruiting non-malignant cells that provide support to the cancer cells such as nutrients and factors required for growth and expansion. Macrophages constitute a notable class of such supportive cells, and are abundantly present within tumors in most types of human cancer. In contrast to cancer cells, which are unique to each patient, tumor-infiltrating cells such as macrophages are structurally identical between individuals. In contrast to tumor cell antigens, surface structures on tumor-infiltrating macrophages are not subject to mutations and immunoediting.

Destruction of tumor-supportive cells such as TAMs has been attempted as a strategy to inhibit tumor growth. Such approaches may impair tumor progression, and in some cases have been shown to induce remission, but this type of treatment is not curative. Rather than depleting TAMs, the present invention utilizes them as a target to deliver molecules that induce localized immune responses within tumors.

The present invention provides novel fusion proteins that target TAMs with an immunostimulatory molecule. Accordingly, in some embodiments, the present invention provides fusion proteins that comprise a targeting unit in operable association with an immunostimulatory agent. In preferred embodiments, the targeting unit is an antigen binding protein that binds to a protein molecule displayed on or otherwise associated with TAMs. Thus, the targeting unit preferably binds to the TAM to bring the immunostimulatory agent into close proximity with the TAM. The present invention is not limited to any particular theory of operation, but it will be appreciated that by targeting the TAMs with an immunostimulatory agent, the immune system is triggered to provide a local response at the site of the tumor, resulting in regression and/or destruction of the tumor by the immune system. The present invention is not limited to the use of any particular targeting unit. In some preferred embodiments, the targeting unit is an antigen binding protein. Preferred antigen binding protein include, but are not limited to, nanobodies, single domain antibodies (sdAb), single chain antibodies (scFv), immunoglobulins and fragments thereof that bind to an antigen (e.g., Fab fragments). Likewise, the present invention is not limited to any particular immunostimulatory agents. Suitable immunostimulatory agents include, but are not limited to, interleukins, interferons, and tumor necrosis factors. In some preferred embodiments, the targeting unit and the immunostimulatory agent are operably associated through a linker. Suitable linker include, but are not limited to, llama IgG2 linkers and $(G_4S)_3$ linkers. Each of these components will be described in more detail below.

1. Targeting Units

As mentioned above, the present invention is not limited to the use of any particular targeting unit. In some preferred embodiments, the targeting unit is an antigen binding protein. Preferred antigen binding protein include, but are not limited to an immunoglobulins, a Fab, F(ab')$_2$, Fab' single chain antibody, Fv, single chain (scFv), mono-specific antibody, bi-specific antibody, tri-specific antibody, multivalent antibody, chimeric antibody, humanized antibody, human antibody, CDR-grafted antibody, shark antibody, an immunoglobulin single variable domain (e.g., a nanobody or a single variable domain antibody), camelid antibody (e.g., from the Camelidae family) microbody, intrabody (e.g., intracellular antibody), and/or de-fucosylated antibody and/or derivative thereof. Mimetics of binding agents and/or antibodies are also provided.

In some preferred embodiments, the targeting units are antigen binding proteins that specifically bind to CD206, FOLR2, LGMN, CD204, CD163, or CD301. When the targeting unit is an antigen binding protein, the antigen binding protein may be made identified and cloned as is known in the art and as described in more detail below. Recombinant DNA techniques may then be used to produce a construct encoding a fusion protein including the antigen binding protein in operable association with an immunostimulatory agent.

In some embodiments, the targeting unit is an immunoglobulin single variable domain. As used herein, an "immunoglobulin single variable domain" is an antigen-binding domain or fragment that comprises an amino acid sequence that comprises four framework regions (FR) and three complementarity determining regions (CDR) according to the following formula (1):

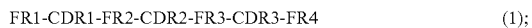

FR1-CDR1-FR2-CDR2-FR3-CDR3-FR4 (1);

or any suitable fragment thereof (which will then usually contain at least some of the amino acid residues that form at least one of the complementarity determining regions), and in which FR1 to FR4 refer to framework regions 1 to 4, respectively, and in which CDR1 to CDR3 refer to the complementarity determining regions 1 to 3, respectively.

Immunoglobulin single variable domains comprising 4 FRs and 3 CDRs are known to the person skilled in the art and have been described. See, e.g., Wesolowski J., V. Alzogaray, J. Reyelt, M. Unger, K. Juarez, M. Urrutia, A. Cauerhiff, W. Danquah, B. Rissiek, F. Scheuplin, N. Schwarz, S. Adriouch, O. Boyer, M. Seman, A. Licea, D. V. Serreze, F. A. Goldbaum, F. Haag, and F. Koch-Nolte. (2009). Single domain antibodies: promising experimental and therapeutic tools in infection and immunity Med. Microbiol. Immunol. 198, 157-174. Typical, but non-limiting, examples of immunoglobulin single variable domains include light chain variable domain sequences (e.g., a $V_L$ domain sequence), or heavy chain variable domain sequences (e.g., a $V_H$ domain sequence), which are usually derived from conventional four-chain antibodies. Preferably, the immunoglobulin single variable domains are derived from camelid antibodies, preferably from heavy chain camelid antibodies, devoid of light chains, and are known as $V_HH$ domain sequences or nanobodies (as described further herein).

In some embodiments, the targeting unit is a nanobody. A nanobody (Nb) is the smallest functional fragment or single variable domain ($V_HH$) of a naturally occurring single-chain antibody and is known to the person skilled in the art. They are derived from heavy chain only antibodies, seen in camelids. See, e.g., Hamers-Casterman C., Atarhouch T., Muyldermans S., Robinson G., Hamers C., Songa E., Bendahman N & Hamers R., 1993, Nature 363, p. 446-448; Desmyter A., T. Transue., M. Ghahroudi, M. Dao-Thi, F. Poortmans, R. Hamers, S. Muyldermans and L. Wyns, 1996, Nat. Struct. Biol., p. 803-811. In the family of "camelids" immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody or a $V_HH$ antibody. Nanobody™, Nanobodies™ and Nanoclone™ are trademarks of Ablynx NV (Belgium). The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies (as defined further herein) or attached to reporter molecules. Conrath K., M. Lauwereys, M. Galleni, A. Matagne, J-M. Frere, J. Kinne, L. Wyns, and S. Muyldermans (2001). beta-Lactamase Inhibitors Derived from Single-Domain Antibody Fragments Elicited in the Camelidae Antimicrob Agents. Chemother 45, 2807-2812. Nbs are stable, survive the gastro-intestinal system and can easily be manufactured. Therefore, Nbs can be used in many applications including drug discovery and therapy, but also as a versatile and valuable tool for purification, functional study and crystallization of proteins. See, e.g., Saerens D., G. Ghassabeh, S. Muyldermans, 2008, Current Opinion in Pharmacology 8, p. 600-608.

The nanobodies of the invention generally comprise a single amino acid chain that can be considered to comprise four "framework regions" or FRs and three "complementarity determining regions" or CDRs, according to formula (1) (as defined above). The term "complementarity determining region" or "CDR" refers to variable regions in nanobodies and contains the amino acid sequences capable of specifically binding to antigenic targets. These CDR regions account for the basic specificity of the nanobody for a particular antigenic determinant structure. Such regions are also referred to as "hypervariable regions." The nanobodies have three CDR regions, each non-contiguous with the others (termed CDR1, CDR2, CDR3). The delineation of the FR and CDR sequences is often based on the IMGT unique numbering system for V-domains and V-like domains. (See, e.g., Lefranc M. P., C. Pommie, et al. (2003). "IMGT unique numbering for immunoglobulin and T cell receptor variable domains and Ig superfamily V-like domains." Developmental and Comparative Immunology 27(1): 55-77.) Alternatively, the delineation of the FR and CDR sequences can be done by using the Kabat numbering system as applied to $V_HH$ domains from Camelids in the article of Riechmann and Muyldermans. (See, e.g., Riechmann and Muyldermans J. Immunol. Methods 2000; 240: 185-195.) As will be known by the person skilled in the art, the nanobodies can in particular be characterized by the presence of one or more Camelidae hallmark residues in one or more of the framework sequences (according to Kabat numbering), as described, for example, in WO 08/020,079, on page 75, Table A-3, incorporated herein by reference).

Non-limiting examples of nanobodies according to the present invention are as described herein and include anti-human, anti-mouse and cross-reactive anti-human/anti-mouse nanobodies. In some embodiments, the antibodies specifically bind to one of the following proteins on or in a Tumor Associated Macrophage (TAM): CD206 (macrophage mannose receptor (MMR); see, e.g., US Pat. Publ. 20120301394, incorporated herein by reference in its entirety), folate receptor beta (FOLR2), legumain (LGMN), CD204, CD163, or CD301. In a specific embodiment, the nanobodies of the present invention may comprise at least one of the complementarity determining regions (CDRs) derived from any of the nanobodies described herein. Preferably, the nanobodies of the present invention comprise a CDR1, a CDR2 and a CDR3 from one of the nanobodies described herein. More specifically, the nanobodies, or a functional fragment thereof, can be selected from the group comprising SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, 108, and 112 which bind to CD206 and SEQ ID NO: 122, which binds to FOLR2. The nanobodies identified by 58, 60, 62, 64, 66, 68, 70, 72, 74, 76, 78, 80, 82, 84, 86, 88, 90, 92, 94, 96, 98, 100, 102, 104, 106, 108, and 112 are codon and expression optimized. A "functional fragment" or a "suitable fragment," as used herein, may, for example, comprise one of the CDR loops. Preferably, the functional fragment comprises CDR3. More specifically, the nanobodies consist of any of SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, 108, and 112 which bind to CD206 and SEQ ID NO: 122, which binds to FOLR2. In still another embodiment, a nucleic acid sequence encoding any of the above nanobodies or functional fragments is also part of the present invention (for example, SEQ ID NOs:3, 57, 59, 61, 63, 65, 67, 69, 71, 73, 75, 77, 79, 81, 83, 85, 87, 89, 91, 93, 95, 97, 99, 101, 103, 105, 107 and 111, which encode nanobodies which bind to CD206 and SEQ ID NO:123 which encodes a single domain antibody (sdAM) or nanobody which binds to FOLR2). The nanobodies encoded by 57, 59, 61, 63, 65, 67, 69, 71, 73, 75, 77, 79, 81, 83, 85, 87, 89, 91, 93, 95, 97, 99, 101, 103, 105, 107 and 111 are expression and codon optimized. Further, the present invention also envisages expression vectors comprising nucleic acid sequences encoding any of the above nanobodies or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the nanobodies can be done according to techniques known by the skilled person in the art. For the sake of clarity, it is expected that at least some of the nanobodies identified herein may also be cross-reactive with macrophage mannose receptors of other mammalian species.

It will be understood that nanobodies may be identified with reference to the nucleotide and/or amino acid sequence corresponding to the variable and/or complementarity determining regions ("CDRs") thereof. For instance, an exemplary nanobody that is derived from, or is related to the nanobodies described above may comprise a variable domain. The variable domains typically comprise one or more CDRs that in large part determine the binding specificity of the nanobody. Nanobodies of the present invention may be identified by analysis of the nucleotide sequences encoding the CDRs or variable regions. The nanobodies of the present invention may also be identified by analysis of the amino acid sequences of (e.g., which may be encoded by the nucleotide sequences) of the CDRs or variable regions. Table 1 provides an identification of the CDRs of various nanobodies of the present invention which are listed in column 1 of the table. In some embodiments, the present invention provides nanobodies wherein one, two or all three of the CDRs of the nanobody have at least 60%, 70%, 80%, 90% or 100% identity to the CDRs identified for each nanobody. In other words, the present invention contemplates that variants of the listed CDRs are within the scope of the invention and that the CDRs may be altered by, for example, substitution, deletion, or addition mutations. It will also be recognized that the CDRs from the nanobodies that bind CD206 may be substituted for one another in a given nanobody variable domain. For example, a CDR1 from one of the nanobodies may be substituted with a CDR1 from another nanobody in Table 1, a CDR2 from one of the nanobodies may be substituted with a CDR2 from another nanobody in Table 1, and a CDR3 from one of the nanobodies may be substituted with a CDR3 from another nanobody in Table 1.

TABLE 1

| Nanobody Sequence identifier | CDR1 | CDR2 | CDR3 | Protein bound by Nanobody |
|---|---|---|---|---|
| SEQ ID NO: 30 | GSIFTIN SEQ ID NO: 171 | ITSGGSTN SEQ ID NO: 172 | VVVTTTPYSDY SEQ ID NO: 173 | CD206 |
| SEQ ID NO: 31 | ARIFSSY SEQ ID NO: 174 | VNGGSSST SEQ ID NO: 175 | AGRAGPLAASYRYDY SEQ ID NO: 176 | CD206 |
| SEQ ID NO: 32 | ARIFSSY SEQ ID NO: 174 | VNGGSSST SEQ ID NO: 175 | VVVTTTPYSDY SEQ ID NO: 173 | CD206 |
| SEQ ID NO: 33 | GSIFTIN SEQ ID NO: 171 | ITSGGSTN SEQ ID NO: 172 | AGRAGPLAASYRYDY SEQ ID NO: 176 | CD206 |
| SEQ ID NO: 34 | GSIFTIN SEQ ID NO: 171 | ITRGGSTN SEQ ID NO: 177 | VVVTTTPYSDY SEQ ID NO: 173 | CD206 |

TABLE 1-continued

| Nanobody Sequence identifier | CDR1 | CDR2 | CDR3 | Protein bound by Nanobody |
|---|---|---|---|---|
| SEQ ID NO: 35 | GSIFTIN SEQ ID NO: 171 | ITSGGSTN SEQ ID NO: 172 | VVVTTTAYSDY SEQ ID NO: 178 | CD206 |
| SEQ ID NO: 36 | GSIFTIN SEQ ID NO: 171 | ITSGGSTN SEQ ID NO: 172 | VVVTTTPYSDY SEQ ID NO: 173 | CD206 |
| SEQ ID NO: 37 | GSIFTIN SEQ ID NO: 171 | LTSGGSTN SEQ ID NO: 179 | VVVTTTPYADY SEQ ID NO: 180 | CD206 |
| SEQ ID NO: 38 | GSIFTIN SEQ ID NO: 171 | ITSGGSTN SEQ ID NO: 172 | VVVTTPYSDY SEQ ID NO: 181 | CD206 |
| SEQ ID NO: 39 | GSIFTIN SEQ ID NO: 171 | ITSGGSTN SEQ ID NO: 172 | VVVTTTPYSDY SEQ ID NO: 173 | CD206 |
| SEQ ID NO: 40 | GSIFTIN SEQ ID NO: 171 | VNGGSST SEQ ID NO: 175 | VVVTTTPYSDY SEQ ID NO: 173 | CD206 |
| SEQ ID NO: 41 | GSICTSN SEQ ID NO: 182 | ITSGGSTN SEQ ID NO: 172 | VVVTTTPYSDY SEQ ID NO: 173 | CD206 |
| SEQ ID NO: 42 | GLTFSIR SEQ ID NO: 183 | IMWSGGAT SEQ ID NO: 184 | VVVTTTPYSDY SEQ ID NO: 173 | CD206 |
| SEQ ID NO: 43 | WKHLHY SEQ ID NO: 185 | ITSGGSTN SEQ ID NO: 172 | VVVTTTPYSDY SEQ ID NO: 173 | CD206 |
| SEQ ID NO: 44 | GSIFTIN SEQ ID NO: 171 | ITSGGSTN SEQ ID NO: 172 | VVVTTTPYSDY SEQ ID NO: 173 | CD206 |
| SEQ ID NO: 45 | VSIFTIN SEQ ID NO: 186 | NTSGGSTN SEQ ID NO: 187 | VVVTTQYSDY SEQ ID NO: 194 | CD206 |
| SEQ ID NO: 46 | GSIFTIN SEQ ID NO: 171 | ITSGGSTN SEQ ID NO: 172 | VVVTTTPYSDY SEQ ID NO: 173 | CD206 |
| SEQ ID NO: 47 | ARIF S SY SEQ ID NO: 174 | ITSGGSTN SEQ ID NO: 172 | VVVTTTPYSDY SEQ ID NO: 173 | CD206 |
| SEQ ID NO: 48 | GSLFTIN SEQ ID NO: 188 | ITSGGSTN SEQ ID NO: 172 | LVVPPTPYSVY SEQ ID NO: 189 | CD206 |
| SEQ ID NO: 49 | GSIFTIN SEQ ID NO: 171 | ITSGGSTN SEQ ID NO: 172 | VVVTTTPYSDY SEQ ID NO: 173 | CD206 |
| SEQ ID NO: 50 | GSIFTIN SEQ ID NO: 171 | ITSGGSTN SEQ ID NO: 172 | VVVTTTPYSDY SEQ ID NO: 173 | CD206 |
| SEQ ID NO: 51 | GSIFTIN SEQ ID NO: 171 | STSGGSPN SEQ ID NO: 190 | GGGSSTPDSDY SEQ ID NO: 191 | CD206 |
| SEQ ID NO: 52 | GSIFTSN SEQ ID NO: 192 | ITSGGSTN SEQ ID NO: 172 | VVVTTTPYSDY SEQ ID NO: 173 | CD206 |
| SEQ ID NO: 53 | GSIFTIN SEQ ID NO: 171 | ITSGGSTN SEQ ID NO: 172 | VVVTTTPYSDY SEQ ID NO: 173 | CD206 |
| SEQ ID NO: 54 | GSIFTIN SEQ ID NO: 171 | ITSGGSTN SEQ ID NO: 172 | VVVTTTPEADY SEQID NO: 193 | CD206 |
| SEQ ID NO: 55 | GSIFTIN SEQ ID NO: 171 | ITSGGSTN SEQ ID NO: 172 | VVVTTTPYSDY SEQ ID NO: 173 | CD206 |
| SEQ ID NO: 56 | GSIFTIN SEQ ID NO: 171 | ITSGGSTN SEQ ID NO: 172 | VVVTTTPYSDY SEQ ID NO: 173 | CD206 |
| SEQ ID NO: 122 | GRTFSNY SEQ ID NO: 195 | ISQSGSITY SEQ ID NO: 196 | GNSFKSNDHWASTY SEQ ID NO: 197 | F OLR2 |

It should be noted that the term nanobody as used herein in its broadest sense is not limited to a specific biological source or to a specific method of preparation. For example, the nanobodies of the invention can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

One preferred class of nanobodies corresponds to the $V_HH$ domains of naturally occurring heavy chain antibodies directed against a macrophage mannose receptor, also known as CD206. As further described herein, such $V_HH$ sequences can generally be generated or obtained by suitably immunizing a species of Camelid with a MMR (i.e., so as to raise an immune response and/or heavy chain antibodies directed against a MMR), by obtaining a suitable biological sample from the Camelid (such as a blood sample, or any sample of B-cells), and by generating $V_HH$ sequences directed against a MMR, starting from the sample, using any suitable technique known per se. Such techniques will be clear to the skilled person. Alternatively, such naturally occurring $V_HH$ domains against MMR can be obtained from naive libraries of Camelid $V_HH$ sequences, for example, by screening such a library using MMR or at least one part, fragment, antigenic determinant or epitope thereof using one or more screening techniques known per se. Such libraries and techniques are, for example, described in WO9937681, WO0190190, WO03025020 and WO03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as, for example, described in WO0043507. Yet another technique for obtaining $V_HH$ sequences directed against a MMR involves suitably immunizing a transgenic mammal that is capable of expressing heavy chain antibodies (i.e., so as to raise an immune response and/or heavy chain antibodies directed against a MMR), obtaining a suitable biological sample from the transgenic mammal (such as a blood sample, or any sample of B-cells), and then generating $V_HH$ sequences directed against a MMR starting from the sample, using any suitable technique known per se. For example, for this purpose, the heavy chain antibody-expressing mice and the further methods and techniques described in WO02085945 and in WO04049794 can be used.

Accordingly, the invention encompasses methods of generating immunoglobulin single variable domains according to the invention. As a non-limiting example, a method is provided of generating nanobodies directed against or specifically binding to a protein displayed on or associated with a TAM (e.g., CD206, FOLR2, LGMN, CD204, CD163, or CD301, referred to collectively as TAM targeting protein) by immunization of an animal with the desired TAM targeting protein. For the immunization of an animal with the TAM targeting protein, the TAM targeting protein may be produced and purified using conventional methods that may employ expressing a recombinant form of the TAM targeting protein in a host cell, and purifying the TAM targeting protein using affinity chromatography and/or antibody-based methods. Any suitable animal, e.g., a warm-blooded animal, in particular a mammal such as a rabbit, mouse, rat, camel, sheep, cow, shark, or pig or a bird such as a chicken or turkey, may be immunized using any of the techniques well known in the art suitable for generating an immune response. The screening for nanobodies, as a non-limiting example, specifically binding to a TAM targeting protein may, for example, be performed by screening a set, collection or library of cells that express heavy chain antibodies on their surface (e.g., B-cells obtained from a suitably immunized Camelid), or bacteriophages that display a fusion of genIII and nanobody at their surface, by screening of a (naive or immune) library of $V_HH$ sequences or nanobody sequences, or by screening of a (naive or immune) library of nucleic acid sequences that encode VHH sequences or nanobody sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired antigen (in this case, the TAM targeting protein), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

A particularly preferred class of immunoglobulin single variable domains of the invention comprises nanobodies with an amino acid sequence that corresponds to the amino acid sequence of a naturally occurring $V_HH$ domain, but that has been "humanized," i.e., by replacing one or more amino acid residues in the amino acid sequence of the naturally occurring $V_HH$ sequence (and in particular in the framework sequences) by one or more of the amino acid residues that occur at the corresponding position(s) in a $V_H$ domain from a conventional four-chain antibody from a human being. This can be performed in a manner known per se, which will be clear to the skilled person, on the basis of the further description herein and the prior art on humanization. Again, it should be noted that such humanized nanobodies of the invention can be obtained in any suitable manner known per se (i.e., as indicated under points (1)-(8) above) and thus are not strictly limited to polypeptides that have been obtained using a polypeptide that comprises a naturally occurring $V_HH$ domain as a starting material. Humanized nanobodies may have several advantages, such as a reduced immunogenicity, compared to the corresponding naturally occurring $V_HH$ domains. Such humanization generally involves replacing one or more amino acid residues in the sequence of a naturally occurring $V_HH$ with the amino acid residues that occur at the same position in a human $V_H$ domain, such as a human VH3 domain. The humanizing substitutions should be chosen such that the resulting humanized nanobodies still retain the favorable properties of nanobodies as defined herein. The skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_HH$ domains on the other hand.

For example, both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" nanobody of the invention, respectively. This nucleic acid can then be expressed in a manner known per se, so as to provide the desired nanobody of the invention. Alternatively, based on the amino acid sequence of a naturally occurring VHH domain or VH domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized Nanobody of the invention, respectively, can be designed and then synthesized de novo using techniques for nucleic acid synthesis known per se, after which the nucleic acid thus obtained can be expressed in a manner known per se, so as to provide the desired nanobody of the invention. Other suitable methods and techniques for obtaining the nanobodies of the invention and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring V.sub.HH sequences (such as one or more FR sequences or CDR sequences), and/or one or more synthetic or semi-synthetic sequences, in a suitable manner, so as to provide a nanobody of the invention or a nucleotide sequence or nucleic acid encoding the same.

Also within the scope of the invention are natural or synthetic analogs, mutants, variants, alleles, homologs and orthologs (herein collectively referred to as "variants") of the immunoglobulin single variable domains of the invention as defined herein. Thus, according to one embodiment of the invention, the term "immunoglobulin single variable domain of the invention" in its broadest sense also covers such variants, in particular variants of the nanobodies of SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, 108, and 112 which bind to CD206 and SEQ ID NO: 122, which binds to FOLR2. Generally, in such variants, one or more amino acid residues may have been replaced, deleted and/or added, compared to the nanobodies of the invention as defined herein. Such substitutions, insertions or deletions may be made in one or more of the framework regions and/or in one or more of the CDRs. Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1 variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST. (See, e.g., Higgins & Sharp, CABIOS 5:151 (1989); Altschul S. F., W. Gish, W. Miller, E. W. Myers, D. J. Lipman. Basic local alignment search tool. J. Mol. Biol. 1990; 215:403-10.) Software for performing BLAST analyses is publicly available through the National Center for Biotechnology Information (on the worldwide web at ncbi.nlm.nih.gov/). Such variants of immunoglobulin single variable domains may be of particular advantage since they may have improved potency or other desired properties.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about two, about five, about ten, up to about twenty, up to about thirty or up to about fifty or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about one, about three, about five, about ten, up to about twenty, up to about thirty or up to about fifty or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

By means of non-limiting examples, a substitution may, for example, be a conservative substitution (as described herein) and/or an amino acid residue may be replaced by another amino acid residue that naturally occurs at the same position in another $V_HH$ domain. Thus, any one or more substitutions, deletions or insertions, or any combination thereof, that either improve the properties of the nanobody of the invention or that at least do not detract too much from the desired properties or from the balance or combination of desired properties of the nanobody of the invention (i.e., to the extent that the nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the nanobodies thus obtained.

According to particularly preferred embodiments, variants of the immunoglobulin single variable domains, in particular the nanobodies of the present invention may have a substitution, deletion or insertion, of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3. More preferably, variants of the immunoglobulin single variable domains, in particular the nanobodies, of the present invention may have a conservative substitution (as defined herein) of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3.

Further, depending on the host organism used to express the immunoglobulin single variable domain of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example, to allow site-specific pegylation.

Examples of modifications, as well as examples of amino acid residues within the immunoglobulin single variable domain, preferably the nanobody sequence, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the immunoglobulin single variable domain of the invention, and in particular of one or more functional groups, residues or moieties that confer one or more desired properties or functionalities to the immunoglobulin single variable domain of the invention. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFvs and single domain antibodies), for which reference is, for example, made to Remington's Pharmaceutical Sciences, 16th ed., Mack Publishing Co., Easton, Pa. (1980). Such functional groups may, for example, be linked directly (for example, covalently) to a immunoglobulin single variable domain of the invention, or optionally via a suitable linker or spacer, as will again be clear to the skilled person. One of the most widely used techniques for increasing the half-life and/or reducing immunogenicity of pharmaceutical proteins comprises attachment of a suitable pharmacologically acceptable polymer, such as poly (ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFvs); reference is made to, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965. Various reagents for pegylation of proteins are also commercially available, for example, from Nektar Therapeutics, USA. Preferably, site-directed pegylation is used, in particular via a cysteine-residue (see, for example, Yang et al., Protein Engineering, 16, 10, 761-770 (2003). For example, for this purpose, PEG may be attached to a cysteine residue that naturally occurs in a nanobody of the invention, a nanobody of the invention may be modified so as to suitably introduce one or more cysteine residues for attachment of PEG, or an amino acid sequence comprising one or more cysteine residues for attachment of PEG may be fused to the N- and/or C-terminus of a nanobody of the invention, all using techniques of protein engineering known per se to the skilled person. Preferably, for the immunoglobulin single variable domains and proteins of the invention, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the immunoglobulin single variable domain or polypeptide of the invention. Another technique for increasing the half-life of an immunoglobulin single variable domain may comprise the engineering into bifunctional constructs (for example, one nanobody against the target MMR and one against a serum protein such as albumin) or into fusions of immunoglobulin single variable domains with peptides (for example, a peptide against a serum protein such as albumin).

Yet another modification may comprise the introduction of one or more detectable labels or other signal-generating groups or moieties, depending on the intended use of the labeled nanobody. Suitable labels and techniques for attaching, using and detecting them will be clear to the skilled person and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled nanobodies and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, diethylenetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link the nanobody of the invention to another protein, polypeptide or chemical compound that is bound to the other half of the binding pair, i.e., through formation of the binding pair. For example, a nanobody of the invention may be conjugated to biotin, and linked to another protein, polypeptide, compound or carrier conjugated to avidin or streptavidin. For example, such a conjugated nanobody may be used as a reporter, for example, in a diagnostic system where a detectable signal-producing agent is conjugated to avidin or streptavidin. Such binding pairs may, for example, also be used to bind the nanobody of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the nanobody of the invention.

According to a preferred embodiment, the immunoglobulin single variable domain of the present invention is fused to a detectable label, either directly or through a linker. Preferably, the detectable label is a radio-isotope or radioactive tracer, which is suitable for medical applications, such as in in vivo nuclear imaging. Examples include, without the purpose of being limitative, $^{99m}$Tc, $^{123}$I, $^{125}$I, $^{111}$In, $^{18}$F, $^{64}$Cu, $^{67}$Ga, $^{68}$Ga, and any other radio-isotope which can be used in animals, in particular mouse or human.

In still another embodiment, the immunoglobulin single variable domain of the present invention is fused to a moiety selected from the group consisting of a toxin, or to a cytotoxic drug, or to an enzyme capable of converting a prodrug into a cytotoxic drug, or to a radionuclide, or coupled to a cytotoxic cell, either directly or through a linker.

As used herein, "linkers" are peptides of 1 to 50 amino acids length and are typically chosen or designed to be unstructured and flexible. These include, but are not limited to, synthetic peptides rich in Gly, Ser, Thr, Gln, Glu or further amino acids that are frequently associated with unstructured regions in natural proteins. (See, e.g., Dosztanyi Z., V. Csizmok, P. Tompa, and I. Simon (2005). IUPred: web server for the prediction of intrinsically unstructured regions of proteins based on estimated energy content. Bioinformatics (Oxford, England), 21(16), 3433-4.) Non-limiting examples of suitable linker sequences are described in the Example section, and include $(G_4S)_3$ (GGGGSGGGGSGGGGS; SEQ ID NO:110), llama IgG2 hinge (AHHSEDPSSKAPKAPMA; SEQ ID NO:109, see also, SEQ ID NO:113) or human IgA hinge (SPSTPPTPSP-STPPAS SEQ ID NO:147) linkers.

In other embodiments, the targeting unit is an immunoglobulin or fragment thereof. Examples include, but are not limited to, aptamers and immunoglobulins. Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "$F_V$" area that contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Monoclonal antibodies against target antigens (e.g., a cell surface protein, such as receptors) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than-the mouse system. Splenocytes from the transgenic mice are immunized with the antigen of interest, which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggeman et al. Eur. J. Immunol., 21:1323-1326 [1991]).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and the PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies. (See e.g., Larrick et al., Biotechniques, 11:152-156 [1991]). A similar strategy can also be used to amplify human heavy and light chain variable regions from human antibodies (See e.g., Larrick et al., Methods: Companion to Methods in Enzymology, 2:106-110 [1991]).

In one embodiment, RNA is isolated from B lymphocytes, for example, peripheral blood cells, bone marrow, or spleen preparations, using standard protocols (e.g., U.S. Pat. No. 4,683,292 [incorporated herein by reference in its entirety]; Orlandi, et al., Proc. Nat. Acad. Sci. USA, 86:3833-3837 [1989]; Sastry et al., Proc. Nat. Acad. Sci. USA, 86:5728-5732 [1989]; and Huse et al., Science, 246:1275 [1989]). First strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries, examples of methods and reagents particularly amenable for use in generating a variegated antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809 [each of which is herein incorporated by reference in its entirety]; Fuchs et al., Biol. Technology, 9:1370-1372 [1991]; Hay et al., Hum. Antibod. Hybridomas, 3:81-85 [1992]; Huse et al., Science, 46:1275-1281 [1989]; Hawkins et al., J. Mol. Biol., 226:889-896 [1992]; Clackson et al., Nature, 352:624-628 [1991]; Gram et al., Proc. Nat. Acad. Sci. USA, 89:3576-3580 [1992]; Garrad et al., Bio/Technolog, 2:1373-1377 [1991]; Hoogenboom et al., Nuc. Acid Res., 19:4133-4137 [1991]; and Barbas et al., Proc. Nat. Acad. Sci. USA, 88:7978 [1991]. In certain embodiments, the V region domains of heavy and light chains can be expressed on the same polypeptide, joined by a flexible linker to form a single-chain Fv fragment, and the scFV gene subsequently cloned into the desired expression vector or phage genome.

As generally described in McCafferty et al., Nature, 348:552-554 (1990), complete $V_H$ and $V_L$ domains of an antibody, joined by a flexible linker (e.g., $(Gly_4\text{-}Ser)_3$) can be used to produce a single chain antibody which can render the display package separable based on antigen affinity. Isolated scFV antibodies immunoreactive with the antigen can subsequently be formulated into a pharmaceutical preparation for use in the subject method. CL10scFV, which binds FOLR2)(See, e.g., SEQ ID NO:120 and 121 and sequences having at least 80%, 90%, 95%, 99% and 100% identity thereto; US Pat. Publ. 20140010756, incorporated herein by reference in its entirety) is a non-limiting example of a scFv useful as a targeting unit in the present invention.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g., from the phage genome) and subcloned into other expression vectors by standard recombinant DNA techniques.

Specific antibody molecules with high affinities for a surface protein can be made according to methods known to those in the art, e.g., methods involving screening of libraries U.S. Pat. Nos. 5,233,409 and 5,403,484 (both incorporated herein by reference in their entireties). Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence in formation, by a modeling procedure using previously determined three-dimensional structures from other antibodies obtained from NMR studies or crystallographic data.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are known in the art.

Other techniques include affinity chromatography with an appropriate "receptor," e.g., a target antigen, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library. (See e.g., W. C. Still et al., WO 94/08051 incorporated herein by reference in its entirety). In general, this method features the use of inert but readily detectable tags that are attached to the solid support or to the compounds. When an active compound is detected, the identity of the compound is determined by identification of the unique accompanying tag. This tagging method permits the synthesis of large libraries of compounds that can be identified at very low levels among to total set of all compounds in the library.

The term modified antibody is also intended to include antibodies, such as monoclonal antibodies, chimeric antibodies, and humanized antibodies which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314: 446-449 [1985]; and Shaw et al., J. Natl. Cancer Inst., 80:1553-1559 [1988]).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In some embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of various isotypes, including, but not limited to: IgG (e.g., IgG1, IgG2, IgG2a, IgG2b, IgG2c, IgG3, IgG4); IgM; IgA1; IgA2; IgA$_{sec}$; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')$_2$, Fv or a single chain Fv fragment).

In preferred embodiments, the immunoglobulin is a recombinant antibody (e.g., a chimeric or a humanized antibody), a subunit, or an antigen binding fragment thereof (e.g., has a variable region, or at least a complementarity determining region (CDR)).

In some embodiments, the immunoglobulin is monovalent (e.g., includes one pair of heavy and light chains, or antigen binding portions thereof). In other embodiments, the immunoglobulin is a divalent (e.g., includes two pairs of heavy and light chains, or antigen binding portions thereof).

In some embodiments, a system of hybridoma-like antibody preparation, developed by Neoclone (Madison, Wis.), is used in the production of monoclonal antibodies. Splenocytes from immunized mice are immortalized using a retrovector-mediated introduction of the abl-myc genes. On reintroduction into recipient mice one dominant immortalized B cell clone (plasmacytoma) outgrows all others and produces a monoclonal antibody in the ascitic fluid. The B cell clone can be harvested with the ascitic fluid that contains high concentration of monoclonal antibody. This process can be completed in 8-10 weeks.

It will be understood that the CDRs or variable domains from the novel nanobodies and/or single domain antibodies described above may be identified (See Table 1) and cloned and then inserted into a desired variable region or framework region to provide, for example, a humanized antibody, Fab, F(ab')$_2$, Fab' single chain antibody, Fv, single chain (scFv), mono-specific antibody, bi-specific antibody, tri-specific antibody, multivalent antibody, chimeric antibody, humanized antibody, human antibody, CDR-grafted antibody, microbody, intrabody (e.g., intracellular antibody), and/or de-fucosylated antibody and/or derivative thereof. Suitable CDR1, CDR2, and CDR3 sequences may be cloned, from example, any one of the nanobodies encoded by the following amino acid sequences: SEQ ID NOs: 30-56, 58, 60, 62, 64, 66, 68, 70, 72, 74, 76, 78, 80, 82, 84, 86, 88, 90, 92, 94, 96, 98, 100, 102, 104, 106, 108, and 112 which bind to CD206 and SEQ ID NO: 122, which binds to FOLR2; or the following nucleic acid sequences: SEQ ID NOs:3, 57, 59, 61, 63, 65, 67, 69, 71, 73, 75, 77, 79, 81, 83, 85, 87, 89, 91, 93, 95, 97, 99, 101, 103, 105, 107 and 111, which encode nanobodies which bind to CD206 and SEQ ID NO:123 which encodes a single domain antibody which binds to FOLR2.

It will be understood that antigen binding protein is may be identified with reference to the nucleotide and/or amino acid sequence corresponding to the variable and/or complementarity determining regions ("CDRs") thereof. For instance, an exemplary antigen binding protein that is derived from, or is related to the nanobodies described above may comprise a heavy and/or a light chain that each comprise one or more constant and/or variable regions. The variable regions typically comprise one or more CDRs that in large part determine the binding specificity of the antibody. These antigen binding proteins may be identified by analysis of the nucleotide sequences encoding the variable regions. The antigen binding proteins may also be identified by analysis of the amino acid sequences of (e.g., which may be encoded by the nucleotide sequences) the variable regions.

Any of the variable regions or CDRs of the nanobodies described above (or variants thereof sharing at least 80% identity) may be combined with any other variable region and/or CDR in any order and/or combination to form hybrid and/or fusion binding agents and/or inserted into other heavy and/or light chain variable regions using standard techniques. These may be used in conjunction with any constant regions.

CDRs (complementarity-determining regions) are amino acid sequences from antibodies that are, at least in part, responsible for binding of an antibody to a specific target. It is understood by those of skill in the art that CDRs may be identified using any of several techniques and/or schemes. CDRs of the nanobodies shown herein may be identified using any of these techniques. For example, the CDRs of nanobodies may be identified as described above. The nanobodies have three CDR regions, each non-contiguous with the others (termed CDR1, CDR2, CDR3). The delineation of the FR and CDR sequences is often based on the IMGT unique numbering system for V-domains and V-like domains. (See, e.g., Lefranc M. P., C. Pommie, et al. (2003). "IMGT unique numbering for immunoglobulin and T cell receptor variable domains and Ig superfamily V-like domains." Developmental and Comparative Immunology 27(1): 55-77.) Alternatively, the delineation of the FR and CDR sequences can be done by using the Kabat numbering system as applied to $V_HH$ domains from Camelids in the article of Riechmann and Muyldermans. (See, e.g., Riechmann and Muyldermans J. Immunol. Methods 2000; 240: 185-195.) As will be known by the person skilled in the art, the nanobodies can in particular be characterized by the presence of one or more Camelidae hallmark residues in one or more of the framework sequences (according to Kabat numbering), as described, for example, in WO 08/020,079, on page 75, Table A-3, incorporated herein by reference).

A summary of various schemes, in part based on, for example, Kabat et al, "Sequences of Proteins of Immunological Interest," 5th Ed., Public Health Service, National Institutes of Health, Bethesda, Md., NIH publication No. 91-3242 (1991), and Al-Lazikani et al, "Standard conformations for the canonical structures of immunoglobulins," J. Mol. Biol. 273:927-948, 1997, is provided in Table 2 below:

TABLE 2

| CDR Loop* | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31-H35B (Kabat Numbering) | H26--H35B | H26--H32 . . . 34 | H30--H35B |
| H1 | H31--H35 (Chotia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

*L = light chain;
H = heavy chain

CDRs may also be identified by following a set of rules such as those set forth in Table 3 below (as described on the world wide web at bioinforg.uk/abs/#cdrid):

TABLE 3

| CDR*/Feature | Typical Characteristic of Feature** |
|---|---|
| CDR-L1 | |
| Start | approximately residue 24 |
| Residues before | typically Cys |
| Residues after | typically Trp (e.g., Trp-Tyr-Gln, Trp-Leu-Gln, Trp-Phe-Gln, Trp-Tyr-Leu) |
| Length | 10 to 17 residues |
| CDR-L2 | |
| Start | typically 16 residues after the end of L1 |
| Residues before | typically Ile-Tyr, Val-Tyr, Ile-Lys, or Ile-Phe |
| Length | typically seven (7) residues |
| CDR-L3 | |
| Start | typically 33 residues after end of L2 |
| Residues before | typically Cys |
| Length | typically Phe-Gly-X-Gly (SEQ ID NO: 197) |
| Residues after | 7 to 11 residues |
| CDR-H1 | |
| Start | Approximately residue 26 (typically four (4) residues after a Cys) (Chothia/AbM definition); Kabat definition starts 5 residues later |
| Residues before | typically Cys-X-X-X (SEQ ID NO: 198) |
| Residues after | typically Trp (e.g., Trp-Val, Trp-Ile, Trp-Ala) |
| Length | 10 to 12 residues (AbM definition); Chothia definition excludes the last four (4) residues |
| CDR-H2 | |
| Start | typically 15 residues after the end of Kabat/AbM definition of CDR-H1 |
| Residues before | typically Leu-Glu-Trp-Ile-Gly (SEQ ID NO: 199) |
| Residues after | typically Lys/Arg-Leu/Ile/Val/ Phe/Thr/Ala-Thr/Ser/Ile/Ala (SEQ ID NO: 200) |
| Length | Kabat definition 16 to 19 residues; AbM (and recent Chothia) definition 9 to 12 residues |

TABLE 3-continued

| CDR*/Feature | Typical Characteristic of Feature** |
|---|---|
| CDR-H3 | |
| Start | typically 33 residues after end of CDR-H2 (typically two (2) residues following a Cys) |
| Residues before | typically Cys-X-X (typically Cys-Ala-Arg) |
| Residues after | typically Trp-Gly-X-Gly (SEQ ID NO: 201) |
| Length | typically 3 to 25 residues |

*L = light chain;
H = heavy chain;
**X = any amino acid

These systems for identifying CDRs are merely exemplary and others may be suitable, as would be understood by one of ordinary skill in the art. CDRs thus identified may be used to identify suitable antigen binding proteins. These systems may be used to identify the CDR region of an antigen binding protein so that the CDRs of the present invention may be used to replace existing CDRs in the antigen binding protein or inserted into an appropriate framework or variable region of the antigen binding protein. Such CDRs may also be combined with one another in any order and/or combination to form hybrid and/or fusion binding agents and/or inserted into the other heavy and/or light chain variable regions using standard techniques. The amino acid sequences of the nanobodies, and/or any one or more fragments and/or derivatives thereof, may be encoded by any of several nucleic acid sequences. These nucleic acid sequences may also be used to identify and/or prepare (e.g., as nucleic acid molecules) suitable antigen binding proteins. For example, one of ordinary skill in the art may devise nucleotide sequences encoding any such amino acid sequences. Any of the nucleotide sequences and/or fragments and/or derivatives thereof, may be combined with one another in any order and/or combination to encode hybrid and/or fusion binding agents and/or inserted into the other nucleic acid sequences encoding light and/or heavy chain variable regions (and/or fragments and/or derivatives thereof).

The variable region sequences described herein (which may comprise fragments and/or derivatives thereof), including but not limited to the variable regions of the nanobodies described above (and/or fragments and/or derivatives thereof) an/or their corresponding nucleotide sequences (and/or fragments and/or derivatives thereof) may be used in combination with one or more amino acid sequences and/or nucleotide sequences encoding one or more constant chains (and/or a fragment and/or derivatives thereof) of an antibody molecule. For instance, the variable region amino acid sequences of the nanobodies may be joined to the constant regions of any antibody molecule of the same or a different species (e.g., human, goat, rat, sheep, chicken) of that from which the variable region amino acid sequence was derived. The constant regions may be derived from any of, for example, human (e.g., IgG (IgG1, IgG2, IgG3, IgG4), IgM, IgA (IgA1 and IgA2), IgD, and IgE), canine (e.g., IgG (IgGA, IgGB, IgGC, IgGD) IgA, IgD, IgE, and IgM), chicken (e.g., IgA, IgD, IgE, IgG, IgM, IgY), goat (e.g., IgG), mouse (e.g., IgA, IgG, IgD, IgE, IgM), pig (e.g., IgA, IgG, IgD, IgE, IgM), rat (e.g., IgA, IgG, IgD, IgE, IgM), feline (e.g., IgA, IgD, IgE, IgG, IgM) and/or a fragment and/or derivative thereof (e.g., as chimeric antibodies). Accordingly, the CDRs or variable regions of the nanobodies may be used to produce a humanized antibody, Fab, F(ab')$_2$, Fab' single chain antibody, Fv, single chain (scFv), mono-specific antibody, bi-specific antibody, tri-specific antibody, multivalent antibody, chimeric antibody, humanized antibody, human antibody, CDR-grafted antibody, microbody, intrabody (e.g., intracellular antibody), and/or de-fucosylated antibody and/or derivative thereof, as is known in the art.

2. Immunostimulatory Agents

The fusion protein of the present invention may include a variety of different immunostimulatory agents. In some embodiments, the immunostimulatory agent in a fusion protein of the present invention is selected from an interleukin, an interferon, and a tumor necrosis factor.

The present invention is not limited to the use of any particular interleukins in the fusion proteins. In some embodiments, the interleukins are selected from IL-1β, IL-2 (SEQ NO:22 and 118 (human na sequence), SEQ ID NO:23 and 119 (human aa sequence)), IL-7 (SEQ NO:131 (human na sequence), SEQ ID NO:132 (human aa sequence)), IL-8, IL-12, IL-15 (SEQ ID NO:7, 8, 116 (human na sequences), SEQ ID NO:9 and 117 (human aa sequence)), IL-17 (SEQ NO:18 and 136 (human na sequence), SEQ ID NO:19 and 137 (human aa sequence)), IL-18 (SEQ NO:28 and 124 (mouse na sequence), SEQ ID NO:29 and 125 (mouse aa sequence)), IL-21 (SEQ ID NO:14 and 132 (mouse na sequence), SEQ ID NO:15 and 133 (mouse aa sequence), SEQ ID NO:16 (human na sequence), SEQ ID NO:17 (human aa sequence)), IL-23, IL-27 (SEQ NO:26 (mouse na sequence), SEQ ID NO:27 (mouse aa sequence)) and IL-33, functional subunits of the interleukins as well interleukin fusions such as IL15-RLI (SEQ NO:114 (na sequence), SEQ ID NO:115 (aa sequence)) which a fusion of IL15 to the sushi domain of IL-15Rα, and improved variants such as the hIL2-C125A human IL2 superagonist (SEQ NO:24 and 126 (na sequence), SEQ ID NO:25 and 127 (aa sequence)). The sequence information for exemplary interleukins, fusions and variants has been provided. It will be recognized by those of skill in the art that the sequences, for example, human or mouse sequences, for the remaining interleukins are known in the art and readily obtainable. In some embodiments, the interleukins used in the fusion proteins share at least 80%, 90%, 95%, 99%, or 100% identity with the interleukins identified above.

The present invention is not limited to the use of any particular interferons in the fusion proteins. In some embodiments, the interferons are selected from IFNα1 (SEQ NO:12 and 134 (mouse na sequence), SEQ ID NO:13 and 135 (mouse aa sequence)), IFNα2, IFNβ1, IFNε1, IFNγ, IFNκ, and IFNω. The sequence information for exemplary interferons has been provided. It will be recognized by those of skill in the art that the sequences, for example, human or mouse sequences, for the remaining intererons are known in the art and readily obtainable. In some embodiments, the interferons used in the fusion proteins share at least 80%, 90%, 95%, 99%, or 100% identity with the interleukins identified above.

The present invention is not limited to the use of any particular tumor necrosis factors (TNFs) in the fusion proteins. In some embodiments, the TNFs are selected from TNFα (SEQ NO:20 and 128 (human na sequence), SEQ ID NO:21 and 129 (human aa sequence)), CD40L, EDA, FASL, LTA, LTB, RANKL, OX40L, TNFSF7, TNFSF8, TNFSF9, TNFSF12, TNFSF13, TNFSF13B, F18, TRAIL, BAFF, 4-1BBL, and 4-1BB. The sequence information for exemplary TNFs has been provided. It will be recognized by those of skill in the art that the sequences, for example, human or mouse sequences, for the remaining TNFs are known in the art and readily obtainable. In some embodiments, the TNFs used in the fusion proteins share at least 80%, 90%, 95%, 99%, or 100% identity with the interleukins identified above.

In some preferred embodiments, the immunostimulatory agent is IL-15 polypeptide (SEQ ID NO:7, 8, 116 (human na sequences), SEQ ID NO:9 and 117 (human aa sequence)) or IL15-IL15Rα fusion such as IL15-RLI (SEQ NO:114 (na sequence), SEQ ID NO:115 (aa sequence)) which a fusion of IL15 to the sushi domain of IL-15Rα. The subunits for the IL15-RLI fusion are preferably identified by SEQ ID NO:5 (IL15Rα sushi domain), SEQ ID NO:6 (Linker 20) and SEQ ID NO:7 (hIL15). IL15-RIL sequences and constructs are further described in US Pat. Publ. 20090238791, incorporated by reference herein in its entirety.

IL15 is a cytokine possessing all the qualities needed to elicit a potent immune response; it induces T cell activation and cell division, triggers cytotoxic effector pathways in T- and NK-cells, and supports T cell longevity. Based on these properties, IL15 has been considered one of the most attractive cytokine for tumor immunotherapy. Administration of IL15 has been evaluated in phase I/II trials that have documented that recombinant IL15 has an acceptable safety profile.

Using the targeting approach described herein, the present invention offers a means of selectively targeting IL15 to tumor-associated macrophages. Our approach allows one to exploit the full therapeutic potential of localized, intratumoral release of IL15 in a manner that has not been previously achieved.

Embodiments of the present invention provide fusion proteins and nucleic acids comprising such fusion proteins, comprising an immunostimulatory agent (e.g., IL15 polypeptide, IL15 receptor, or fragment thereof) fused to a targeting unit that targets the IL15 polypeptide to a tumor associated macrophage. In some embodiments, the targeting unit binds to CD206. In some embodiments, targeting unit is an immunoglobulin or fragment thereof that specifically binds to CD206. In some embodiments, the immunoglobulin is a single domain antibody (sdAb) fragment or a single chain variable fragments (scFv), although other antibody or antibody fragments are specifically contemplated. In some embodiments, the fusion polypeptide is 206RLI.

The present invention is not limited to particular immunostimulatory agents. Examples include, but are not limited to, IL-15, additional cytokines (e.g., interferon alpha, interferon gamma, interleukin-21, interleukin-17, interleukin-18, interleukin-27, TNF-α, interleukin 2, interleukin 7, interleukin 12); costimulatory ligands (e.g., 41bb, CD80, CD86); and antibody fragments with agonistic or antagonistic activity against immune checkpoints (e.g., anti-PD1, anti-CTLA4, etc).

The present invention is not limited to particular targeting units or targets. Examples include, but are not limited to, mannose receptor (CD206), folate receptor beta (FOLR2) and leugmain (LGMN). Other target structures on macrophages are identified though an evaluation of surface marker expression. In some embodiments, other stromal cell subsets such as tumor-associated fibroblasts substitute as the target cell type, and in this case, fibroblast activating protein (FAP), S100A4 and FSP-1 are examples of targets.

3. Fusions of Targeting Unit and Immunostimulatory Agents

In some embodiments, the present invention provides fusion proteins comprising a targeting unit in operable association with an immunostimulatory agent. Preferred targeting units and immunostimulatory agents are identified above. In some preferred embodiments, the targeting unit is an antigen binding protein, e.g., an antibody, immunoglobulin, or fragments thereof, nanobody, scFv, etc. In some preferred embodiments, the immunostimulaotry agent is a polypeptide selected from the group consisting of an interleukin, and interferon and a TNF.

Preferably, the targeting unit and the immunostimulaotry agent are operably connected to one another by a linker. As used herein, "linkers" are peptides of 1 to 50 amino acids length and are typically chosen or designed to be unstructured and flexible. These include, but are not limited to, synthetic peptides rich in Gly, Ser, Thr, Gln, Glu or further amino acids that are frequently associated with unstructured regions in natural proteins. (See, e.g., Dosztanyi Z., V. Csizmok, P. Tompa, and I. Simon (2005). IUPred: web server for the prediction of intrinsically unstructured regions of proteins based on estimated energy content. Bioinformatics (Oxford, England), 21(16), 3433-4.) Non-limiting examples of suitable linker sequences are described in the Example section, and include $(G_4S)_3$ (GGGGSGGGGSGGGGS; SEQ ID NO:110), llama IgG2 hinge (AHHSEDPSSKAPKAPMA; SEQ ID NO:109, see also, SEQ ID NO:4 and SEQ ID NO:113) or human IgA hinge (SPSTPPTPSPSTPPAS SEQ ID NO:147) linkers. It will be readily understood that other linkers may be utilized.

The present invention is not limited to any particular fusion protein comprising a targeting unit in operable association with an immunostimulatory agent. It will understood that the targeting units described above may be paired with any of the immunostimulatory agents. Table 4 provides non-limiting examples of fusion proteins of the present invention.

TABLE 4

| SEQ ID NO: | SEQUENCE TYPE AMINO ACID (AA) NUCLEIC ACID (NA) | TARGETING UNIT | IMMUNO-STIMULATORY AGENT |
|---|---|---|---|
| 1 | NA | CD206 nanobody | IL15-RLI |
| 2 | AA | CD206 nanobody | IL15-RLI |
| 138 | NA | CD206 nanobody | hIL15 |
| 139 | NA | CD206 nanobody | hIL2 |
| 140 | NA | CL10scFV | IL15-RLI |
| 141 | NA | FOLR2sdAB | IL15-RLI |
| 142 | NA | FOLR2sdAB | hIL15 |
| 143 | NA | FOLR2sdAB | hIL2 |
| 144 | NA | CD206 nanobody | IL15-RLI |
| 145 | NA | CD206 nanobody | hIL15 |
| 146 | NA | CD206 nanobody | hIL2 |
| 153 | NA | CD206 nanobody | hIL18 |
| 154 | NA | CD206 nanobody | hIL17 |
| 155 | NA | CD206 nanobody | hTNFa |
| 156 | NA | CD206 nanobody | hIFNa |
| 157 | NA | CD206 nanobody | hIL21 |
| 158 | NA | FOLR2sdAB | hIL18 |
| 159 | NA | FOLR2sdAB | hIL17 |
| 160 | NA | FOLR2sdAB | hTNFa |
| 161 | NA | FOLR2sdAB | hIFNa |
| 162 | NA | FOLR2sdAB | hIL21 |
| 163 | NA | CD206 nanobody | h41BBL |
| 164 | NA | FOLR2sdAB | h41BBL |
| 165 | NA | CD206 nanobody | hOX40L |
| 166 | NA | FOLR2sdAB | hOX40L |
| 167 | NA | CD206 nanobody | hCD40L |
| 168 | NA | FOLR2sdAB | hCD40L |
| 169 | NA | CD206 nanobody | hIL17 |
| 170 | NA | FOLR2sdAB | hIL17 |

The fusion proteins of the present invention are not limited to the particular sequences disclosed in Table 4. In some embodiments, the present invention encompasses variants of the identified sequences. For example, in some embodiments, the present invention provides variants of the sequences listed in table 4 that have at least 80%, 90%, 95%, 99% or 100% identity to the fusion proteins (i.e., the amino acid sequences) encoded by the sequences.

4. Vectors and Expression

In some embodiments, the present invention provides nucleic acids encoding the antigen binding proteins and fusion proteins described above. In some embodiments, the present invention provides vectors comprising the nucleic acids, as well as host cells comprising the vectors that are utilized for expression of the antigen binding proteins and/or fusion proteins. In some embodiments, the present invention provides vectors and recombinant expression systems for expressing peptides and constructs described herein. The present invention is not limited to particular expression vectors. Exemplary vectors and expression methods are described herein.

In some embodiments, peptides are expressed using any suitable vector and expression system. In some embodiments, peptides are expressed in bacterial or eukaryotic expression vectors (e.g., commercially available vectors). In some embodiments, peptides are expressed in retroviral (e.g., adeno, adeno-associated, or lenti-viral vectors). Suitable vectors are introduced into suitable host cells (e.g., bacterial or eukaryotic host cells), expression is induced, and peptides are isolated using any suitable method.

The peptides, polypeptides, and proteins of the present invention may be produced by recombinant techniques. Thus, for example, a polynucleotide encoding a peptide, polypeptide or protein of the present invention may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, retroviral vectors and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above. In some embodiments of the present invention, the constructs comprise a vector, such as a plasmid or viral vector, into which a sequence of the invention has been inserted, in a forward or reverse orientation. In still other embodiments, the heterologous structural sequence is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In some embodiments, retroviral vectors are utilized for expression in a suitable host cell. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [–PBS], the 3' regulatory sequences required for reverse transcription [+PBS] and the viral LTRs). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); the resulting virus is said to be replication defective or incompetent.

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus [VSV]). The transfected packaging cell will then produce viral particles that contain the membrane-associated protein expressed by the transfected packaging cell line; these viral particles, which contain viral genomic RNA derived from one virus encapsidated by the envelope proteins of another virus are said to be pseudotyped virus particles.

Commonly used recombinant retroviral vectors are derived from the amphotropic Moloney murine leukemia virus (MoMLV) (Miller and Baltimore, Mol. Cell. Biol., 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Other commonly used retrovectors are derived from lentiviruses including, but not limited to, human immunodeficiency virus (HIV) or feline immunodeficiency virus (FIV). Lentivirus vectors have the advantage of being able to infect non replicating cells.

The low titer and inefficient infection of certain cell types by retro vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al., Proc. Natl. Acad. Sci. USA, 90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus human immunodeficiency virus, and other lentiviral vectors.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 (1981)), C127, 3T3, 293, 293T, HeLa and BHK cell lines, T-1 (tobacco cell culture line), root cell and cultured roots in rhizosecretion (Gleba et al., (1999) Proc Natl Acad Sci USA 96:5973-5977).

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

5. Formulations

Where clinical applications are contemplated, in some embodiments of the present invention, the fusion proteins are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a fusion protein composition formulation may be administered using one or more of the routes described herein.

In some embodiments, the fusion protein compositions are used in conjunction with appropriate salts and buffers to render delivery of the compositions in a stable manner to allow for uptake by target cells. Buffers also are employed when the compositions are introduced into a patient. Aqueous compositions comprise an effective amount of composition dispersed in a pharmaceutically acceptable carrier or aqueous medium. Such compositions also are referred to as inocula.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The compositions may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, compositions are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer.

"Treating" within the context of the instant invention, means an alleviation, in whole or in part, of symptoms associated with a disorder or disease, or slowing, inhibiting or halting of further progression or worsening of those symptoms, or prevention or prophylaxis of the disease or disorder in a subject at risk for developing the disease or disorder. Thus, e.g., treating cancer may include inhibiting or preventing the metastasis of the cancer, a reduction in the speed and/or number of the metastasis, a reduction in tumor volume of the metastasized cancer, a complete or partial remission of the metastasized cancer or any other therapeutic benefit. As used herein, a "therapeutically effective amount" of a compound of the invention refers to an amount of the compound that alleviates, in whole or in part, symptoms associated with a disorder or disease, or slows, inhibits or halts further progression or worsening of those symptoms, or prevents or provides prophylaxis for the disease or disorder in a subject at risk for developing the disease or disorder.

A subject is any animal that can benefit from the administration of a compound as described herein. In some embodiments, the subject is a mammal, for example, a human, a primate, a dog, a cat, a horse, a cow, a pig, a rodent, such as for example a rat or mouse. Typically, the subject is a human.

A therapeutically effective amount of a compound as described herein used in the present invention may vary depending upon the route of administration and dosage form. Effective amounts of invention compounds typically fall in the range of about 0.001 up to 100 mg/kg/day, and more typically in the range of about 0.05 up to 10 mg/kg/day. Typically, the compound or compounds used in the instant invention are selected to provide a formulation that exhibits a high therapeutic index. The therapeutic index is the dose ratio between toxic and therapeutic effects which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

The instant invention also provides for pharmaceutical compositions and medicaments which may be prepared by combining one or more compounds described herein, pharmaceutically acceptable salts thereof, stereoisomers thereof, tautomers thereof, or solvates thereof, with pharmaceutically acceptable carriers, excipients, binders, diluents or the like to inhibit or treat primary and/or metastatic prostate cancers. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, or via implanted reservoir. Parenteral or systemic administration includes, but is not limited to, subcutaneous, intravenous, intraperitoneal, and intramuscular injections. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Compounds of the invention may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (TWEENs, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the invention.

Aerosols containing compounds for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Delivery of aerosols of the present invention using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds maybe formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal administration of compounds of the invention include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the invention to the body. Such dosage forms can be made by dissolving or dispersing the agent in the proper medium. Absorption enhancers can also be used to increase the flux of the inventive compound across the skin. The rate of such flux can be controlled by either providing a rate controlling membrane or dispersing the compound in a polymer matrix or gel.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

In some embodiments of the present invention, methods and compositions are provided for the treatment of tumors and. In some embodiments, the cancer is, for example, lung cancer, breast cancer, pancreatic cancer, prostate cancer, melanoma or multiple myeloma.

Other cell proliferative disorders, or cancers, contemplated to be treatable with the methods of the present invention include human sarcomas and carcinomas, including, but not limited to, fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, acute lymphocytic leukemia and acute myelocytic leukemia (myeloblastic, promyelocytic, myelomonocytic, monocytic and erythroleukemia), chronic leukemia (chronic myelocytic (granulocytic) leukemia and chronic lymphocytic leukemia), polycythemia vera, lymphoma (Hodgkin's disease and non-Hodgkin's disease), multiple myeloma, Waldenstrom's macroglobulinemia, and heavy chain disease.

Tumor cell resistance to chemotherapeutic agents represents a major problem in clinical oncology. In some embodiments, compositions and methods of the present invention provide means of ameliorating this problem by effectively administering a combined therapy approach. However, it should be noted that traditional combination therapy may be employed in combination with the compositions of the present invention. For example, in some embodiments of the present invention, immunotherapies are used before, after, or in combination with the traditional therapies.

To kill cells, inhibit cell growth, or metastasis, or angiogenesis, or otherwise reverse or reduce the malignant phenotype of tumor cells using the methods and compositions of the present invention in combination therapy, one contacts a "target" cell with the compositions described herein and at least one other agent. These compositions are provided in a combined amount effective to kill or inhibit proliferation of the cell. This process may involve contacting the cells with the immunotherapeutic agent and the agent(s) or factor(s) at the same time. This may be achieved by contacting the cell with a single composition or pharmacological formulation that includes both agents, or by contacting the cell with two distinct compositions or formulations, at the same time.

Alternatively, immunotherapy with the fusion proteins described herein precedes or follows the other agent treatment by intervals ranging from minutes to weeks. In embodiments where the other agent and immunotherapy are applied separately to the cell, one would generally ensure that a significant period of time did not expire between the time of each delivery, such that the fusion protein and chemotherapeutic agent would still be able to exert an advantageously combined effect on the cell. In such instances, it is contemplated that cells are contacted with both modalities within about 12-24 hours of each other and, more preferably, within about 6-12 hours of each other, with a delay time of only about 12 hours being most preferred. In some situations, it may be desirable to extend the time period for treatment significantly, however, where several days (2 to 7) to several weeks (1 to 8) lapse between the respective administrations.

In some embodiments, more than one administration of the immunotherapeutic composition of the present invention or the other agent is utilized. Various combinations may be employed, where the fusion protein is "A" and the other agent is "B", as exemplified below:

A/B/A, B/A/B, B/B/A, A/A/B, B/A/A, A/B/B, B/B/B/A, B/B/A/B,

A/A/B/B, A/B/A/B, A/B/B/A, B/B/A/A, A/B/A/B/A, B/A/A/B, B/B/B/A,

A/A/A/B, B/A/A/A, A/B/A/A, A/A/B/A, A/B/B/B, B/A/B/B, B/B/A/B.

Other combinations are contemplated. Again, to achieve cell killing, both agents are delivered to a cell in a combined amount effective to kill or disable the cell.

In some embodiments of the invention, one or more compounds of the invention and an additional active agent are administered to a subject, more typically a human, in a sequence and within a time interval such that the compound can act together with the other agent to provide an enhanced benefit relative to the benefits obtained if they were administered otherwise. For example, the additional active agents can be co-administered by co-formulation, administered at the same time or administered sequentially in any order at different points in time; however, if not administered at the same time, they should be administered sufficiently close in time so as to provide the desired therapeutic or prophylactic effect. In some embodiments, the compound and the additional active agents exert their effects at times which overlap. Each additional active agent can be administered separately, in any appropriate form and by any suitable route. In other embodiments, the compound is administered before, concurrently or after administration of the additional active agents.

In various examples, the compound and the additional active agents are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other examples, the compound and the additional active agents are administered concurrently. In yet other examples, the compound and the additional active agents are administered concurrently by co-formulation.

In other examples, the compound and the additional active agents are administered at about 2 to 4 days apart, at about 4 to 6 days apart, at about 1 week part, at about 1 to 2 weeks apart, or more than 2 weeks apart.

In certain examples, the inventive compound and optionally the additional active agents are cyclically administered to a subject. Cycling therapy involves the administration of a first agent for a period of time, followed by the administration of a second agent and/or third agent for a period of time and repeating this sequential administration. Cycling therapy can provide a variety of benefits, e.g., reduce the development of resistance to one or more of the therapies, avoid or reduce the side effects of one or more of the therapies, and/or improve the efficacy of the treatment.

In other examples, one or more compound of some embodiments of the present invention and optionally the additional active agent are administered in a cycle of less than about 3 weeks, about once every two weeks, about once every 10 days or about once every week. One cycle can comprise the administration of an inventive compound and optionally the second active agent by infusion over about 90 minutes every cycle, about 1 hour every cycle, about 45 minutes every cycle, about 30 minutes every cycle or about 15 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

Courses of treatment can be administered concurrently to a subject, i.e., individual doses of the additional active agents are administered separately yet within a time interval such that the inventive compound can work together with the additional active agents. For example, one component can be administered once per week in combination with the other components that can be administered once every two weeks or once every three weeks. In other words, the dosing regimens are carried out concurrently even if the therapeutics are not administered simultaneously or during the same day.

The additional active agents can act additively or, more typically, synergistically with the inventive compound(s). In one example, one or more inventive compound is administered concurrently with one or more second active agents in the same pharmaceutical composition. In another example, one or more inventive compound is administered concurrently with one or more second active agents in separate pharmaceutical compositions. In still another example, one or more inventive compound is administered prior to or subsequent to administration of a second active agent. The invention contemplates administration of an inventive compound and a second active agent by the same or different routes of administration, e.g., oral and parenteral. In certain embodiments, when the inventive compound is administered concurrently with a second active agent that potentially produces adverse side effects including, but not limited to, toxicity, the second active agent can advantageously be administered at a dose that falls below the threshold that the adverse side effect is elicited.

Other factors that may be used in combination therapy include, but are not limited to, factors that cause DNA damage such as γ-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In some embodiments of the present invention, the regional delivery fusion proteins to patients with cancers is utilized to maximize the therapeutic effectiveness of the delivered agent. Similarly, the chemo- or radiotherapy may be directed to a particular, affected region of the subject's body. Alternatively, systemic delivery of the immunotherapeutic composition and/or the agent may be appropriate in certain circumstances, for example, where extensive metastasis has occurred.

In addition to combining the fusion proteins of some embodiments of the present invention with chemo- and radiotherapies, it also is contemplated that traditional gene therapies are used. For example, targeting of p53 or p16 mutations along with treatment with the fusion proteins of the present invention provides an improved anti-cancer treatment. The present invention contemplates the co-treatment with other tumor-related genes including, but not limited to, p21, Rb, APC, DCC, NF-I, NF-2, BCRA2, p16, FHIT, WT-I, MEN-I, MEN-II, BRCA1, VHL, FCC, MCC, ras, myc, neu, raf erb, src, fms, jun, trk, ret, gsp, hst, bcl, and abl.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935, 114; 5,908,413; 5,792,105; 5,693,014; 5,674,192; 5,876, 445; 5,913,894; 5,868,719; 5,851,228; 5,843,089; 5,800, 519; 5,800,508; 5,800,391; 5,354,308; 5,755,722; 5,733, 303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

In some embodiments, composition embodiments of the present invention are co-administered with an anti-cancer agent (e.g., chemotherapeutic). In some embodiments, method embodiments of the present invention encompass co-administration of an anti-cancer agent (e.g., chemotherapeutic). The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino) ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N, N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hypertrophy therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-PO4; mitoxantrone; mitozolomide; Pentostatin; and Tomudex.

Other cancer therapies include hormonal manipulation. In some embodiments, the anti-cancer agent is tamoxifen or the aromatase inhibitor arimidex (i.e., anastrozole).

In some embodiments, the additional agent is Mitomycin C.

In some embodiments, the therapies described herein are used in combination with other immunotherapies (e.g., CAR-T/TCR and/or checkpoint inhibitors).

EXPERIMENTAL

The following examples are provided in order to demonstrate and further illustrate certain preferred embodiments and aspects of the present invention and are not to be construed as limiting the scope thereof.

Example 1—Generation of Nanobodies and Constructs

Reagents, mice and cell lines. Recombinant human IL-15 (rIL-15), human IL-2 (rhIL-2), murine IL-4 (rmIL-4) and murine interferon gamma (rmIFNg) were purchased from Peprotech Inc (Rocky Hill, N.J.). The IL-2-dependent CTLL-2 cell line (American Type Culture Collection, ATCC) was maintained in RPMI1640 medium containing 10% FCS, 2 mM glutamine, 10 ng/ml rhIL-2.

C57B16 mice were obtained from Taconic (Taconic Farms, Rye, Denmark) and bred in-house in a Specific-pathogen-free (SPF) facility. Tumor challenge was performed by s.c. injection with 2×105 B16 melanoma cells (ATCC).

The CHO cell line (ATCC) was used to generate cells expressing the murine or human mannose receptor (MRC1; CD206). STable transfectants were generated by electroporating the cells with a pCDNA3.1 plasmid containing the relevant cDNA (synthesized by Genscript). MRC1-expressing cells were selected by flow sorting of cells staining positive using an anti-MRC1 antibody.

NSO hybridoma scells (Sigma Aldrich) were used to generate human/mouse FOLR2-expressing cells. Cells were transduced with pMSCV IRES GFP vectors expressing cDNA-containing encoding the relevant receptor (obtained from OriGene). Stably transduced cells were selected by flow sorting of GFP+ cells staining positive with an anti-FOLR2 mAb. All cells were maintained in RPMI1640 medium containing 10% FCS.

The *Escherichia coli* production strain Rv308 was obtained from ATCC.

Generation of Anti-MRC1 sdAbs.

For the generation of a phage display library with human/mouse cross-reactivity, a llama (*Llama glama*) was immunized s.c. with alternating doses of human and mouse recombinant MRC1 (R&D Systems) in GERBU adjuvant with 7-day intervals for a total of 6 weeks. The two initial immunizations utilized 200 µg MRC1, whereas subsequent doses were 100 µg each. Upon completion of the immunization schedule, total RNA was isolated from peripheral blood lymphocytes. Construction of a VHH library and subsequent biopanning and next-generation sequencing was performed by a commercial service provider (Creative Biolabs, Shirley, N.Y.). In brief, cDNA was generated using a AMV Super Reverse Transcriptase kit (HT Biotechnology Ltd, Cambridge, UK) according to the manufacturer's instructions, using Oligo(dT) primers. Amplified VHH sequences were inserted into the pCDisplay-3M phagemid vector (Creative Biolabs), and electroporated into *E. coli* TG1 cells. Transformants were infected with M13K01 helper phages (New England Biolabs) to generate VHH-expressing phages. Phage biopanning was performed using recombinant human and mouse MRC1 (R&D systems). After 4 successive rounds of panning, DNA from the enriched phage library was subjected to next generation sequencing to score enriched clones using the VectorNTI bioinformatics software package (Thermo Scientific). The most highly enriched sequences were those represented by SEQ ID NOs:30-56. Top candidates were codon-optimized for expression in *E. coli* (amino acid and nucleic acid sequences provided as SEQ ID NOs:57-108), and synthesized fragments inserted downstream of the PelB signal of the pHOG21 expression vector. Monovalent sdAb candidates containing an N-terminal cMyc/6×His tag were expressed and purified as specified below, and binding to MRC1-expressing CHO cells verified by flow cytometry staining using a PE-conjugated anti-His antibody.

Generation of Anti-FOLR2 sdAbs.

Immunization of llamas was performed as described for the anti-MRC1 antibodies, using recombinant human and mouse FOLR2 (R&D systems). Upon completion of the immunization schedule, total RNA was isolated from peripheral blood lymphocytes and cDNA synthesized using the First Stand cDNA synthesis kit (Thermo Scientific), utilizing oligo(dT) primers, according to the supplied protocol. VHH sequences were amplified in a two-step approach, based on a previously published protocol. In short, $V_HH$s were amplified using primers CALL001 (5'-GTCCTGGCTGCTCTTCTACAAGG-3'; SEQ ID NO:148) and CALL002 (5'-GGTACGTGCTGTTGAACTGTTCC-3; SEQ ID NO:149'), specific for the $V_HH$ leader sequence and CH2 exon, respectively. The PCR mixture was separated on 1% agarose gels, and the 700 bp VHH fragments were extracted and subjected to a second PCR using nested primers VHH-Back (5'-GATGTGCAG CTGCAGGAGTCTGGRGGAGG-3'; SEQ ID NO:150; PstI cut site underlined) and VHH-For: (5'-CTAGTGCGGCCGCTGGAGACGGTGACCTGGGT-3';

SEQ ID NO:151; Eco91I site underlined), specific for framework 1 and framework 4 regions, respectively. PCR fragments were cut using PstI/Eco91I restriction enzymes, and ligated into the corresponding sites of the pMESY4 phagemid vector. Ligated vector was electroporated into *E. Coli* SS320 cells and plated on LB plates containing 100 ug/mL ampicillin. Cells were collected by scraping, and stored at −80° C. in LB medium with 50% glycerol. For production of phages, cells were infected with VSCM13 helper phages (Cat. no. 200251; Stratagene). FOLR2-specific phages were enriched by three consecutive rounds of cell-based in vitro selection. Negative selection was done using a combination of molecular and cell-based banning. For cell-based panning, phages were incubated with 50×106 NSO cells for negative selection, with subsequent positive selection and elution of bound particles from NSO cells expressing human or mouse FOLR2. Individual clones were screened by flow cytometry for selective binding to tumor cells overexpressing FOLR2. VHH sequences from binders were codon optimized for expression in *E. coli*, and expressed alone or in fusion with cytokine partners as specified below.

Generation of Anti-LGMN sdAbs.

Immunization of llamas and subsequent library construction is performed as described for FOLR2, using recombinant human and murine legumain extracellular domains as immunogens, with identical immunization dosage/intervals. A sdAb library is constructed by cDNA synthesis using RNA extracted from PBMCs collected at the termination of the immunization protocol. The library is generated in the pMESY4 phagemid vector.

Generation of sdAb/Cytokine Fusion Proteins.

Nucleotide sequences encoding fusion proteins were codon-optimized for expression in *E. coli* and generated by gene synthesis for insertion into the NcoI/NotI site of the pHOG21 expression vector, downstream of the PelB leader sequence. A cMyc/6×His tag 3' of the MCS site was utilized to generate tagged variants of the fusion proteins. The relevant sdAb or scFv fragments were fused to cytokine moieties using the llama IgG2 hinge (AHHSEDPSSKAPKAPMA; SEQ ID NO: 109) or a $(G_4S)_3$ flexible linker (GGGGSGGGGSGGGGS; SEQ ID NO:110). The choice of linker did not seem to influence protein yield or biological activity of the fusion protein.

Expression and Purification of proteins in *E. coli*.

*E. coli* (RV308) cells (ATCC) were transformed with the pHOG21 plasmids described above and individual colonies from a freshly streaked agar plate were grown in LB media containing 100 µg/mL ampicillin and 100 mM glucose at 37° C. for 7 h. Preculture innoculum was transferred to 100 mL minimal medium and culture ON at 30° C. ON cultures were used to innoculate a bioreactor containing 4 L minimal medium. Fermentation was performed at 20-30° C. using O2-stat control, and feeding with glucose was initiated upon completion of the batch phase, signified by a rapid increase in dissolved 02 levels. Protein production was induced by injection of IPTG to a final concentration of 1 mM, and bacteria harvested by centrifugation at 50000×g 6 h after induction. For extraction of the periplasmic fraction, bacterial pellets were dissolved in periplasmic extraction buffer, stirred at room temperature for 10 min and pelleted by centrifugation at 14 000×g. Pellets were dissolved in cold destilled water, incubated at 4° C. for 10 minutes and centrifuged at 17 000×g for 30 minutes. Supernatant was filtered, and imidazol (final conc. 30 mM) and NaCl (final conc. 500 mM).

All proteins were purified using immobilized metal affinity chromatography (IMAC) using HiTrap IMAC HP columns (GE Healthcare), followed by cation exchange chromatography (CEX) on pre-packed HiTrap Capto SP ImpRes columns (GE Healthcare) to remove endotoxin. Endotoxin levels were determined using a LAL Chromogenic Endotoxin Quantitation Kit (Thermo Scientific). For proteins utilized in functional assays, a final polishing step was performed by size exclusion chromatography (SEC) using Superdex 75 10/300 GL columns (GE Healthcare) in endotoxin-free phosphate buffered saline pH 7.4 (PBS).

Proteins were transferred onto an Immobilon P membrane (Millipore Corporation, Bedford, USA) for immunoblotting. After blocking the membrane with phosphate buffered saline containing 0.2% Tween20 (PBS-Tween) and 1% skimmed milk, the relevant primary antibody was added and incubated for 2 hours at room temperature. Following washing, a HRP-labeled secondary antibody was added, followed by 1 hour incubation. The membrane was washed several times with PBS-Tween buffer before visualization of peroxidase activity by addition of SuperSignal West Pico Chemiluminescent Substrate (Thermo Scientific).

In Vitro T Cell Proliferation Assays.

To assess the biological effect of sdAb IL2/IL15 fusion proteins in vitro, we utilized the IL2-dependent T cell hybridoma CTLL-2 (ATCC). CTLL-2 cells were maintained in RPMI1640 medium with rhIL-2. Prior to use, cells were washed and starved by 24 h incubation in RPMI medium without rhIL-2. Candidate fusion proteins were added to the cells in 96-well plates, and incubated for 48 h, with addition of 3H-thymidine for the last 18 h of culture. Cells were harvested and measured using a TopCount scintillation counter (PerkinElmer, Waltham, Mass.).

Cells were harvested on nitrocellulose paper, and counts per minute (cpm) determined using a scintillation counter (PerkinElmer). rhIL-2 or rhIL-15 was used to generate a reference for growth-promoting activity.

Flow Cytometry

Binding of sdAb/cytokine fusion proteins was assayed by flow cytometry by exposing cells to the relevant fusion protein, followed by staining with antibodies reactive against the cytokine moiety or the 6×His tag.

Expression and Functional Evaluation of 206Nb-RLI Fusion Protein.

To evaluate the possibility of generating sdAb/cytokine fusion proteins, we utilized codon-optimized construct encompassing the scFv fragment of a previously characterized MRC1-specific sdAb described in US patent application US20120301394 (clone 1; hereafter referred to as 206Nb). The 206Nb fragment (SEQ ID NOs: 111 and 112) was linked via a Llama IgG2 hinge (SEQ ID NO: 112 and 113) to a sequence encoding the IL15 receptor sushi/hIL15 fusion protein (IL15RLI; SEQ ID 6, 7). The resulting construct, referred to as 206Nb-RLI (SEQ ID NO: 1 and 2), was inserted downstream of the PelB signal sequence (MKSLLPTAAAGLLLLAAQPA; SEQ ID NO:152) of the pHOG21 expression vector, and the construct electroporated into RV380 cells.

Figure 4:
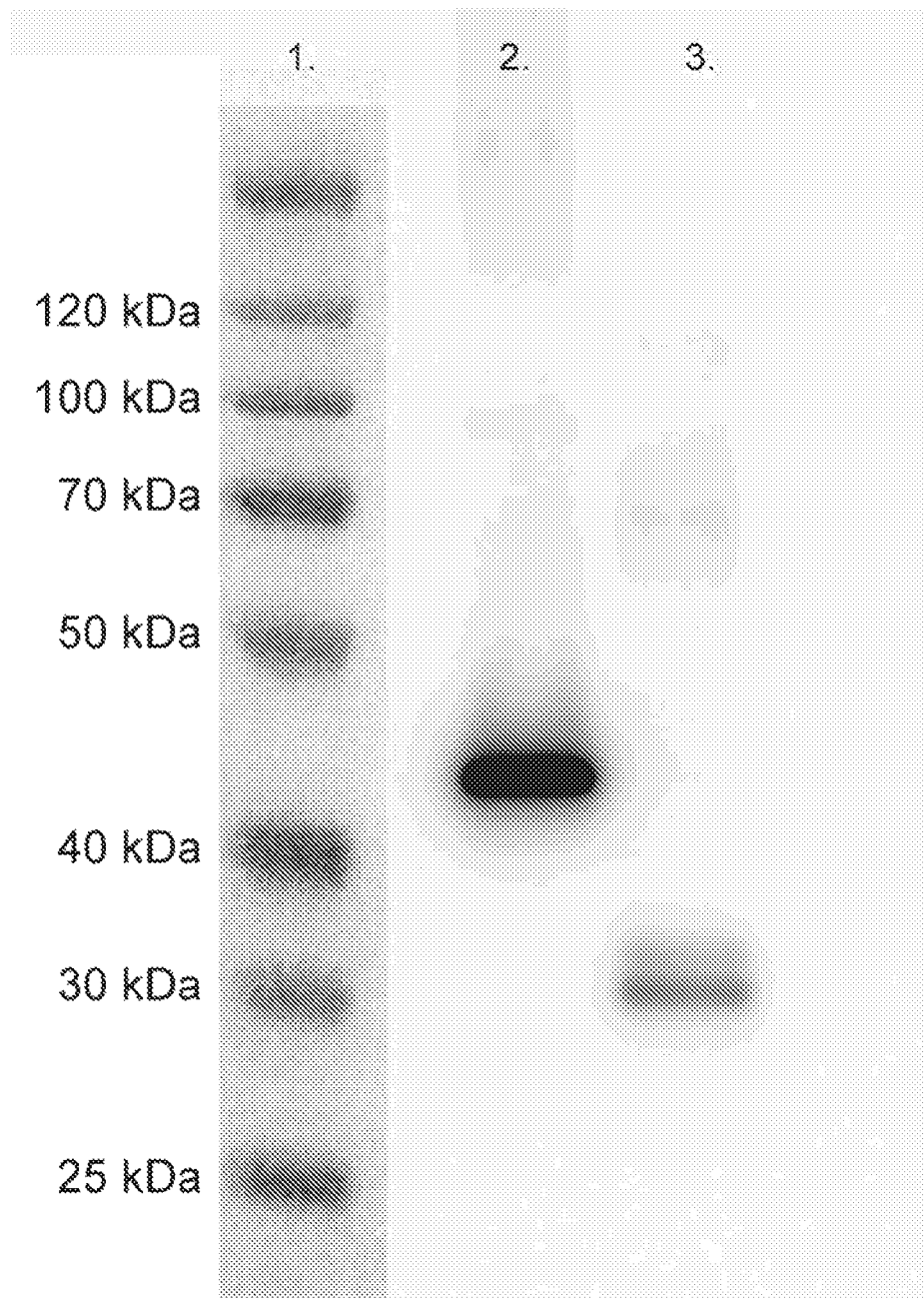
FIG. 4. Western blot using an anti-IL15 mAb.

Following IPTG-induced periplasmic expression at 30° C., the protein was isolated by affinity chromatography using sepharose-conjugated anti-IL15 column, followed by CEX. The resulting protein was present as a monomer of expected size of approx. 40 kDa, and was detected in a western blot using an anti-IL15 mAb (#MAB2471; R&D systems) (FIG. 4, lane 2).

Figure 5:
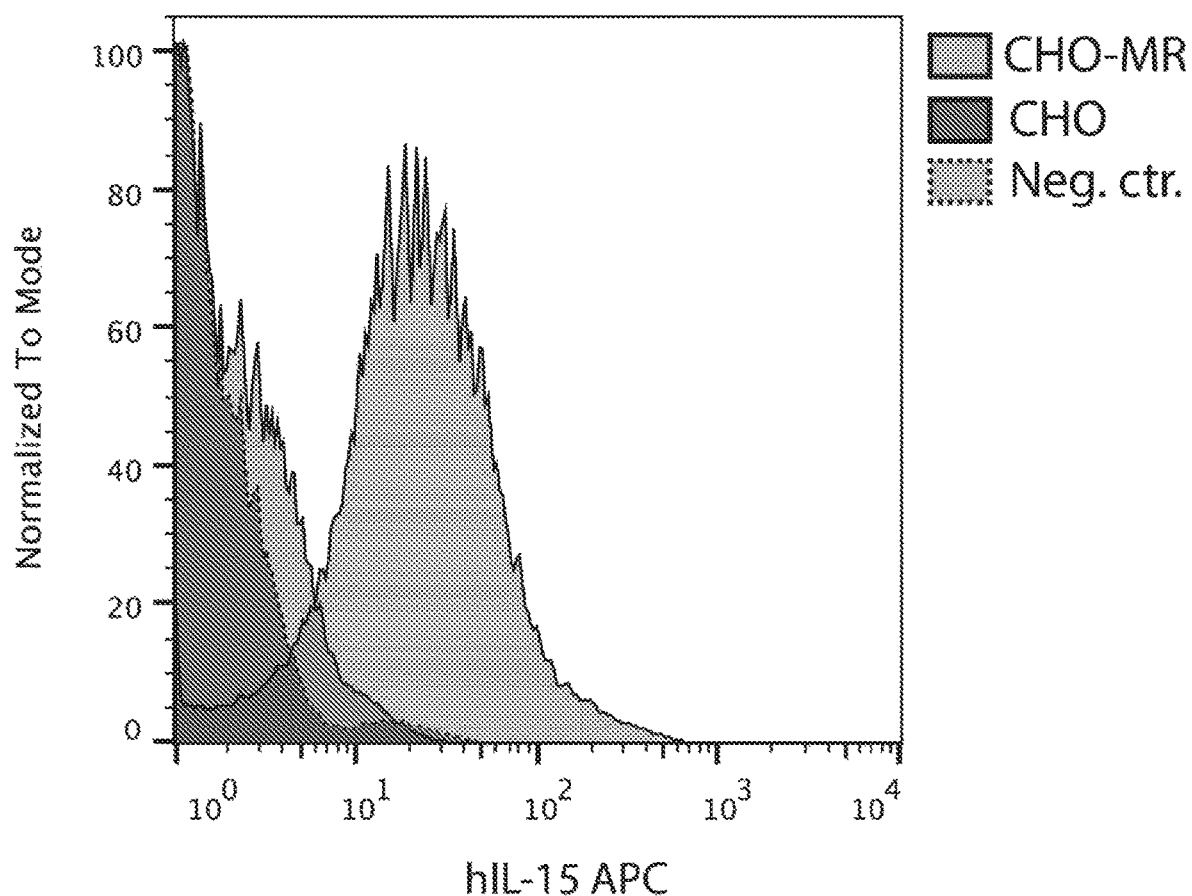
FIG. 5. Results from flow cytometry using an APC-conjugated anti-IL15 antibody.
Figure 6:
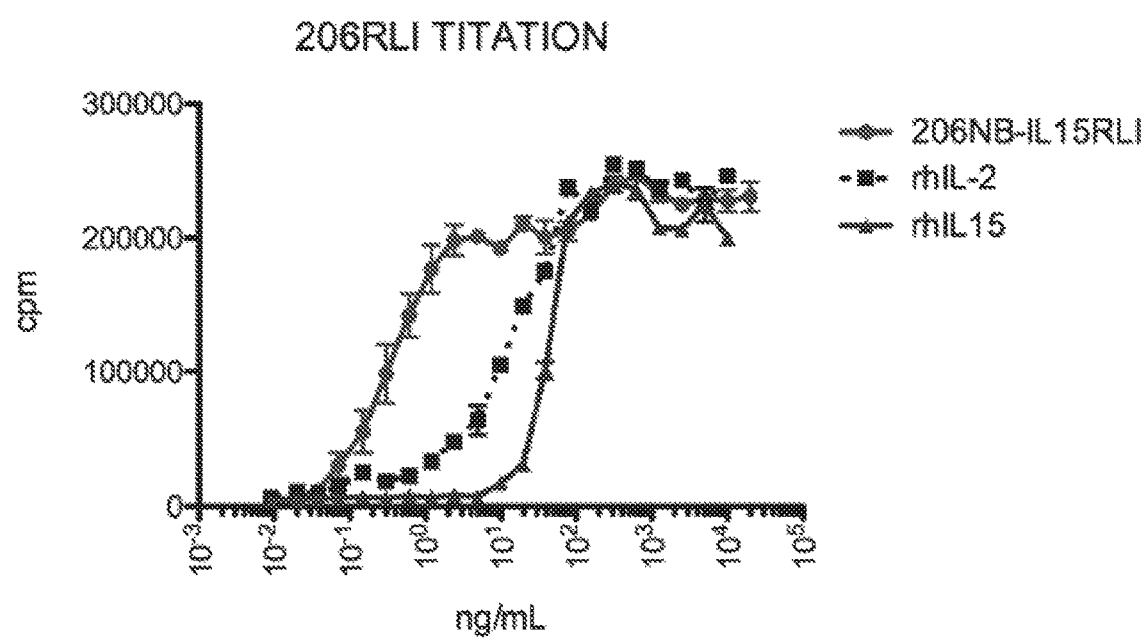
FIG. 6. Results of a CTLL-2 proliferation assay.

Binding to mMRC1-expressing CHO cells (CHO-MR) was verified by flow cytometry, using an APC-conjugated anti-IL15 antibody (#IC2471A; R&D Systems) for detection (FIG. 5). Functionality of the IL15RLI unit was confirmed by a CTLL-2 proliferation assay (FIG. 6).

A version of the fusion protein containing a C-terminal cMyc/6×His tag was also produced, and isolated by IMAC/CEX. Western blot using an anti-cMyc mAb (9E10; Abcam) confirmed a single band of the expected size (data not shown). CTLL-2 assays confirmed proliferative capability comparable to that of the tag-free variant (data not shown).

Expression and Functional Evaluation of 206Nb-hIL15 Fusion Protein.

Figure 7:
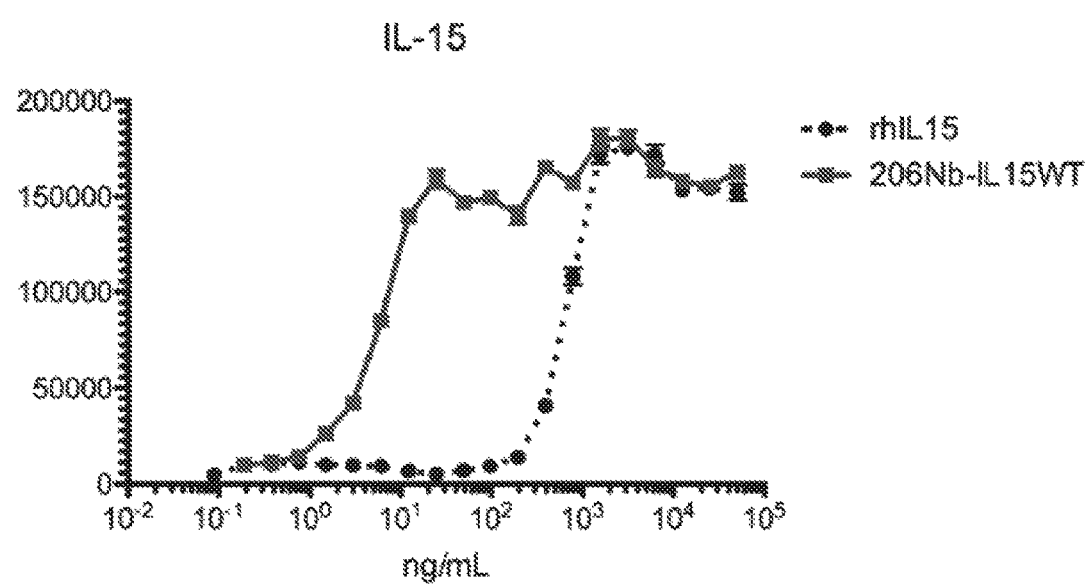
FIG. 7. presents results showing that the proliferation-inducing function of the 206Nb-hIL15 fusion protein fusion protein was superior to that of rhIL15 when used in CTLL-2 assays.

206Nb was fused to a sequence encoding human IL15 (SEQ ID NO:116 and 117), linked by a llama IgG2 hinge (SEQ ID NO:109), and a C-terminal cMyc/6×His tag. The sequence for the 206Nb-hIL15 fusion protein is provided as SEQ ID NO:138. Production was performed as described for 206RLI. Following IMAC/CEX purification, a single band of the expected size (approx. 30 kDa), detectable in western blots using an anti-IL15 mAb (data not shown) was observed. The proliferation-inducing function of the fusion protein was superior to that of rhIL15 when used in CTLL-2 assays (FIG. 7). Flow cytometry confirmed binding to CHO cells expressing mMRC1, with detection using antibodies against IL15 or the 6×His tag.

Expression and functional evaluation of a 206Nb-hIL2 fusion protein.

Figure 8:
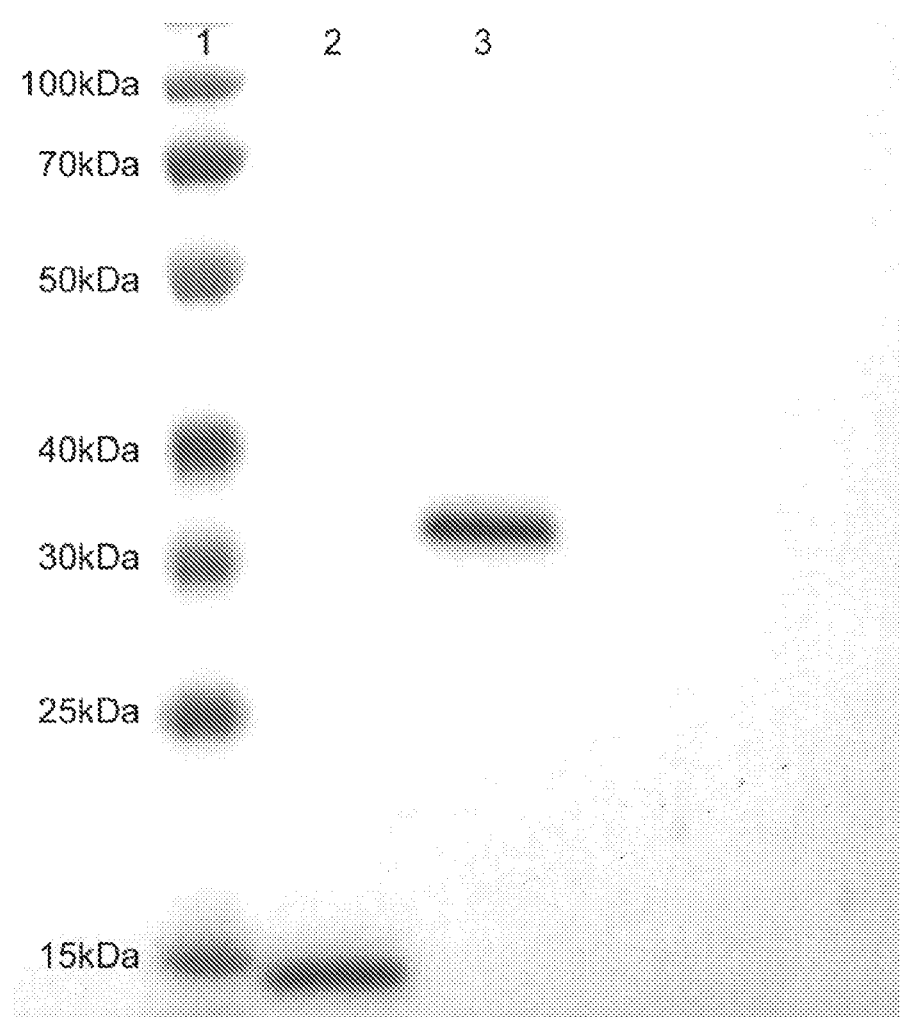
FIG. 8. Western blot using an anti-IL2 mAb.
Figure 9:
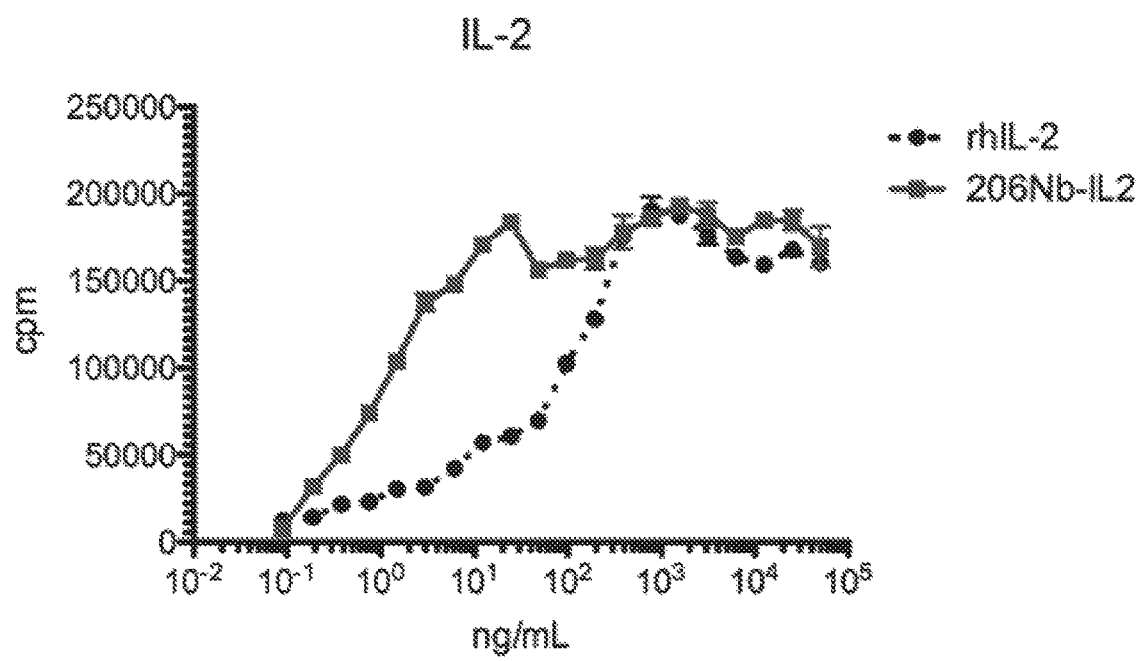
FIG. 9. Results showing that the proliferation inducing effects of a 206Nb-hIL2 fusion protein exceed that of rhIl2 in a CTLL-2 assay.

206Nb was fused to a sequence encoding human IL2 (SEQ ID NOs.: 118 and 119), linked by a llama IgG2 hinge (SEQ ID NO:109), and a C-terminal cMyc/6×His tag. Production was performed as described above. Following IMAC/CEX purification, a single band of the expected size (approx. 33 kDa), detectable in western blots using an anti-2 mAb (FIG. 8, lane 3) was observed. The protein showed strong proliferation-inducing effects, exceeding that of rhIl2 in CTLL-2 assays (FIG. 9). Flow cytometry confirmed binding to CHO cells expressing mMRC1, with detection using antibodies against IL2 or the 6×His tag.

Expression and Functional Evaluation of a CL10scFv-IL15RLI Fusion Protein.

Figure 10:
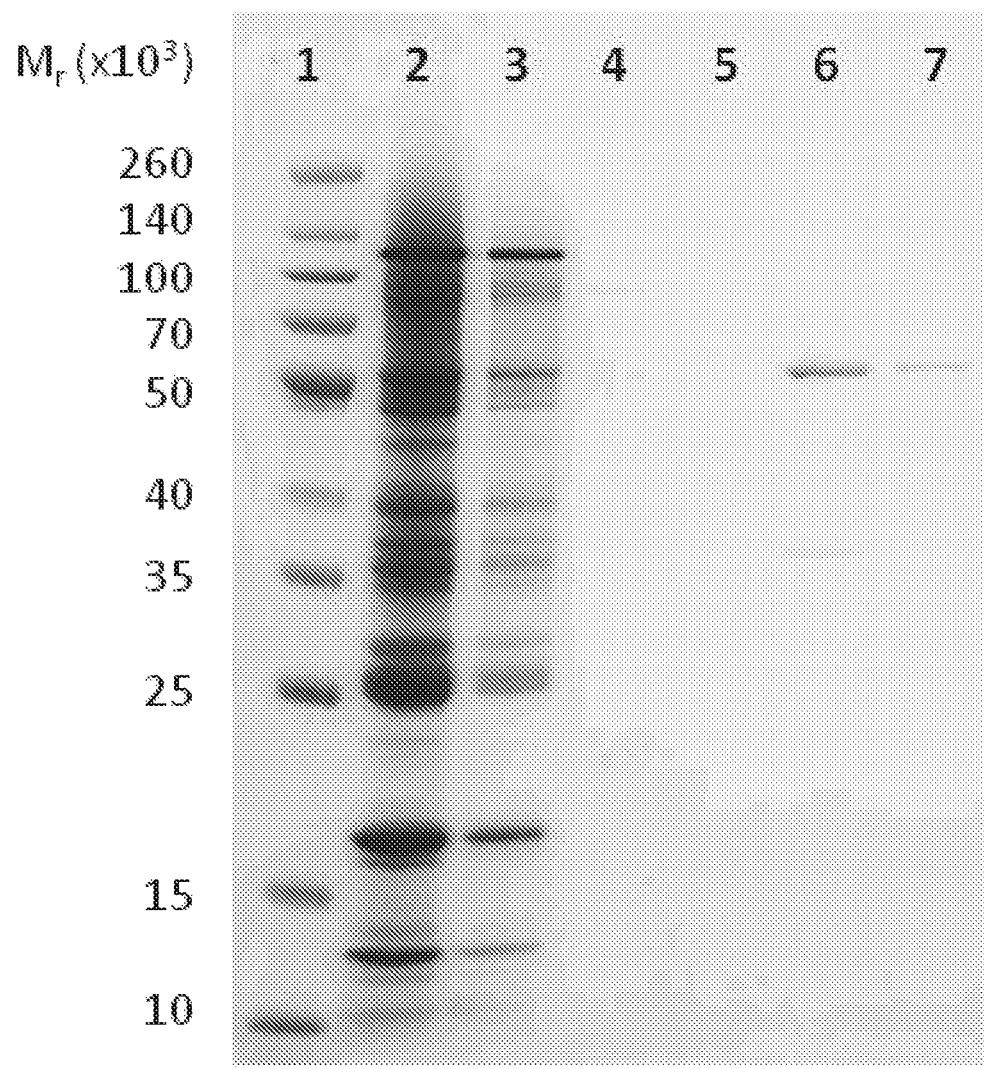
FIG. 10. Protein gel demonstrating purification of a CL10scFv-IL15RLI fusion protein.

We next wanted to explore the potential for extending macrophage targeting to fusion proteins containing scFv targeting units. A codon-optimized construct encompassing the scFv fragment of the rat anti-mouse FOLR2 mAb CL10 (SEQ ID NO:120 and 121; obtained from US patent application US20140010756), with VH and VL fragments connected by a (G₄S)₃ linker, was fused to IL15RLI (SEQ ID NO: 114 and 115), containing a C-terminal cMyc/6×His tag, via a (G₄S)₃ linker and inserted into the pHOG vector downstream of the PelB signal peptide. Protein expression was induced by ON induction with 1 mM IPTG at 25° C., and purification was done by IMAC/CEX. The purified protein (size approx 55 kDa; FIG. 10, lanes 6-7) showed binding to mFOLR2-expressing NS0 cells by flow cytometry, detected using an anti-IL15 or anti-6×His antibody (FIG. 11). Functionality of the IL15RLI unit was verified by a CTLL-2 assay.

206Nb-RLI Binding to In Vitro M2-Polarized Macrophages.

Figure 12:
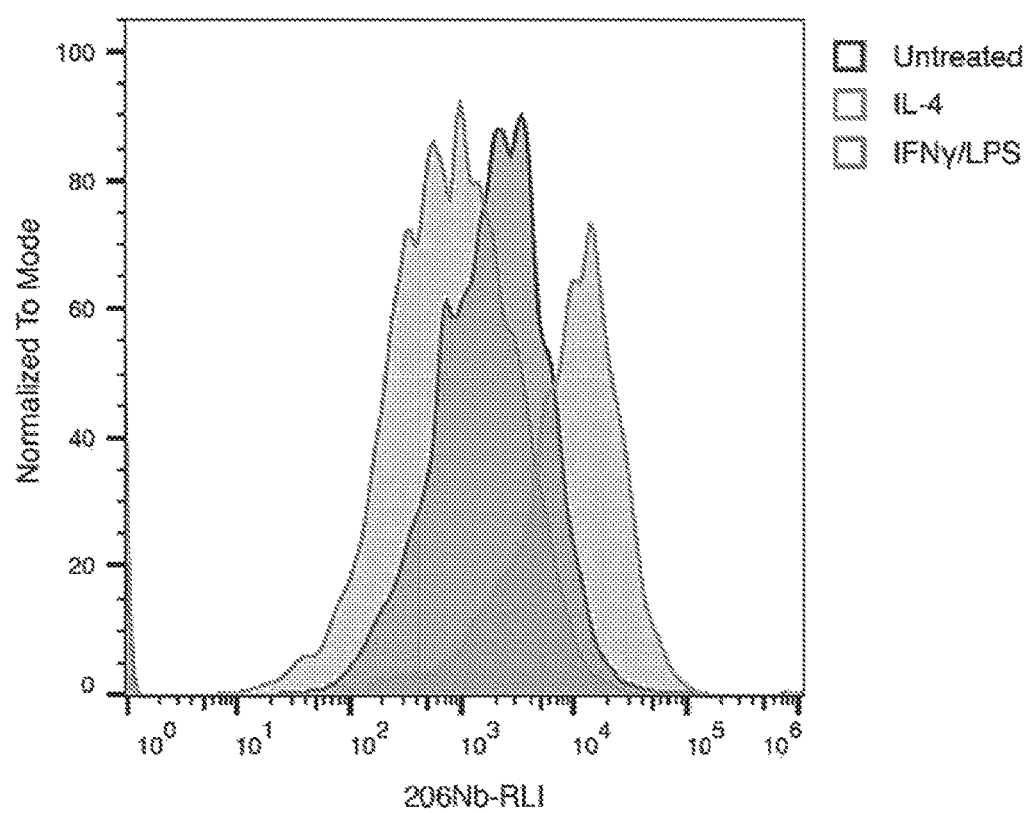
FIG. 12. Results of flow cytometry using the 206Nb-RLI fusion protein to stain IL-4-treated, M2-like macrophages.

To determine the ability of the 206Nb-RLI protein to bind to macrophages of different polarization, we cultured d+7 BMDMs for 24 h in the presence of rmIL-4 (10 ng/mL) or rmIFNg (100 ng/mL), known to induce an M2 or M1 phenotype, respectively. Flow cytometry staining using the 206Nb-RLI protein resulted in a preferential staining of IL-4-treated, M2-like macrophages (FIG. 12).

Expression and Functional Evaluation of a FOLR2sdAb-RLI Fusion Protein.

Biopanning of the FOLR2 sdAb library lead to the identification of a highly enriched clone (SEQ ID NO:122) that was codon-optimized (SEQ ID NO:123), and fused via a (G4S)3 linker to IL15RLI (SEQ ID NO: 114 and 115). The sequence of the entire construct is provided as SEQ ID NO:141. The protein was expressed in pHOG21 with a C-terminal cMyc/6×His tag.

In Vitro Binding of FOLR2sdAb-RLI to Tumor-Associated Macrophages.

Figure 13:
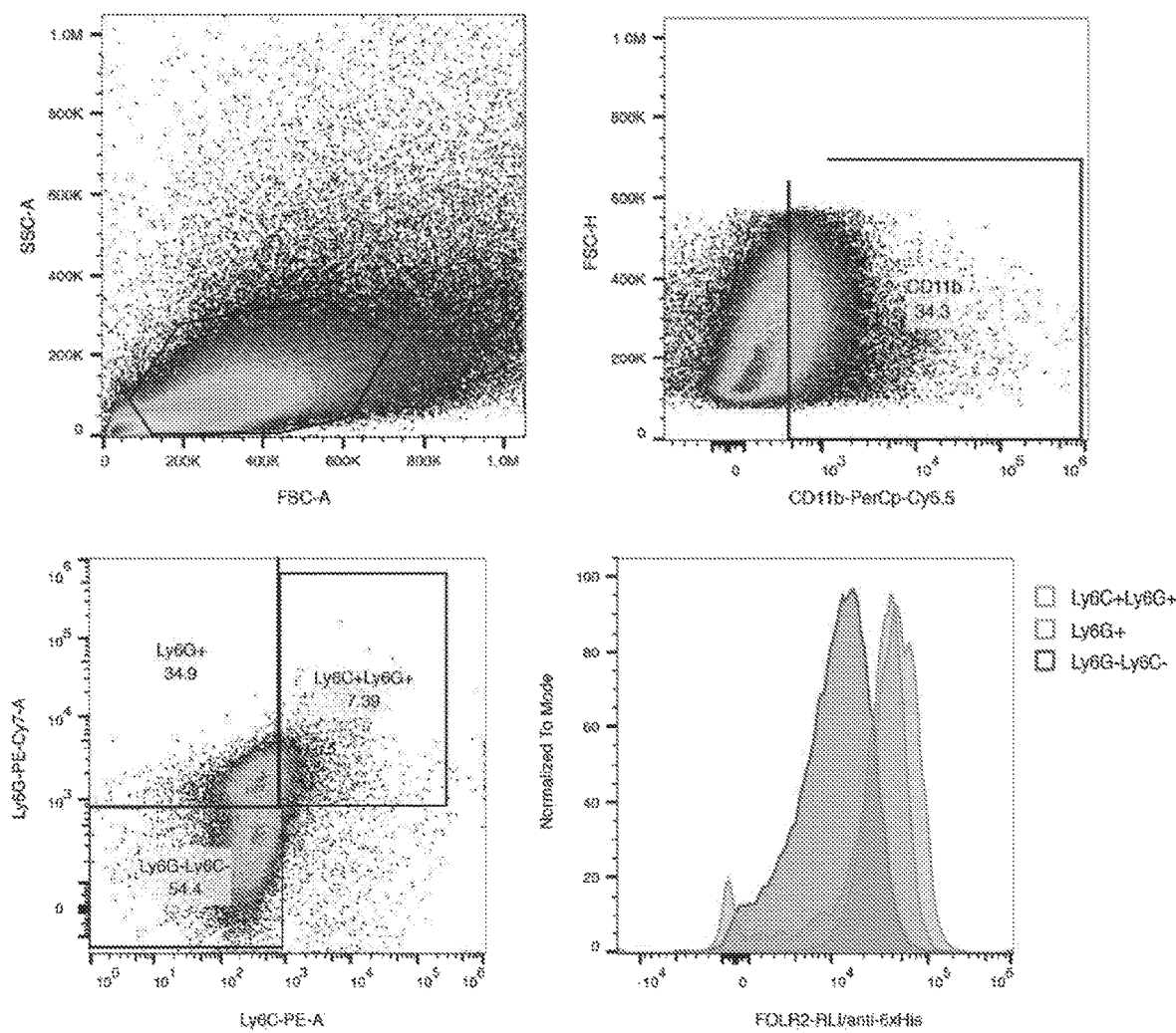
FIG. 13. Flow cytometry results showing preferential binding of FOLR2-RLI compared to the Ly6GNegLy6CNeg fraction and CD11bNeg cells, consistent with reactivity of the fusion protein against tumor-associated macrophages.

To evaluate binding of the FOLR2sdAb-RLI protein to physiologically differentiated tumor macrophages, we performed flow cytometry analyses of single-cell suspensions prepared from established B16 tumors. The tumor-resident CD11b+ population was found to consist primarily of Ly6GHiLy6Clo cells, showing preferential binding of FOLR2-RLI compared to the Ly6GNegLy6CNeg fraction and CD11bNeg cells (FIG. 13), consistent with reactivity of the fusion protein against tumor-associated macrophages.

Example 2—Animal Experiments

Well-established, clinically relevant murine models of various malignancies are used to evaluate the treatment efficacy of 206RLI. We have selected a screening panel of cancer types that are known to have a high degree of macrophage infiltration, and which represents patient groups with limited current therapeutic options. This includes lung cancer, breast cancer, pancreatic cancer, prostate cancer, melanoma and multiple myeloma. The cell lines utilized are commonly used and well-characterized, produce tumors with consistent growth kinetics, and are used to model advanced-stage, metastatic disease.

Therapy evaluation is performed using both subcutaneous and disseminated tumors. For melanoma and multiple myeloma, we have previously assessed the outcome of treatment with current standard-of-care regimens, and of monotherapy with checkpoint inhibitors including anti-PDL1 and anti-CTLA4. This will greatly facilitate evaluation of 206RLI as an adjunct to other treatment regimens. Initiation of treatment is delayed until the development of large lesions to allow evaluation of efficacy in advanced-stage disease. Intravenous administration of tumor cells allows studies of metastatic disease, and experiments are extended to this. Extension to orthotopic and spontaneous models of other types of malignancies are also performed.

Protein Production and Isolation:

Several candidate constructs have been constructed by gene synthesis and tested in functional assays (see below), and the best performing candidate (schematically illustrated in FIG. 1A) has been chosen for further development. Negative controls in the form of proteins containing a) an irrelevant targeting unit and/or b) a non-functional IL15 unit have also been developed.

By optimizing vectors used for periplasmic protein expression in *E. Coli*, we have generated plasmid constructs that allow high-yield production of soluble, tag-free protein in conventional shaker flask as well as in high-density cultures. Further purification is achieved using an anti-IL15 antibody immunoaffinity column.

In Vitro Characterization:

Isolated 206RLI protein has been verified to bind to human and murine CD206 with high affinity, confirming that the recombinant fusion protein retains target-binding properties. Functionality of the IL15 unit has been verified in T cell proliferation assays, showing potent growth-promoting effects on both murine and human T cells exceeding that of purified native IL15 (FIG. 2).

In Vivo Therapeutic Experiments:

The therapeutic efficacy of the 206RLI protein has been evaluated in preliminary experiments in murine models of myeloma and melanoma.

Experiments were performed in mice harboring palpable subcutaneous tumors with a diameter of >10 mm, which constitutes a high tumor burden. Treatment was done by systemic (i.p.) administration of 100 µg/dose every second day for nine days. In both cases, 206RLI treatment leads to the formation of a central necrotic ulceration within the tumors within a few days, and a rapid and dramatic shrinkage of tumors (FIG. 3A).

Figure 3B:
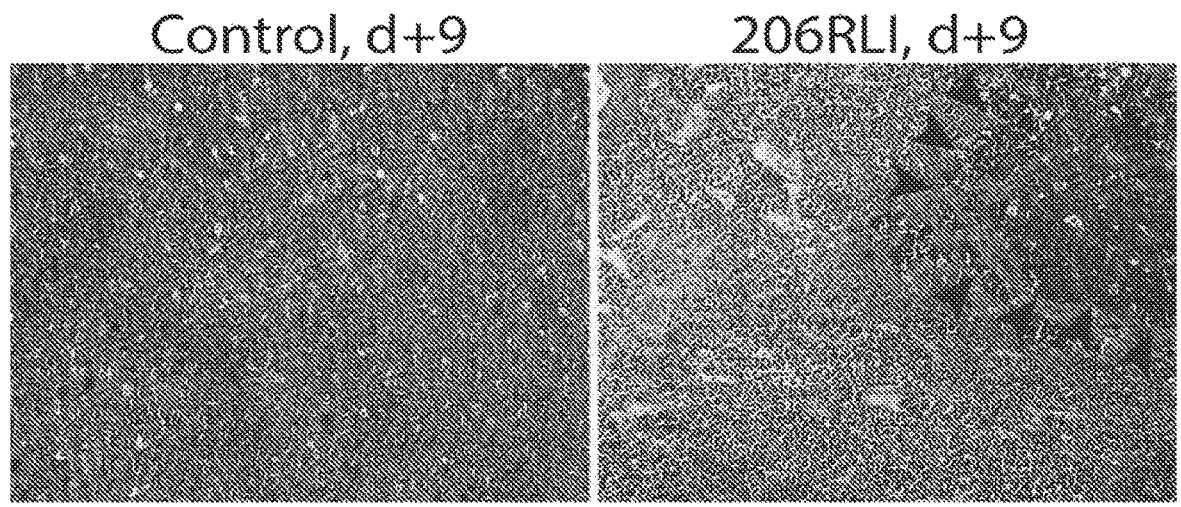
FIG. 3B. By day +10, the tumor bed is reduced to a dense scar tissue in the majority of the mice.

By day +10, the tumor bed was reduced to a dense scar tissue in the majority of the mice (FIG. 3B). In accordance with these observation, histochemical examination of the tumor site on day +10 after initiation of treatment revealed the formation of massive inflammatory infiltrates within the tumor bed after treatment, with tumor cells limited to small, encapsulated areas.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A fusion protein comprising an IL-15 polypeptide fused to an antigen binding protein wherein said fusion protein is encoded by the nucleic acid sequence SEQ ID NO: 1.

2. The fusion protein of claim 1, wherein said antigen binding protein specifically binds to said CD206.

\* \* \* \* \*

SEQUENCE LISTING

```
<160> NUMBER OF SEQ ID NOS: 201

<210> SEQ ID NO 1
<211> LENGTH: 1047
<212> TYPE: DNA
<213> ORGANISM: Artificial Sequence
<220> FEATURE:
<223> OTHER INFORMATION: synthetic

<400> SEQUENCE: 1
atggcccagg ttcagctgca agagagcggt gggggcctgg tacagccggg cgggagcttg      60
cgcctgtcct gtgcggcatc aggtaatatc ttttcaatta acgcgattgg atggtaccgc     120 caagcccgg ggaaacagcg tgagctggtg gccaccatta ccctctcagg ttccaccaac     180
```

```
tacgctgatt ctgtcaaagg gcgctttagc atttcacgcg acaatgcaaa aaataccgtg      240
tacctgcaaa tgaattctct taaaccagaa gacactgccg tctattattg caacgcgaac      300
acatattcgg acagtgacgt gtatggttat tggggacagg gtacgcaggt caccgtctcg      360
agcgcacacc atagtgaaga tccctcgtcc aaagccccca aagcaccgat ggcaatcaca      420
tgcccgccgc cgatgtcagt cgaacatgcg gacatttggg tcaaaagcta ctccttatac      480
agtcgcgagc gttatatctg caactccggc ttcaagcgca aagcgggcac cagttctctg      540
acggaatgtg tactgaataa agctacaaat gtggctcact ggacgacccc tagcctgaaa      600
tgtattcgcg acccggccct ggtacatcag cgtccggcgc cgccgtcagg ggggtccggt      660
ggcggaggct ccggggagg atctggcggg ggaggtagct acaaaattg ggtcaacgtt       720 atcagcgatc tgaagaaaat tgaagactta attcagagca tgcacatcga cgccaccctg      780
tacacggaaa gcgatgtgca cccatcctgt aaagtcacag ccatgaaatg ctttctcttg      840
gaacttcagg taattagcct ggaatccggt gatgcaagca ttcatgatac ggtcgaaaat      900
ttgattattc ttgcgaacaa ttctctgtcc agtaatggga cgtcacgga aagcggctgt      960 aaggagtgcg aagaactgga ggagaaaaac attaagaat ttctgcagag cttcgtgcat      1020
atcgtgcaga tgttcatcaa cacatca                                         1047
```

<210> SEQ ID NO 2
<211> LENGTH: 349
<212> TYPE: PRT
<213> ORGANISM: Artificial Sequence
<220> FEATURE:
<223> OTHER INFORMATION: synthetic

<400> SEQUENCE: 2

```
Met Ala Gln Val Gln Leu Gln Glu Ser Gly Gly Gly Leu Val Gln Pro
 1               5                  10                  15

Gly Gly Ser Leu Arg Leu Ser Cys Ala Ala Ser Gly Asn Ile Phe Ser
            20                  25                  30

Ile Asn Ala Ile Gly Trp Tyr Arg Gln Ala Pro Gly Lys Gln Arg Glu
        35                  40                  45

Leu Val Ala Thr Ile Thr Leu Ser Gly Ser Thr Asn Tyr Ala Asp Ser
    50                  55                  60

Val Lys Gly Arg Phe Ser Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Ala Asn Thr Tyr Ser Asp Ser Asp Val Tyr Gly Tyr Trp Gly
            100                 105                 110

Gln Gly Thr Gln Val Thr Val Ser Ser Ala His His Ser Glu Asp Pro
        115                 120                 125

Ser Ser Lys Ala Pro Lys Ala Pro Met Ala Ile Thr Cys Pro Pro Pro
    130                 135                 140

Met Ser Val Glu His Ala Asp Ile Trp Val Lys Ser Tyr Ser Leu Tyr
145                 150                 155                 160

Ser Arg Glu Arg Tyr Ile Cys Asn Ser Gly Phe Lys Arg Lys Ala Gly
                165                 170                 175

Thr Ser Ser Leu Thr Glu Cys Val Leu Asn Lys Ala Thr Asn Val Ala
            180                 185                 190

His Trp Thr Thr Pro Ser Leu Lys Cys Ile Arg Asp Pro Ala Leu Val
        195                 200                 205
```

His Gln Arg Pro Ala Pro Pro Ser Gly Gly Ser Gly Gly Gly Ser
    210                 215                 220

Gly Gly Gly Ser Gly Gly Gly Gly Ser Leu Gln Asn Trp Val Asn Val
225                 230                 235                 240

Ile Ser Asp Leu Lys Lys Ile Glu Asp Leu Ile Gln Ser Met His Ile
                245                 250                 255

Asp Ala Thr Leu Tyr Thr Glu Ser Asp Val His Pro Ser Cys Lys Val
            260                 265                 270

Thr Ala Met Lys Cys Phe Leu Leu Glu Leu Gln Val Ile Ser Leu Glu
        275                 280                 285

Ser Gly Asp Ala Ser Ile His Asp Thr Val Glu Asn Leu Ile Ile Leu
    290                 295                 300

Ala Asn Asn Ser Leu Ser Ser Asn Gly Asn Val Thr Glu Ser Gly Cys
305                 310                 315                 320

Lys Glu Cys Glu Glu Leu Glu Glu Lys Asn Ile Lys Glu Phe Leu Gln
                325                 330                 335

Ser Phe Val His Ile Val Gln Met Phe Ile Asn Thr Ser
            340                 345

<210> SEQ ID NO 3
<211> LENGTH: 249
<212> TYPE: DNA
<213> ORGANISM: Artificial Sequence
<220> FEATURE:
<223> OTHER INFORMATION: synthetic

<400> SEQUENCE: 3
atggcccagg ttcagctgca agagagcggt gggggcctgg tacagccggg cgggagcttg      60
cgcctgtcct gtgcggcatc aggtaatatc ttttcaatta cgcgattgg atggtaccgc     120 caagccccgg ggaaacagcg tgagctggtg ccaccattac cctctcagg ttccaccaac     180 tacgctgatt ctgtcaaagg cgctttagc atttcacgcg acaatgcaaa aaataccgtg     240
tacctgcaa                                                            249

<210> SEQ ID NO 4
<211> LENGTH: 156
<212> TYPE: DNA
<213> ORGANISM: Artificial Sequence
<220> FEATURE:
<223> OTHER INFORMATION: synthetic

<400> SEQUENCE: 4
atgaattctc ttaaaccaga agacactgcc gtctattatt gcaacgcgaa cacatattcg      60
gacagtgacg tgtatggtta ttggggacag ggtacgcagg tcaccgtctc gagcgcacac     120
catagtgaag atccctcgtc caagccccc aaagca                                156

<210> SEQ ID NO 5
<211> LENGTH: 240
<212> TYPE: DNA
<213> ORGANISM: Artificial Sequence
<220> FEATURE:
<223> OTHER INFORMATION: synthetic

<400> SEQUENCE: 5
ccgatggcaa tcacatgccc gccgccgatg tcagtcgaac atgcggacat ttgggtcaaa      60
agctactcct atacagtcg cgagcgttat atctgcaact ccggcttcaa gcgcaaagcg     120
ggcaccagtt ctctgacgga atgtgtactg aataaagcta caaatgtggc tcactggacg     180

```
                                                              -continued
accccctagcc tgaaatgtat tcgcgacccg gccctggtac atcagcgtcc ggcgccgccg    240
```

<210> SEQ ID NO 6
<211> LENGTH: 60
<212> TYPE: DNA
<213> ORGANISM: Artificial Sequence
<220> FEATURE:
<223> OTHER INFORMATION: synthetic

<400> SEQUENCE: 6

```
tcaggggggt ccggtggcgg aggctccggg ggaggatctg gcggggggagg tagcttacaa    60
```

<210> SEQ ID NO 7
<211> LENGTH: 346
<212> TYPE: DNA
<213> ORGANISM: Artificial Sequence
<220> FEATURE:
<223> OTHER INFORMATION: synthetic

<400> SEQUENCE: 7

```
aattgggtca acgttatcag cgatctgaag aaaattgaag acttaattca gagcatgcac    60
atcgacgcca ccctgtacac ggaaagcgat gtgcacccat cctgtaaagt cacagccatg   120
aaatgctttc tcttggaact tcaggtaatt agcctggaat ccggtgatgc aagcattcat   180
gatacggtcg aaaatttgat tattcttgcg aacaattctc tgtccagtaa tgggaacgtc   240
acggaaagcg gctgtaagga gtgcgaagaa ctggaggaga aaacattaa agaatttctg    300
cagagcttcg tgcatatcgt gcagatgttc atcaacacat cataat                  346
```

<210> SEQ ID NO 8
<211> LENGTH: 351
<212> TYPE: DNA
<213> ORGANISM: Artificial Sequence
<220> FEATURE:
<223> OTHER INFORMATION: synthetic

<400> SEQUENCE: 8

```
atggcaaact gggtgaacgt tatcagcgac ctgaagaaaa tcgaggatct gattcagagc    60
atgcacattg acgcgaccct gtacaccgaa agcgatgtgc acccgagctg caaggttacc   120
gcgatgaaat gcttcctgct ggagctgcaa gtgatcagcc tggaaagcgg tgacgcgagc   180
attcacgata ccgttgagaa cctgatcatt ctggcgaaca acagcctgag cagcaacggt   240
aacgtgaccg agagcggctg caaggaatgc gaggaactgg aggaaaagaa catcaaagaa   300
ttcctgcaga gctttgtgca catcgttcaa atgtttatta acaccagcga g             351
```

<210> SEQ ID NO 9
<211> LENGTH: 117
<212> TYPE: PRT
<213> ORGANISM: Artificial Sequence
<220> FEATURE:
<223> OTHER INFORMATION: synthetic

<400> SEQUENCE: 9

```
Met Ala Asn Trp Val Asn Val Ile Ser Asp Leu Lys Lys Ile Glu Asp
1               5                   10                  15

Leu Ile Gln Ser Met His Ile Asp Ala Thr Leu Tyr Thr Glu Ser Asp
            20                  25                  30

Val His Pro Ser Cys Lys Val Thr Ala Met Lys Cys Phe Leu Leu Glu
        35                  40                  45

Leu Gln Val Ile Ser Leu Glu Ser Gly Asp Ala Ser Ile His Asp Thr
    50                  55                  60
```

Val Glu Asn Leu Ile Ile Leu Ala Asn Asn Ser Leu Ser Ser Asn Gly
65                  70                  75                  80

Asn Val Thr Glu Ser Gly Cys Lys Glu Cys Glu Leu Glu Glu Lys
                85                  90                  95

Asn Ile Lys Glu Phe Leu Gln Ser Phe Val His Ile Val Gln Met Phe
            100                 105                 110

Ile Asn Thr Ser Glu
            115

<210> SEQ ID NO 10
<211> LENGTH: 261
<212> TYPE: DNA
<213> ORGANISM: Artificial Sequence
<220> FEATURE:
<223> OTHER INFORMATION: synthetic

<400> SEQUENCE: 10
atggcccagg tgcagctggt ggagtccgga ggtggatcgg ttcaggcagg gggcagcctc    60
cgtctgtctt gcacagcgag cggcggtagc gaatacagct actccacctt cagtttaggc   120
tggttccggc aggcaccggg tcaagaacgc gaagccgtag cggcaattgc cagcatggga   180
ggtttgacct attacgctga ctcggtcaaa gggcgcttca caattagccg tgacaacgca   240
aagaatacgg taacccttca g                                             261

<210> SEQ ID NO 11
<211> LENGTH: 86
<212> TYPE: PRT
<213> ORGANISM: Artificial Sequence
<220> FEATURE:
<223> OTHER INFORMATION: synthetic

<400> SEQUENCE: 11

Met Ala Gln Val Gln Leu Val Glu Ser Gly Gly Gly Ser Val Gln Ala
1               5                   10                  15

Gly Gly Ser Leu Arg Leu Ser Cys Thr Ala Ser Gly Gly Ser Glu Tyr
            20                  25                  30

Ser Tyr Ser Thr Phe Ser Leu Gly Trp Phe Arg Gln Ala Pro Gly Gln
        35                  40                  45

Glu Arg Glu Ala Val Ala Ala Ile Ala Ser Met Gly Gly Leu Thr Tyr
    50                  55                  60

Tyr Ala Asp Ser Val Lys Gly Arg Phe Thr Ile Ser Arg Asp Asn Ala
65                  70                  75                  80

Lys Asn Thr Val Thr Leu
            85

<210> SEQ ID NO 12
<211> LENGTH: 507
<212> TYPE: DNA
<213> ORGANISM: Artificial Sequence
<220> FEATURE:
<223> OTHER INFORMATION: synthetic

<400> SEQUENCE: 12
atggcatgcg acctgccgca gacccacaac ctgcgtaaca gcgtgcgct gaccctgctg     60 gtgcaaatgc gtcgtctgag cccgctgagc tgcctgaagg accgtaaaga tttcggtttt   120
ccgcaggaga aggtggacgc gcagcaaatc aagaaagcgc aagcgattcc ggttctgagc   180
gaactgaccc agcaaatcct gaacattttc accagcaaag atagcagcgc ggcgtggaac   240

```
accaccctgc tggacagctt ttgcaacgat ctgcaccagc aactgaacga cctgcagggt    300
tgcctgatgc agcaagtggg cgttcaggag ttcccgctga cccaagaaga tgcgctgctg    360
gcggtgcgta agtactttca ccgtatcacc gtttatctgc gtgagaagaa acacagcccg    420
tgcgcgtggg aagtggttcg tgcggaagtg tggcgtgcgc tgagcagcag cgcgaacgtt    480
ctgggccgtc tgcgtgagga aaaagag                                       507
```

```
<210> SEQ ID NO 13
<211> LENGTH: 169
<212> TYPE: PRT
<213> ORGANISM: Artificial Sequence
<220> FEATURE:
<223> OTHER INFORMATION: synthetic

<400> SEQUENCE: 13
```

Met Ala Cys Asp Leu Pro Gln Thr His Asn Leu Arg Asn Lys Arg Ala
1               5                   10                  15

Leu Thr Leu Leu Val Gln Met Arg Arg Leu Ser Pro Leu Ser Cys Leu
            20                  25                  30

Lys Asp Arg Lys Asp Phe Gly Phe Pro Gln Glu Lys Val Asp Ala Gln
        35                  40                  45

Gln Ile Lys Lys Ala Gln Ala Ile Pro Val Leu Ser Glu Leu Thr Gln
    50                  55                  60

Gln Ile Leu Asn Ile Phe Thr Ser Lys Asp Ser Ser Ala Ala Trp Asn
65                  70                  75                  80

Thr Thr Leu Leu Asp Ser Phe Cys Asn Asp Leu His Gln Gln Leu Asn
                85                  90                  95

Asp Leu Gln Gly Cys Leu Met Gln Gln Val Gly Val Gln Glu Phe Pro
            100                 105                 110

Leu Thr Gln Glu Asp Ala Leu Leu Ala Val Arg Lys Tyr Phe His Arg
        115                 120                 125

Ile Thr Val Tyr Leu Arg Glu Lys Lys His Ser Pro Cys Ala Trp Glu
    130                 135                 140

Val Val Arg Ala Glu Val Trp Arg Ala Leu Ser Ser Ser Ala Asn Val
145                 150                 155                 160

Leu Gly Arg Leu Arg Glu Glu Lys Glu
                165

```
<210> SEQ ID NO 14
<211> LENGTH: 381
<212> TYPE: DNA
<213> ORGANISM: Artificial Sequence
<220> FEATURE:
<223> OTHER INFORMATION: synthetic

<400> SEQUENCE: 14
atggcacagg gtccggaccg tctgctgatc cgtctgcgtc acctgatcga tattgtggag    60
caactgaaaa tttacgaaaa cgacctggat ccggagctgc tgagcgcgcc gcaggacgtt   120
aagggtcact gcgaacacgc ggcgttcgcg tgctttcaaa aggcgaaact gaagccgagc   180
aacccgggca caacaaaaac cttcatcatt gacctggttg cgcagctgcg tcgtcgtctg   240
ccggcgcgtc gtggtggcaa gaaacaaaaa cacatcgcga gtgcccgag ctgcgatagc   300 tatgagaaac gtaccccgaa ggagtttctg aacgtctga aatggctgct gcagaagatg   360
attcaccaac acctgagcga g                                             381
```

```
<210> SEQ ID NO 15
```

<211> LENGTH: 127
<212> TYPE: PRT
<213> ORGANISM: Artificial Sequence
<220> FEATURE:
<223> OTHER INFORMATION: synthetic

<400> SEQUENCE: 15

```
Met Ala Gln Gly Pro Asp Arg Leu Leu Ile Arg Leu Arg His Leu Ile
1               5                   10                  15

Asp Ile Val Glu Gln Leu Lys Ile Tyr Glu Asn Asp Leu Asp Pro Glu
            20                  25                  30

Leu Leu Ser Ala Pro Gln Asp Val Lys Gly His Cys Glu His Ala Ala
        35                  40                  45

Phe Ala Cys Phe Gln Lys Ala Lys Leu Lys Pro Ser Asn Pro Gly Asn
    50                  55                  60

Asn Lys Thr Phe Ile Ile Asp Leu Val Ala Gln Leu Arg Arg Arg Leu
65                  70                  75                  80

Pro Ala Arg Arg Gly Gly Lys Lys Gln Lys His Ile Ala Lys Cys Pro
                85                  90                  95

Ser Cys Asp Ser Tyr Glu Lys Arg Thr Pro Lys Glu Phe Leu Glu Arg
            100                 105                 110

Leu Lys Trp Leu Leu Gln Lys Met Ile His Gln His Leu Ser Glu
        115                 120                 125
```

<210> SEQ ID NO 16
<211> LENGTH: 390
<212> TYPE: DNA
<213> ORGANISM: Artificial Sequence
<220> FEATURE:
<223> OTHER INFORMATION: synthetic

<400> SEQUENCE: 16

```
atggcacaca aaagcagccc gcagggtccg gaccgtctgc tgatccgtct cgtcacctg      60
atcgatattg tggagcaact gaaaatttac gaaaacgacc tggatccgga gctgctgagc    120
gcgccgcagg acgttaaggg tcactgcgaa cacgcggcgt tcgcgtgctt tcaaaaggcg    180
aaactgaagc cgagcaaccc gggcaacaac aagaccttca tcattgacct ggttgcgcag    240
ctgcgtcgtc gtctgccggc gcgtcgtggt ggcaagaaac aaaaacacat cgcgaagtgc    300
ccgagctgcg atagctatga aaacgtaccc ccgaaggagt ttctggaacg tctgaaatgg    360
ctgctgcaga agatgattca ccaacacctg                                    390
```

<210> SEQ ID NO 17
<211> LENGTH: 130
<212> TYPE: PRT
<213> ORGANISM: Artificial Sequence
<220> FEATURE:
<223> OTHER INFORMATION: synthetic

<400> SEQUENCE: 17

```
Met Ala His Lys Ser Ser Pro Gln Gly Pro Asp Arg Leu Leu Ile Arg
1               5                   10                  15

Leu Arg His Leu Ile Asp Ile Val Glu Gln Leu Lys Ile Tyr Glu Asn
            20                  25                  30

Asp Leu Asp Pro Glu Leu Leu Ser Ala Pro Gln Asp Val Lys Gly His
        35                  40                  45

Cys Glu His Ala Ala Phe Ala Cys Phe Gln Lys Ala Lys Leu Lys Pro
    50                  55                  60

Ser Asn Pro Gly Asn Asn Lys Thr Phe Ile Ile Asp Leu Val Ala Gln
```

```
            65                  70                  75                  80
Leu Arg Arg Arg Leu Pro Ala Arg Arg Gly Gly Lys Lys Gln Lys His
                85                  90                  95

Ile Ala Lys Cys Pro Ser Cys Asp Ser Tyr Glu Lys Arg Thr Pro Lys
            100                 105                 110

Glu Phe Leu Glu Arg Leu Lys Trp Leu Leu Gln Lys Met Ile His Gln
        115                 120                 125

His Leu
    130

<210> SEQ ID NO 18
<211> LENGTH: 465
<212> TYPE: DNA
<213> ORGANISM: Artificial Sequence
<220> FEATURE:
<223> OTHER INFORMATION: synthetic

<400> SEQUENCE: 18
atggcagact gcgatatcga gggcaaggac ggcaaacagt acgaaagcgt gctgatggtt      60
agcatcgacc aactgctgga tagcatgaag gagattggta gcaactgcct gaacaacgaa     120
ttcaacttct ttaagcgtca catttgcgat gcgaacaaag agggcatgtt cctgtttcgt     180
gcggcgcgta agctgcgtca gttcctgaaa atgaacagca ccggtgactt tgatctgcac     240
ctgctgaagg tgagcgaagg caccaccatc ctgctgaact gcaccggtca ggttaaaggt     300
cgtaaaccgg cggcgctggg cgaggcgcaa ccgaccaaaa gcctggagga aaacaagagc     360
ctgaaagaac agaagaaact gaacgacctg tgctttctga gcgtctgctg caagagatc      420 aagacctgct ggaacaaaat tctgatgggc accaagaac acgag                      465

<210> SEQ ID NO 19
<211> LENGTH: 155
<212> TYPE: PRT
<213> ORGANISM: Artificial Sequence
<220> FEATURE:
<223> OTHER INFORMATION: synthetic

<400> SEQUENCE: 19

Met Ala Asp Cys Asp Ile Glu Gly Lys Asp Gly Lys Gln Tyr Glu Ser
1               5                   10                  15

Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
        35                  40                  45

Cys Asp Ala Asn Lys Glu Gly Met Phe Leu Phe Arg Ala Ala Arg Lys
    50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
            100                 105                 110

Lys Ser Leu Glu Glu Asn Lys Ser Leu Lys Glu Gln Lys Lys Leu Asn
        115                 120                 125

Asp Leu Cys Phe Leu Lys Arg Leu Leu Gln Glu Ile Lys Thr Cys Trp
    130                 135                 140

Asn Lys Ile Leu Met Gly Thr Lys Glu His Glu
145                 150                 155
```

<210> SEQ ID NO 20
<211> LENGTH: 480
<212> TYPE: DNA
<213> ORGANISM: Artificial Sequence
<220> FEATURE:
<223> OTHER INFORMATION: synthetic

<400> SEQUENCE: 20

```
atggcagtgc gtagcagcag ccgtaccccg agcgacaagc cggttgcgca tgtggttgcg      60
aacccgcagg cggagggtca gctgcaatgg ctgaaccgtc gtgcgaacgc gctgctggcg     120
aacggtgtgg aactgcgtga taaccaactg gtggttccga gcgagggcct gtacctgatc     180
tatagccagg tgctgttcaa aggtcaaggc tgcccgagca cccacgttct gctgacccac     240
accatcagcc gtattgcggt gagctaccag accaaggtta acctgctgag cgcgattaaa     300
agcccgtgcc aacgtgaaac cccggagggt gcggaggcga agccgtggta cgaaccgatc     360
tatctgggtg gcgtgtttca gctggaaaaa ggcgaccgtc tgagcgcgga gattaaccgt     420
ccggactacc tggatttcgc ggagagcggt caagtttatt ttggcatcat tgcgctggag     480
```

<210> SEQ ID NO 21
<211> LENGTH: 160
<212> TYPE: PRT
<213> ORGANISM: Artificial Sequence
<220> FEATURE:
<223> OTHER INFORMATION: synthetic

<400> SEQUENCE: 21

```
Met Ala Val Arg Ser Ser Ser Arg Thr Pro Ser Asp Lys Pro Val Ala
1               5                   10                  15

His Val Val Ala Asn Pro Gln Ala Glu Gly Gln Leu Gln Trp Leu Asn
            20                  25                  30

Arg Arg Ala Asn Ala Leu Leu Ala Asn Gly Val Glu Leu Arg Asp Asn
        35                  40                  45

Gln Leu Val Val Pro Ser Glu Gly Leu Tyr Leu Ile Tyr Ser Gln Val
    50                  55                  60

Leu Phe Lys Gly Gln Gly Cys Pro Ser Thr His Val Leu Leu Thr His
65                  70                  75                  80

Thr Ile Ser Arg Ile Ala Val Ser Tyr Gln Thr Lys Val Asn Leu Leu
                85                  90                  95

Ser Ala Ile Lys Ser Pro Cys Gln Arg Glu Thr Pro Glu Gly Ala Glu
            100                 105                 110

Ala Lys Pro Trp Tyr Glu Pro Ile Tyr Leu Gly Gly Val Phe Gln Leu
        115                 120                 125

Glu Lys Gly Asp Arg Leu Ser Ala Glu Ile Asn Arg Pro Asp Tyr Leu
    130                 135                 140

Asp Phe Ala Glu Ser Gly Gln Val Tyr Phe Gly Ile Ile Ala Leu Glu
145                 150                 155                 160
```

<210> SEQ ID NO 22
<211> LENGTH: 408
<212> TYPE: PRT
<213> ORGANISM: Artificial Sequence
<220> FEATURE:
<223> OTHER INFORMATION: synthetic

<400> SEQUENCE: 22

```
Ala Thr Gly Gly Cys Ala Gly Cys Gly Cys Gly Ala Cys Cys Ala
1               5                   10                  15
```

Gly Cys Ala Gly Cys Ala Gly Cys Ala Cys Ala Gly Ala Ala
            20                  25                  30

Ala Ala Cys Cys Ala Gly Cys Thr Gly Cys Ala Ala Cys Thr Gly
        35                  40                  45

Gly Ala Ala Cys Ala Cys Cys Thr Gly Cys Thr Gly Cys Thr Gly Gly
    50                  55                  60

Ala Cys Cys Thr Gly Cys Ala Gly Ala Thr Gly Ala Thr Thr Cys Thr
65                  70                  75                  80

Gly Ala Ala Cys Gly Gly Thr Ala Thr Cys Ala Ala Cys Ala Ala Cys
                85                  90                  95

Thr Ala Cys Ala Ala Gly Ala Ala Cys Cys Gly Ala Ala Cys
            100                 105                 110

Thr Gly Ala Cys Cys Gly Thr Ala Th

```
<212> TYPE: PRT
<213> ORGANISM: Artificial Sequence
<220> FEATURE:
<223> OTHER INFORMATION: synthetic

<400> SEQUENCE: 23

Met Ala Ala Pro Thr Ser Ser Ser Thr Lys Lys Thr Gln Leu Gln Leu
1               5                   10                  15

Glu His Leu Leu Leu Asp Leu Gln Met Ile Leu Asn Gly Ile Asn Asn
            20                  25                  30

Tyr Lys Asn Pro Lys Leu Thr Arg Met Leu Thr Phe Lys Phe Tyr Met
        35                  40                  45

Pro Lys Lys Ala Thr Glu Leu Lys His Leu Gln Cys Leu Glu Glu Glu
    50                  55                  60

Leu Lys Pro Leu Glu Glu Val Leu Asn Leu Ala Gln Ser Lys Asn Phe
65                  70                  75                  80

His Leu Arg Pro Arg Asp Leu Ile Ser Asn Ile Asn Val Ile Val Leu
                85                  90                  95

Glu Leu Lys Gly Ser Glu Thr Thr Phe Met Cys Glu Tyr Ala Asp Glu
            100                 105                 110

Thr Ala Thr Ile Val Glu Phe Leu Asn Arg Trp Ile Thr Phe Cys Gln
        115                 120                 125

Ser Ile Ile Ser Thr Leu Thr Glu
    130                 135

<210> SEQ ID NO 24
<211> LENGTH: 408
<212> TYPE: PRT
<213> ORGANISM: Artificial Sequence
<220> FEATURE:
<223> OTHER INFORMATION: synthetic

<400> SEQUENCE: 24

Ala Thr Gly Gly Cys Ala Gly Cys Cys Gly Ala Cys Cys Ala
1               5                   10                  15

Gly Cys Ala Gly Cys Ala Gly Cys Ala Cys Cys Ala Gly Ala Ala
            20                  25                  30

Ala Ala Cys Cys Cys Ala Gly Cys Thr Gly Cys Ala Ala Cys Thr Gly
        35                  40                  45

Gly Ala Ala Cys Ala Cys Cys Thr Gly Cys Thr Gly Cys Thr Gly Gly
    50                  55                  60

Ala Cys Cys Thr Gly Cys Ala Gly Ala Thr Gly Ala Thr Thr Cys Thr
65                  70                  75                  80

Gly Ala Ala Cys Gly Gly Thr Ala Thr Cys Ala Ala Cys Ala Ala Cys
                85                  90                  95

Thr Ala Cys Ala Ala Gly Ala Ala Cys Cys Cys Gly Ala Ala Ala Cys
            100                 105                 110

Thr Gly Ala Cys Cys Cys Gly Thr Ala Thr Gly Cys Thr Gly Ala Cys
        115                 120                 125

Cys Thr Thr Cys Ala Ala Gly Thr Thr Thr Thr Ala Thr Ala Thr Gly
    130                 135                 140

Cys Cys Gly Ala Ala Gly Ala Ala Ala Gly Cys Gly Ala Cys Cys Gly
145                 150                 155                 160

Ala Gly Cys Thr Gly Ala Ala Gly Cys Ala Cys Thr Gly Cys Ala
                165                 170                 175

Gly Thr Gly Cys Cys Thr Gly Gly Ala Gly Gly Ala Ala Gly Ala Gly
            180                 185                 190
```

Cys Thr Gly Ala Ala Cys Cys Gly Cys Thr Gly Ala Ala Gly
            195                 200                 205

Ala Gly Gly Thr Gly Cys Thr Gly Ala Ala Cys Thr Gly Gly Cys
210                 215                 220

Gly Cys Ala Ala Gly Cys Ala Ala Gly Ala Ala Cys Thr Thr Cys
225                 230                 235                 240

Cys Ala Cys Cys Thr Gly Cys Gly Thr Cys Cys Gly Cys Gly Thr
                245                 250                 255

Ala Cys Cys Thr Gly Ala Thr Cys Ala Gly Cys Ala Ala Cys Ala
            260                 265                 270

Thr Ala Ala Cys Gly Thr Gly Ala Thr Cys Gly Thr Thr Cys Thr Gly
        275                 280                 285

Gly Ala Ala Cys Thr Gly Ala Ala Ala Gly Gly Cys Ala Gly Cys Gly
    290                 295                 300

Ala Ala Ala Cys Cys Ala Cys Cys Thr Thr Cys Ala Thr Gly Thr Gly
305                 310                 315                 320

Cys Gly Ala Ala Thr Ala Cys Gly Cys Cys Gly Ala Thr Gly Ala Ala
                325                 330                 335

Ala Cys Cys Gly Cys Gly Ala Cys Cys Ala Thr Cys Gly Thr Thr Gly
            340                 345                 350

Ala Ala Thr Thr Cys Cys Thr Gly Ala Ala Cys Cys Gly Thr Thr Gly
        355                 360                 365

Gly Ala Thr Cys Ala Cys Cys Thr Thr Cys G

-continued

<210> SEQ ID NO 26
<211> LENGTH: 618
<212> TYPE: PRT
<213> ORGANISM: Artificial Sequence
<220> FEATURE:
<223> OTHER INFORMATION: synthetic

<400> SEQUENCE: 26

```
Thr Thr Cys Cys Cys Gly Ala Cys Cys Gly Ala Thr Cys Cys Gly Cys
1               5                   10                  15

Thr Gly Ala Gly Cys Cys Thr Gly Cys Ala Ala Gly Ala Ala Cys Thr
            20                  25                  30

Gly Cys Gly Thr Cys Gly Thr Gly Ala Ala Thr Thr Thr Ala Cys Cys
        35                  40                  45

Gly Thr Thr Ala Gly Cys Cys Thr Gly Thr Ala Thr Cys Thr Gly Gly
    50                  55                  60

Cys Gly Cys Gly Thr Ala Ala Gly Cys Thr Gly Cys Thr Gly Ala Gly
65                  70                  75                  80

Cys Gly Ala Ala Gly Thr Gly Cys Ala Gly Gly Gly Thr Thr Ala Cys
                85                  90                  95

Gly Thr Thr Cys Ala Cys Ala Gly Cys Thr Thr Cys Gly Cys Gly Gly
            100                 105                 110

Ala Ala Ala Gly Cys Cys Gly Thr Cys Thr Gly Cys Cys Gly Gly Gly
        115                 120                 125

Thr Gly Thr Thr Ala Ala Cys Cys Thr Gly Gly Ala Thr Cys Thr Gly
    130                 135                 140

Cys Thr Gly Cys Cys Gly Cys Thr Gly Gly Gly Thr Thr Ala Thr Cys
145                 150                 155                 160

Ala Cys Cys Thr Gly Cys Cys Gly Ala Ala Cys Gly Thr Thr Ala Gly
                165                 170                 175

Cys Cys Thr Gly Ala Cys Cys Thr Thr Thr Cys Ala Gly Gly Cys Gly
            180                 185                 190

Thr Gly Gly Cys Ala Cys Cys Ala Cys Cys Thr Gly Ala Gly Cys Gly
        195                 200                 205

Ala Thr Ala Gly Cys Gly Ala Ala Cys Gly Thr Cys Thr Gly Thr Gly
    210                 215                 220

Cys Thr Thr Thr Cys Thr Gly Gly Cys Gly Ala Cys Cys Ala Cys Cys
225                 230                 235                 240

Cys Thr Gly Cys Gly Thr Cys Cys Gly Thr Thr Cys Cys Cys Gly Gly
                245                 250                 255

Cys Gly Ala Thr Gly Cys Thr Gly Gly Gly Thr Gly Gly Cys Cys Thr
            260                 265                 270

Gly Gly Gly Thr Ala Cys Cys Cys Ala Ala Gly Gly Thr Ala Cys Cys
        275                 280                 285

Thr Gly Gly Ala Cys Cys Ala Gly Cys Ala Gly Cys Gly Ala Gly Cys
    290                 295                 300

Gly Thr Gly Ala Ala Cys Ala Gly Cys Thr Gly Thr Gly Gly Gly Cys
305                 310                 315                 320

Gly Ala Thr Gly Cys Gly Thr Cys Thr Gly Gly Ala Thr Cys Thr Gly
                325                 330                 335

Cys Gly Thr Gly Ala Cys Cys Thr Gly Cys Ala Cys Cys Gly Thr Cys
            340                 345                 350

Ala Cys Cys Thr Gly Cys Gly Thr Thr Thr Cys Cys Ala Gly Gly Thr
        355                 360                 365
```

```
Thr Cys Thr Gly Gly Cys Gly Gly Cys Gly Gly Cys Thr Thr Cys
    370                 375                 380

Ala Ala Gly Thr Gly Cys Ala Gly Cys Ala Ala Gly Ala Gly Gly
385                 390                 395                 400

Ala Ala Gly Ala Gly Gly Ala Cys Ala Ala Gly Ala Ala Gly Ala
                405                 410                 415

Gly Gly Ala Ala Gly Ala Gly Gly Ala Ala Gly Ala Ala Gly Ala
            420                 425                 430

Gly Ala Gly Gly Ala Ala Gly Ala Gly Ala Ala Gly Ala Ala Cys
        435                 440                 445

Thr Gly Cys Cys Gly Cys Thr Gly Gly Cys Gly Cys Gly Cys Thr
    450                 455                 460

Gly Gly Gly Thr Gly Gly Cys Cys Cys Gly Ala Ala Cys Cys Ala Ala
465                 470                 475                 480

Gly Thr Thr Ala Gly Cys Ala Gly Cys Ala Ala Gly Thr Thr Ala
                485                 490                 495

Gly Cys Thr Gly Gly Cys Cys Gly Cys Ala Gly Cys Thr Gly Cys Thr
                    500                 505                 510

Gly Thr Ala Thr Ala Cys Cys Thr Ala Cys Cys Ala Gly Cys Thr Gly
        515                 520                 525

Cys Thr Gly Cys Ala Cys Ala Gly Cys Cys Thr Gly Gly Ala Ala Cys
    530                 535                 540

Thr Gly Gly Thr Thr Cys Thr Gly Ala Gly Cys Cys Gly Thr Gly Cys
545                 550                 555                 560

Gly Gly Thr Thr Cys Gly Thr Gly Ala Cys Thr Gly Cys Thr Gly
                565                 570                 575

Cys Thr Gly Cys Thr Gly Ala Cys Cys Thr Gly Cys Cys Gly Cys
            580                 585                 590

Gly Thr Cys Gly Thr Cys Gly Gly Thr Ala Gly Cys Gly Cys
        595                 600                 605

Gly Thr Gly Gly Gly Ala Thr Ala Gly Cys
    610                 615
```

<210> SEQ ID NO 27
<211> LENGTH: 206
<212> TYPE: PRT
<213> ORGANISM: Artificial Sequence
<220> FEATURE:
<223> OTHER INFORMATION: synthetic

<400> SEQUENCE: 27

```
Phe Pro Thr Asp Pro Leu Ser Leu Gln Glu Leu Arg Arg Glu Phe Thr
1               5                   10                  15

Val Ser Leu Tyr Leu Ala Arg Lys Leu Leu Ser Glu Val Gln Gly Tyr
            20                  25                  30

Val His Ser Phe Ala Glu Ser Arg Leu Pro Gly Val Asn Leu Asp Leu
        35                  40                  45

Leu Pro Leu Gly Tyr His Leu Pro Asn Val Ser Leu Thr Phe Gln Ala
    50                  55                  60

Trp His His Leu Ser Asp Ser Glu Arg Leu Cys Phe Leu Ala Thr Thr
65                  70                  75                  80

Leu Arg Pro Phe Pro Ala Met Leu Gly Gly Leu Gly Thr Gln Gly Thr
                85                  90                  95

Trp Thr Ser Ser Glu Arg Glu Gln Leu Trp Ala Met Arg Leu Asp Leu
            100                 105                 110
```

Arg Asp Leu His Arg His Leu Arg Phe Gln Val Leu Ala Ala Gly Phe
            115                 120                 125

Lys Cys Ser Lys Glu Glu Asp Lys Glu Glu Glu Glu Glu Glu Glu
            130                 135                 140

Glu Glu Glu Lys Lys Leu Pro Leu Gly Ala Leu Gly Gly Pro Asn Gln
145                 150                 155                 160

Val Ser Ser Gln Val Ser Trp Pro Gln Leu Leu Tyr Thr Tyr Gln Leu
                165                 170                 175

Leu His Ser Leu Glu Leu Val Leu Ser Arg Ala Val Arg Asp Leu Leu
            180                 185                 190

Leu Leu Ser Leu Pro Arg Arg Pro Gly Ser Ala Trp Asp Ser
            195                 200                 205

<210> SEQ ID NO 28
<211> LENGTH: 471
<212> TYPE: DNA
<213> ORGANISM: Artificial Sequence
<220> FEATURE:
<223> OTHER INFORMATION: synthetic

<400> SEQUENCE: 28
aacttcggtc gtctgcactg caccaccgcg gttatccgta atatcaatga ccaggttctg      60
ttcgtggaca gcgccagcc ggttttcgaa gatatgaccg acatcgatca gagcgcgagc     120
gaaccgcaaa cccgtctgat tatctacatg tataaggata gcgaagttcg tggtctggcg     180
gttaccctga gcgtgaaaga cagcaagatg agcaccctga gctgcaaaaa caagatcatt     240
agcttcgagg aaatggaccc gccggaaaac atcgacgata tccaaagcga cctgatcttc     300
tttcagaagc gtgttccggg tcacaacaag atggaattcg agagcagcct gtacgaaggt     360
cacttcctgg cgtgccagaa agaggacgat gcgtttaagc tgatcctgaa gaagaaagac     420
gagaatggcg acaagagcgt tatgttcacc ctgaccaacc tgcaccaaag c              471

<210> SEQ ID NO 29
<211> LENGTH: 157
<212> TYPE: PRT
<213> ORGANISM: Artificial Sequence
<220> FEATURE:
<223> OTHER INFORMATION: synthetic

<400> SEQUENCE: 29

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Lys Asp Glu Asn Gly Asp
    130                 135                 140
Lys Ser Val Met Phe Thr Leu Thr Asn Leu His Gln Ser
145                 150                 155

<210> SEQ ID NO 30
<211> LENGTH: 119
<212> TYPE: PRT
<213> ORGANISM: Artificial Sequence
<220> FEATURE:
<223> OTHER INFORMATION: synthetic

<400> SEQUENCE: 30

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Val Val Val Thr Thr Thr Pro Tyr Ser Asp Tyr Trp Gly Gln Gly
            100                 105                 110

Thr Leu Val Thr Val Ser Ser
        115

<210> SEQ ID NO 31
<211> LENGTH: 124
<212> TYPE: PRT
<213> ORGANISM: Artificial Sequence
<220> FEATURE:
<223> OTHER INFORMATION: synthetic

<400> SEQUENCE: 31

Gln Val Gln Leu Val Glu Ser Gly Gly Gly Leu Val Gln Ala Gly Gly
1               5                   10                  15

Ser Leu Arg Leu Ser Cys Ala Ala Ser Ala Arg Ile Phe Ser Ser Tyr
            20                  25                  30

His Lys Ala Trp Phe Arg Gln Ala Pro Gly Lys Glu Arg Glu Ile Val
        35                  40                  45

Ala Ala Val Asn Gly Gly Ser Ser Thr Tyr Val Ala Asp Ser Val
    50                  55                  60

Lys Gly Arg Phe Thr Ile Ser Gly Asp Asn Ala Leu Asn Thr Val Ser
65                  70                  75                  80

Leu Gln Met Asn Ser Leu Lys Pro Glu Asp Thr Ala Val Tyr Tyr Cys
                85                  90                  95

Ala Ala Ala Gly Arg Ala Gly Pro Leu Ala Ala Ser Tyr Arg Tyr Asp
            100                 105                 110

Tyr Trp Gly Gln Gly Thr Gln Val Thr Val Ser Ser
        115                 120

<210> SEQ ID NO 32
<211> LENGTH: 120
<212> TYPE: PRT
<213> ORGANISM: Artificial Sequence
<220> FEATURE:
<223> OTHER INFORMATION: synthetic

<400> SEQUENCE: 32

Gln Val Gln Leu Val Glu Ser Gly Gly Gly Leu Val Gln Ala Gly Gly
1               5                   10                  15

Ser Leu Arg Leu Ser Cys Ala Ala Ser Ala Arg Ile Phe Ser Ser Tyr
            20                  25                  30

His Lys Ala Trp Phe Arg Gln Ala Pro Gly Lys Glu Arg Glu Ile Val
        35                  40                  45

Ala Ala Val Asn Gly Gly Ser Ser Thr Tyr Val Ala Asp Ser Val
    50                  55                  60

Lys Gly Arg Phe Thr Ile Ser Gly Asp Asn Ala Leu Asn Thr Val Ser
65                  70                  75                  80

Leu Gln Met Asn Ser Leu Lys Pro Glu Asp Thr Ala Val Tyr Tyr Cys
                85                  90                  95

Lys Ala Val Val Val Thr Thr Thr Pro Tyr Ser Asp Tyr Trp Gly Gln
            100                 105                 110

Gly Thr Leu Val Thr Val Ser Ser
        115                 120

<210> SEQ ID NO 33
<211> LENGTH: 123
<212> TYPE: PRT
<213> ORGANISM: Artificial Sequence
<220> FEATURE:
<223> OTHER INFORMATION: synthetic

<400> SEQUENCE: 33

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ala Gly Arg Ala Gly Pro Leu Ala Ala Ser Tyr Arg Tyr Asp Tyr
            100                 105                 110

Trp Gly Gln Gly Thr Gln Val Thr Val Ser Ser
        115                 120

<210> SEQ ID NO 34
<211> LENGTH: 119
<212> TYPE: PRT
<213> ORGANISM: Artificial Sequence
<220> FEATURE:
<223> OTHER INFORMATION: synthetic

<400> SEQUENCE: 34

Asp Val Gln Leu Val Glu Ser Gly Gly Gly Leu Val Gln Pro Val Gly
1               5                   10                  15

Ser Leu Arg Leu Ser Cys Ala Ala Ser Gly Ser Ile Phe Thr Ile Asn
            20                  25                  30

```
Ala Met Val Trp Tyr Arg Gln Ala Pro Gly Lys Lys Arg Glu Glu Val
            35                  40                  45

Ala Ala Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Lys
                 85                  90                  95

Ala Val Val Val Thr Thr Thr Pro Tyr Ser Asp Tyr Trp Gly Gln Gly
                100                 105                 110

Thr Leu Val Thr Val Ser Ser
            115

<210> SEQ ID NO 35
<211> LENGTH: 119
<212> TYPE: PRT
<213> ORGANISM: Artificial Sequence
<220> FEATURE:
<223> OTHER INFORMATION: synthetic

<400> SEQUENCE: 35

Asp Val Gln Leu Val Glu Ser Gly Gly Gly Leu Val Gln Pro Gly Gly
 1               5                  10                  15

Ser Leu Arg Leu Ser Cys Ala Ala Gly Ser Ile Phe Thr Ile Asn
             20                  25                  30

Ala Met Gly Trp Tyr Arg Gln Ala Pro Gly Lys Gln Arg Glu Glu Val
             35                  40                  45

Ala Ala Ile Thr Ser Gly Gly Ser Thr Asn Tyr Ala Asp Ser Val Lys
 50                  55                  60

Gly Arg Phe Thr Ile Tyr Ser Gly Ser Asp Lys His Ala Val Tyr Leu
 65                  70                  75                  80

Gln Met Asn Asp Leu Asn Pro Val Glu Thr Gly Val Tyr Tyr Cys Thr
                 85                  90                  95

Ala Val Val Val Thr Thr Thr Ala Tyr Ser Asp Tyr Trp Gly Gln Gly
                100                 105                 110

Thr Leu Val Thr Val Thr Ser
            115

<210> SEQ ID NO 36
<211> LENGTH: 161
<212> TYPE: PRT
<213> ORGANISM: Artificial Sequence
<220> FEATURE:
<223> OTHER INFORMATION: synthetic

<400> SEQUENCE: 36

Asp Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Thr Ile Asn
             20                  25                  30

Ala Met Gly Trp Tyr Arg Gln Ala Pro Gly Lys Gln Arg Glu Glu Val
             35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Glu Val Ala Ala Ile Thr Ser Gly
                 85                  90                  95
```

Gly Ser Thr Asn Tyr Ala Asp Ser Val Lys Gly Arg Phe Thr Ile Ser
            100                 105                 110

Arg Asp Asn Ala Lys Asn Thr Val Tyr Leu Gln Met Asn Ser Leu Lys
            115                 120                 125

Pro Glu Asp Thr Ala Val Tyr Tyr Cys Lys Ala Val Val Thr Thr
130                 135                 140

Thr Pro Tyr Ser Asp Tyr Trp Gly Gln Gly Thr Leu Val Thr Val Ser
145                 150                 155                 160

Ser

<210> SEQ ID NO 37
<211> LENGTH: 119
<212> TYPE: PRT
<213> ORGANISM: Artificial Sequence
<220> FEATURE:
<223> OTHER INFORMATION: synthetic

<400> SEQUENCE: 37

Asp Val Gln Leu Val Glu Ser Gly Gly Gly Leu Val Gln Pro Gly Gly
1               5                   10                  15

Ser Leu Arg Leu Ser Cys Ala Ser Gly Ser Ile Phe Thr Ile Asn
            20                  25                  30

Ala Met Val Trp Tyr Arg Gln Ala Pro Gly Lys Gln Arg Glu Glu Val
            35                  40                  45

Ala Ala Leu Thr Ser Gly Gly Ser Thr Asn Ser Ala Asp Ser Val Lys
    50                  55                  60

Gly Arg Phe Thr Ile Ser Arg Asn Asn Ala Lys Asn Thr Val Tyr Arg
65                  70                  75                  80

Leu Arg Asn Ser Leu Lys Pro Val Asp Thr Ala Val Tyr Tyr Ala Lys
                85                  90                  95

Ala Val Val Val Thr Thr Thr Pro Tyr Ala Asp Tyr Trp Ala Gln Ala
            100                 105                 110

Thr Pro Val Ser Val Ser Ser
            115

<210> SEQ ID NO 38
<211> LENGTH: 118
<212> TYPE: PRT
<213> ORGANISM: Artificial Sequence
<220> FEATURE:
<223> OTHER INFORMATION: synthetic

<400> SEQUENCE: 38

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
            35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Val Val Val Thr Thr Pro Tyr Ser Asp Tyr Trp Gly Gln Gly Thr
            100                 105                 110

```
Leu Val Thr Val Ser Ser
        115

<210> SEQ ID NO 39
<211> LENGTH: 160
<212> TYPE: PRT
<213> ORGANISM: Artificial Sequence
<220> FEATURE:
<223> OTHER INFORMATION: synthetic

<400> SEQUENCE: 39

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Met Gly Trp Tyr Arg Gln
65                  70                  75                  80

Ala Pro Gly Lys Gln Arg Glu Glu Val Ala Ala Ile Thr Ser Gly Gly
                85                  90                  95

Ser Thr Asn Tyr Ala Asp Ser Val Lys Gly Arg Phe Thr Ile Ser Arg
            100                 105                 110

Asp Asn Ala Lys Asn Thr Val Tyr Leu Gln Met Asn Ser Leu Lys Pro
        115                 120                 125

Glu Asp Thr Ala Val Tyr Tyr Cys Lys Ala Val Val Thr Thr Thr
    130                 135                 140

Pro Tyr Ser Asp Tyr Trp Gly Gln Gly Thr Leu Val Thr Val Ser Ser
145                 150                 155                 160

<210> SEQ ID NO 40
<211> LENGTH: 120
<212> TYPE: PRT
<213> ORGANISM: Artificial Sequence
<220> FEATURE:
<223> OTHER INFORMATION: synthetic

<400> SEQUENCE: 40

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Ala Trp Phe Arg Gln Ala Pro Gly Lys Glu Arg Glu Ile Val
        35                  40                  45

Ala Ala Val Asn Gly Gly Ser Ser Thr Tyr Val Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Ala Val Val Val Thr Thr Thr Pro Tyr Ser Asp Tyr Trp Gly Gln
            100                 105                 110

Gly Thr Leu Val Thr Val Ser Ser
        115                 120
```

```
<210> SEQ ID NO 41
<211> LENGTH: 119
<212> TYPE: PRT
<213> ORGANISM: Artificial Sequence
<220> FEATURE:
<223> OTHER INFORMATION: synthetic

<400> SEQUENCE: 41

Tyr Val Gln Leu Ala Glu Ser Gly Gly Gly Leu Val Gln Pro Gly Gly
1               5                   10                  15

Ser Leu Ile Leu Ser Cys Ala Ala Ser Gly Ser Ile Cys Thr Ser Asn
            20                  25                  30

Ala Met Gly Trp Tyr Arg Pro Ala Leu Trp Lys Gln Arg Glu Glu Val
        35                  40                  45

Ala Asp Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Lys Val Thr Ala Val Tyr Tyr Cys Lys
                85                  90                  95

Ala Val Val Val Thr Thr Thr Pro Tyr Ser Asp Tyr Trp Gly Gln Gly
            100                 105                 110

Thr Leu Val Thr Val Ser Ser
        115

<210> SEQ ID NO 42
<211> LENGTH: 120
<212> TYPE: PRT
<213> ORGANISM: Artificial Sequence
<220> FEATURE:
<223> OTHER INFORMATION: synthetic

<400> SEQUENCE: 42

Asp Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ile Arg
            20                  25                  30

Val Met Gly Trp Phe Arg Gln Ala Pro Gly Lys Glu Arg Asp Phe Val
        35                  40                  45

Ala Ala Ile Met Trp Ser Gly Gly Ala Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Ala Val Val Val Thr Thr Thr Pro Tyr Ser Asp Tyr Trp Gly Gln
            100                 105                 110

Gly Thr Leu Val Thr Val Ser Ser
        115                 120

<210> SEQ ID NO 43
<211> LENGTH: 119
<212> TYPE: PRT
<213> ORGANISM: Artificial Sequence
<220> FEATURE:
<223> OTHER INFORMATION: synthetic

<400> SEQUENCE: 43

Asp Val Gln Leu Val Glu Ser Gly Gly Gly Leu Val Gln Pro Gly Gly
1               5                   10                  15
```

Val Ser Glu Thr Leu Leu Cys Ser Leu Trp Lys His Leu His Tyr Gln
            20                  25                  30

Cys His Gly Trp Tyr Arg Gln Ala Pro Gly Lys Gln Arg Glu Glu Val
            35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Lys
                85                  90                  95

Ala Val Val Val Thr Thr Thr Pro Tyr Ser Asp Tyr Trp Gly Gln Gly
            100                 105                 110

Thr Leu Val Thr Val Ser Ser
            115

<210> SEQ ID NO 44
<211> LENGTH: 146
<212> TYPE: PRT
<213> ORGANISM: Artificial Sequence
<220> FEATURE:
<223> OTHER INFORMATION: synthetic

<400> SEQUENCE: 44

Asp Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
            35                  40                  45

Ala Ala Ile Thr Ser Gly Gly Ser Thr Asn Asn Ala Met Gly Trp Tyr
 50                  55                  60

Arg Gln Ala Pro Gly Lys Gln Arg Glu Glu Val Ala Ala Ile Thr Ser
 65                  70                  75                  80

Gly Gly Ser Thr Asn Tyr Ala Asp Ser Val Lys Gly Arg Phe Thr Ile
                85                  90                  95

Ser Arg Asp Asn Ala Lys Asn Thr Val Tyr Leu Gln Met Asn Ser Leu
            100                 105                 110

Lys Pro Glu Asp Thr Ala Val Tyr Tyr Cys Lys Ala Val Val Val Thr
            115                 120                 125

Thr Thr Pro Tyr Ser Asp Tyr Trp Gly Gln Gly Thr Leu Val Thr Val
            130                 135                 140

Ser Ser
145

<210> SEQ ID NO 45
<211> LENGTH: 119
<212> TYPE: PRT
<213> ORGANISM: Artificial Sequence
<220> FEATURE:
<223> OTHER INFORMATION: synthetic

<400> SEQUENCE: 45

Asp Val Gln Pro Val Glu Ser Gly Gly Gly Leu Val Gln Pro Gly Gly
 1               5                  10                  15

Ser Leu Arg Leu Ser Cys Ala Ala Ser Val Ser Ile Phe Thr Ile Asn
            20                  25                  30

Ala Met Gly Trp Tyr Arg Gln Ala Pro Gly Lys Gln Arg Glu Glu Val

```
                35                  40                  45
Val Ala Asn Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Met Lys Pro Glu Asp Thr Ala Val Tyr Tyr Cys Lys
                 85                  90                  95

Ala Val Val Val Thr Thr Thr Gly Tyr Ser Asp Tyr Trp Gly Gln Gly
            100                 105                 110

Thr Leu Val Thr Val Ser Ser
            115
```

<210> SEQ ID NO 46
<211> LENGTH: 147
<212> TYPE: PRT
<213> ORGANISM: Artificial Sequence
<220> FEATURE:
<223> OTHER INFORMATION: synthetic

<400> SEQUENCE: 46

```
Val Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Thr Ile Asn
             20                  25                  30

Ala Met Gly Trp Tyr Arg Gln Ala Pro Gly Lys Gln Arg Glu Glu Val
         35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Val Lys Gly Arg Phe Thr
                 85                  90                  95

Ile Ser Arg Asp Asn Ala Lys Asn Lys Val Tyr Leu Gln Met Asn Arg
            100                 105                 110

Leu Asn Pro Glu Asp Thr Ala Val Tyr Tyr Cys Lys Ala Val Val Val
            115                 120                 125

Thr Thr Thr Pro Tyr Ser Asp Tyr Trp Gly Gln Gly Thr Leu Val Thr
            130                 135                 140

Val Ser Ser
145
```

<210> SEQ ID NO 47
<211> LENGTH: 119
<212> TYPE: PRT
<213> ORGANISM: Artificial Sequence
<220> FEATURE:
<223> OTHER INFORMATION: synthetic

<400> SEQUENCE: 47

```
Asp Val Gln Leu Val Glu Ser Gly Gly Gly Ser Val Gln Pro Gly Gly
 1               5                  10                  15

Ser Leu Arg Leu Ser Cys Ala Ala Ser Ala Arg Ile Phe Ser Ser Tyr
             20                  25                  30

His Lys Ala Trp Phe Arg Gln Ala Pro Gly Lys Glu Arg Glu Glu Val
         35                  40                  45

Ala Ala Ile Thr Ser Gly Gly Ser Thr Asn Tyr Ala Asp Ser Val Lys
 50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Lys
                 85                  90                  95

Ala Val Val Thr Thr Thr Pro Tyr Ser Asp Tyr Trp Gly Gln Gly
                100                 105                 110

Thr Leu Val Thr Val Ser Ser
            115

<210> SEQ ID NO 48
<211> LENGTH: 119
<212> TYPE: PRT
<213> ORGANISM: Artificial Sequence
<220> FEATURE:
<223> OTHER INFORMATION: synthetic

<400> SEQUENCE: 48

Asp Val Gln Leu Val Glu Ser Gly Gly Gly Leu Val Gln Pro Gly Gly
 1               5                  10                  15

Ser Leu Arg Leu Ser Cys Ala Ala Ser Gly Ser Leu Phe Thr Ile Asn
                20                  25                  30

Ala Met Gly Trp Tyr Arg Gln Ala Pro Gly Lys Gln Arg Glu Val
             35                  40                  45

Ala Ala Ile Thr Ser Gly Gly Ser Thr Asn Tyr Ala Asp Ser Val Lys
 50                  55                  60

Gly Arg Phe Thr Phe Ser Arg Asp Thr Ala Arg Asn Thr Val Cys Pro
 65                  70                  75                  80

Gln Met Asn Ser Leu Lys Pro Asp His Thr Ala Val Tyr Tyr Cys Lys
                 85                  90                  95

Ala Leu Val Val Pro Pro Thr Pro Tyr Ser Val Tyr Trp Gly Gln Gly
                100                 105                 110

Thr Leu Val Thr Val Ser Ser
            115

<210> SEQ ID NO 49
<211> LENGTH: 112
<212> TYPE: PRT
<213> ORGANISM: Artificial Sequence
<220> FEATURE:
<223> OTHER INFORMATION: synthetic

<400> SEQUENCE: 49

Asp Val Gln Leu Val Gln Pro Gly Gly Ser Leu Arg Leu Ser Cys Ala
 1               5                  10                  15

Ala Ser Gly Ser Ile Phe Thr Ile Asn Ala Met Gly Trp Tyr Arg Gln
                20                  25                  30

Ala Pro Gly Lys Gln Arg Glu Val Ala Ala Ile Thr Ser Gly Gly
             35                  40                  45

Ser Thr Asn Tyr Ala Asp Ser Val Lys Gly Arg Phe Thr Ile Ser Arg
 50                  55                  60

Asp Asn Ala Lys Asn Thr Val Tyr Leu Gln Met Asn Ser Leu Lys Pro
 65                  70                  75                  80

Glu Asp Thr Ala Val Tyr Tyr Cys Lys Ala Val Val Thr Thr Thr
                 85                  90                  95

Pro Tyr Ser Asp Tyr Trp Gly Gln Gly Thr Leu Val Thr Val Ser Ser
                100                 105                 110

<210> SEQ ID NO 50
```

```
<211> LENGTH: 177
<212> TYPE: PRT
<213> ORGANISM: Artificial Sequence
<220> FEATURE:
<223> OTHER INFORMATION: synthetic

<400> SEQUENCE: 50

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Met Gly Trp Tyr Arg
                85                  90                  95

Gln Ala Pro Gly Lys Gln Arg Glu Glu Val Ala Ala Ile Thr Ser Gly
            100                 105                 110

Gly Ser Thr Asn Tyr Ala Asp Ser Val Lys Gly Arg Phe Thr Ile Ser
        115                 120                 125

Arg Asp Asn Ala Lys Asn Thr Val Tyr Leu Gln Met Asn Ser Leu Lys
    130                 135                 140

Pro Glu Asp Thr Ala Val Tyr Tyr Cys Lys Ala Val Val Val Thr Thr
145                 150                 155                 160

Thr Pro Tyr Ser Asp Tyr Trp Gly Gln Gly Thr Leu Val Thr Val Ser
                165                 170                 175

Ser

<210> SEQ ID NO 51
<211> LENGTH: 119
<212> TYPE: PRT
<213> ORGANISM: Artificial Sequence
<220> FEATURE:
<223> OTHER INFORMATION: synthetic

<400> SEQUENCE: 51

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ser Thr Ser Gly Gly Ser Pro Asn Tyr Asp Asp Ser Val Lys
    50                  55                  60

Gly Pro Phe Asn Leu Ser Lys Asp Asn Ala Lys Asn Thr Val Tyr Leu
65                  70                  75                  80

Gln Ile Asn Arg Leu Lys Pro Glu Asp Thr Ala Val Tyr Phe Phe Lys
                85                  90                  95

Ala Gly Gly Gly Ser Ser Thr Pro Asp Ser Asp Tyr Trp Gly Gln Gly
            100                 105                 110

Thr Leu Val Thr Val Ser Ser
        115

<210> SEQ ID NO 52
```

<211> LENGTH: 164
<212> TYPE: PRT
<213> ORGANISM: Artificial Sequence
<220> FEATURE:
<223> OTHER INFORMATION: synthetic

<400> SEQUENCE: 52

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ser Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Lys Asp Met Gly
65                  70                  75                  80

Trp Tyr Arg Gln Ala Pro Gly Lys Gln Arg Glu Glu Val Ala Ala Ile
                85                  90                  95

Thr Ser Gly Gly Ser Thr Asn Tyr Ala Asp Ser Val Lys Gly Arg Phe
            100                 105                 110

Thr Ile Ser Arg Asp Asn Ala Lys Asn Thr Val Tyr Leu Gln Met Asn
        115                 120                 125

Ser Leu Lys Pro Glu Asp Thr Ala Val Tyr Tyr Cys Lys Ala Val Val
    130                 135                 140

Val Thr Thr Thr Pro Tyr Ser Asp Tyr Trp Gly Gln Gly Thr Leu Val
145                 150                 155                 160

Thr Val Ser Ser

<210> SEQ ID NO 53
<211> LENGTH: 136
<212> TYPE: PRT
<213> ORGANISM: Artificial Sequence
<220> FEATURE:
<223> OTHER INFORMATION: synthetic

<400> SEQUENCE: 53

Asp Val Gln Pro Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Lys Asn Thr Val Tyr
                85                  90                  95

Leu Lys Met Asn Ser Leu Lys Pro Glu Glu Thr Ala Val Tyr Tyr Cys
            100                 105                 110

Lys Ala Val Val Val Thr Thr Thr Pro Tyr Ser Asp Tyr Trp Gly Gln
        115                 120                 125

Gly Thr Leu Val Thr Val Cys Ser
    130                 135

<210> SEQ ID NO 54

```
<211> LENGTH: 149
<212> TYPE: PRT
<213> ORGANISM: Artificial Sequence
<220> FEATURE:
<223> OTHER INFORMATION: synthetic

<400> SEQUENCE: 54

Asp Val Gln Leu Val Glu Ser Gly Gly Gly Leu Val Gln Pro Gly Trp
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Val Lys Gln Arg Glu Glu Val
        35                  40                  45

Ala Ala Ile Thr Ser Gly Gly Ser Thr Asn Tyr Ala Asp Pro Val Lys
    50                  55                  60

Gly Trp Tyr Arg Gln Ala Pro Gly Lys Gln Arg Glu Glu Val Ala Ala
65                  70                  75                  80

Ile Thr Leu Val Gly Ser Thr Asn Tyr Ala Asp Ser Val Lys Gly Arg
                85                  90                  95

Phe Asn Ile Ser Arg Asp Asn Ala Lys Asn Thr Val Tyr Leu Gln Met
            100                 105                 110

Asn Ser Leu Lys Pro Glu Asp Thr Ala Val Tyr Tyr Cys Lys Ala Val
        115                 120                 125

Val Val Thr Thr Thr Pro Glu Ala Asp Tyr Trp Gly Gln Gly Thr Leu
    130                 135                 140

Val Thr Val Ser Ser
145

<210> SEQ ID NO 55
<211> LENGTH: 171
<212> TYPE: PRT
<213> ORGANISM: Artificial Sequence
<220> FEATURE:
<223> OTHER INFORMATION: synthetic

<400> SEQUENCE: 55

Val Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Thr Ile Asn
            20                  25                  30

Ala Met Gly Trp Tyr Arg Gln Ala Pro Gly Lys Gln Arg Glu Glu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Ser Gln Ala Pro Gly Lys Gln
                85                  90                  95

Arg Glu Glu Val Ala Ala Ile Thr Ser Gly Gly Ser Thr Asn Tyr Ala
            100                 105                 110

Asp Ser Val Lys Gly Arg Phe Thr Ile Ser Arg Asp Asn Ala Lys Asn
        115                 120                 125

Thr Val Tyr Leu Gln Met Asn Ser Leu Lys Pro Glu Asp Thr Ala Val
    130                 135                 140

Tyr Tyr Cys Lys Ala Val Val Val Thr Thr Thr Pro Tyr Ser Asp Tyr
145                 150                 155                 160

Trp Gly Gln Gly Thr Leu Val Thr Val Ser Ser
```

165          170

<210> SEQ ID NO 56
<211> LENGTH: 112
<212> TYPE: PRT
<213> ORGANISM: Artificial Sequence
<220> FEATURE:
<223> OTHER INFORMATION: synthetic

<400> SEQUENCE: 56

Asp Val Gln Leu Val Glu Ser Gly Gly Ser Leu Arg Leu Ser Cys Ala
1               5                   10                  15

Ala Ser Gly Ser Ile Phe Thr Ile Asn Ala Met Gly Trp Tyr Arg Gln
            20                  25                  30

Ala Pro Gly Lys Gln Arg Glu Glu Val Ala Ala Ile Thr Ser Gly Gly
        35                  40                  45

Ser Thr Asn Tyr Ala Asp Ser Val Lys Gly Arg Phe Thr Ile Ser Arg
    50                  55                  60

Asp Asn Ala Lys Asn Thr Val Tyr Leu Gln Met Asn Ser Leu Lys Pro
65                  70                  75                  80

Glu Asp Thr Ala Val Tyr Tyr Cys Lys Ala Val Val Thr Thr Thr
                85                  90                  95

Pro Tyr Ser Asp Tyr Trp Gly Gln Gly Thr Leu Val Thr Val Ser Ser
            100                 105                 110

<210> SEQ ID NO 57
<211> LENGTH: 639
<212> TYPE: DNA
<213> ORGANISM: Artificial Sequence
<220> FEATURE:
<223> OTHER INFORMATION: synthetic

<400> SEQUENCE: 57
atggccgatg ttcagctggt tgaaagcggc ggcggtctgg tgcagccggg tggtagctta      60
cgtctgagct gcgcagccag tggtagtatt tttacaatta atgctatggg ttggtaccgt     120
caggcaccgg gcaaacagcg cgaagaagtt gcagcaatta ccagcggtgg tagtaccaat     180
tatgccgata gcgtgaaagg tcgttttacc attagtcgcg ataatgcaaa aaataccgtt     240
tatctgcaga tgaatagcct gaaaccggaa gataccgcag tttattattg caaagccgtt     300
gtggtgacca ccacccccgta tagtgattat tggggtcagg gcaccctggt taccgttagc     360
agtattttta caattaatgc tatgggttgg taccgtcagg caccgggcaa acagcgcgaa     420
gaagttgcag caattaccag cggtggtagt accaattatg ccgatagcgt gaaaggtcgt     480
tttaccatta gtcgcgataa tgcaaaaaat accgtttatc tgcagatgaa tagcctgaaa     540
ccggaagata ccgcagttta ttattgcaaa gccgttgtgg tgaccaccac cccgtatagt     600
gattattggg gtcagggcac cctggttacc gttagcagt                            639

<210> SEQ ID NO 58
<211> LENGTH: 213
<212> TYPE: PRT
<213> ORGANISM: Artificial Sequence
<220> FEATURE:
<223> OTHER INFORMATION: synthetic

<400> SEQUENCE: 58

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr

```
            20                  25                  30
Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
 50                  55                  60

Val Lys Gly Arg Phe Thr Ile Ser Arg Asp Asn Ala Lys Asn Thr Val
 65                  70                  75                  80

Tyr Leu Gln Met Asn Ser Leu Lys Pro Glu Asp Thr Ala Val Tyr Tyr
                85                  90                  95

Cys Lys Ala Val Val Val Thr Thr Thr Pro Tyr Ser Asp Tyr Trp Gly
                100                 105                 110

Gln Gly Thr Leu Val Thr Val Ser Ser Ile Phe Thr Ile Asn Ala Met
            115                 120                 125

Gly Trp Tyr Arg Gln Ala Pro Gly Lys Gln Arg Glu Glu Val Ala Ala
        130                 135                 140

Ile Thr Ser Gly Gly Ser Thr Asn Tyr Ala Asp Ser Val Lys Gly Arg
145                 150                 155                 160

Phe Thr Ile Ser Arg Asp Asn Ala Lys Asn Thr Val Tyr Leu Gln Met
                165                 170                 175

Asn Ser Leu Lys Pro Glu Asp Thr Ala Val Tyr Tyr Cys Lys Ala Val
            180                 185                 190

Val Val Thr Thr Thr Pro Tyr Ser Asp Tyr Trp Gly Gln Gly Thr Leu
        195                 200                 205

Val Thr Val Ser Ser
    210
```

<210> SEQ ID NO 59
<211> LENGTH: 378
<212> TYPE: DNA
<213> ORGANISM: Artificial Sequence
<220> FEATURE:
<223> OTHER INFORMATION: synthetic

<400> SEQUENCE: 59

```
atggcccagg ttcagctggt tgaaagtggc ggtggcctgg tgcaggccgg tggtagctta      60
cgtctgagct gtgccgccag cgcccgtatt tttagtagtt atcataaagc atggttccgt     120
caggccccgg gcaaagaacg tgaaattgtg gccgccgtga atggcggtag tagcagcacc     180
tatgttgcag atagtgtgaa aggtcgtttt accattagtg gtgacaatgc ctgaatacc     240 gttagcctgc agatgaatag cctgaaaccg gaagataccg ccgtgtatta ttgtgcagca     300
gcaggccgcg ccggtccgtt agcagcaagt tatcgttatg attattgggg tcagggcacc     360
caggtgaccg ttagcagt                                                   378
```

<210> SEQ ID NO 60
<211> LENGTH: 126
<212> TYPE: PRT
<213> ORGANISM: Artificial Sequence
<220> FEATURE:
<223> OTHER INFORMATION: synthetic

<400> SEQUENCE: 60

```
Met Ala Gln Val Gln Leu Val Glu Ser Gly Gly Gly Leu Val Gln Ala
  1               5                  10                  15

Gly Gly Ser Leu Arg Leu Ser Cys Ala Ala Ser Ala Arg Ile Phe Ser
            20                  25                  30

Ser Tyr His Lys Ala Trp Phe Arg Gln Ala Pro Gly Lys Glu Arg Glu
```

```
                35                  40                  45
Ile Val Ala Ala Val Asn Gly Gly Ser Ser Thr Tyr Val Ala Asp
    50                  55                  60

Ser Val Lys Gly Arg Phe Thr Ile Ser Gly Asp Asn Ala Leu Asn Thr
65                  70                  75                  80

Val Ser Leu Gln Met Asn Ser Leu Lys Pro Glu Asp Thr Ala Val Tyr
                85                  90                  95

Tyr Cys Ala Ala Ala Gly Arg Ala Gly Pro Leu Ala Ala Ser Tyr Arg
            100                 105                 110

Tyr Asp Tyr Trp Gly Gln Gly Thr Gln Val Thr Val Ser Ser
            115                 120                 125

<210> SEQ ID NO 61
<211> LENGTH: 366
<212> TYPE: DNA
<213> ORGANISM: Artificial Sequence
<220> FEATURE:
<223> OTHER INFORMATION: synthetic

<400> SEQUENCE: 61
atggcccagg ttcagctggt ggaaagtggc ggcggcctgg tgcaggctgg tggtagctta      60
cgtctgagct gtgcagcaag cgcacgcatt tttagtagct atcataaagc atggttccgt    120
caggccccgg gcaaagaacg cgaaattgtt gccgccgtta atggtggcag tagcagtacc    180
tatgtggccg atagcgttaa aggccgcttt accattagtg gtgacaatgc cctgaatacc    240
gttagcctgc agatgaatag cctgaaaccg gaagataccg cagtgtatta ttgtaaagca    300
gttgtggtga ccaccacccc gtatagtgat tattggggtc agggcaccct ggtgaccgtg    360
agcagc                                                              366

<210> SEQ ID NO 62
<211> LENGTH: 122
<212> TYPE: PRT
<213> ORGANISM: Artificial Sequence
<220> FEATURE:
<223> OTHER INFORMATION: synthetic

<400> SEQUENCE: 62

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Ala Arg Ile Phe Ser
            20                  25                  30

Ser Tyr His Lys Ala Trp Phe Arg Gln Ala Pro Gly Lys Glu Arg Glu
        35                  40                  45

Ile Val Ala Ala Val Asn Gly Gly Ser Ser Thr Tyr Val Ala Asp
    50                  55                  60

Ser Val Lys Gly Arg Phe Thr Ile Ser Gly Asp Asn Ala Leu Asn Thr
65                  70                  75                  80

Val Ser Leu Gln Met Asn Ser Leu Lys Pro Glu Asp Thr Ala Val Tyr
                85                  90                  95

Tyr Cys Lys Ala Val Val Val Thr Thr Thr Pro Tyr Ser Asp Tyr Trp
            100                 105                 110

Gly Gln Gly Thr Leu Val Thr Val Ser Ser
            115                 120

<210> SEQ ID NO 63
<211> LENGTH: 375
<212> TYPE: DNA
```

<213> ORGANISM: Artificial Sequence
<220> FEATURE:
<223> OTHER INFORMATION: synthetic

<400> SEQUENCE: 63

```
atggccgatg ttcagctggt ggaaagtggc ggcggcctgg ttcagccggg tggtagctta      60
cgtctgagct gtgcagcaag cggtagtatt tttacaatta atgctatggg ttggtaccgt     120
caggcaccgg gtaaacagcg cgaagaagtg gcagcaatta ccagcggtgg tagtaccaat     180
tatgccgata gcgtgaaagg ccgttttacc attagccgcg ataatgccaa aaataccgtt     240
tatctgcaga tgaatagtct gaaaccggaa gataccgcag tttattattg cgccgccgcc     300
ggccgcgccg gtcctctggc agcaagctat cgctatgatt attggggcca gggtacccag     360
gttaccgtga gcagc                                                      375
```

<210> SEQ ID NO 64
<211> LENGTH: 125
<212> TYPE: PRT
<213> ORGANISM: Artificial Sequence
<220> FEATURE:
<223> OTHER INFORMATION: synthetic

<400> SEQUENCE: 64

```
Met Ala Asp Val Gln Leu Val Glu Ser Gly Gly Gly Leu Val Gln Pro
  1               5                  10                  15

Gly Gly Ser Leu Arg Leu Ser Cys Ala Ala Ser Gly Ser Ile Phe Thr
             20                  25                  30

Ile Asn Ala Met Gly Trp Tyr Arg Gln Ala Pro Gly Lys Gln Arg Glu
         35                  40                  45

Glu Val Ala Ala Ile Thr Ser Gly Gly Ser Thr Asn Tyr Ala Asp Ser
     50                  55                  60

Val Lys Gly Arg Phe Thr Ile Ser Arg Asp Asn Ala Lys Asn Thr Val
 65                  70                  75                  80

Tyr Leu Gln Met Asn Ser Leu Lys Pro Glu Asp Thr Ala Val Tyr Tyr
                 85                  90                  95

Cys Ala Ala Ala Gly Arg Ala Gly Pro Leu Ala Ala Ser Tyr Arg Tyr
            100                 105                 110

Asp Tyr Trp Gly Gln Gly Thr Gln Val Thr Val Ser Ser
        115                 120                 125
```

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65

```
atggccgatg ttcagctggt tgaaagtggc ggcggtctgg tgcagccggt tggtagtctg      60
cgtctgagtt gtgccgccag cggtagcatt tttacaatta atgctatggt ttggtaccgc     120
caggcaccgg gtaaaaaacg cgaagaagtg gcagccatta cccgcggcgg tagcaccaat     180
tatgcagata gcgttaaagg ccgttttacc attagccgcg ataatgccaa aaataccgtg     240
tatctgcaga tgaatagcct gaaaccggaa gataccgcag tttattattg taaagcagtg     300
gttgtgacca ccaccccgta tagcgattat tggggccagg gtaccctggt gaccgttagc     360
agc                                                                   363
```

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Met Ala Asp Val Gln Leu Val Glu Ser Gly Gly Leu Val Gln Pro
1               5                   10                  15

Val Gly Ser Leu Arg Leu Ser Cys Ala Ser Gly Ser Ile Phe Thr
                20                  25                  30

Ile Asn Ala Met Val Trp Tyr Arg Gln Ala Pro Gly Lys Lys Arg Glu
            35                  40                  45

Glu Val Ala Ala Ile Thr Arg Gly Gly Ser Thr Asn Tyr Ala Asp Ser
        50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Lys Ala Val Val Val Thr Thr Thr Pro Tyr Ser Asp Tyr Trp Gly
            100                 105                 110

Gln Gly Thr Leu Val Thr Val Ser Ser
        115                 120

<210> SEQ ID NO 67
<211> LENGTH: 376
<212> TYPE: DNA
<213> ORGANISM: Artificial Sequence
<220> FEATURE:
<223> OTHER INFORMATION: synthetic

<400> SEQUENCE: 67
atggccgatg ttcagctggt ggaaagcggc ggcggtctgg ttcagccggg tggtagtctg      60
cgcctgagct gcgctgcagc cggtagtatt tttacaatta atgctatggg ttggtaccgt     120
caggccccgg gtaaacagcg tgaagaagtg gcagccatta ccagcggtgg cagtaccaat     180
tatgcagata gcgtgaaagg tcgctttacc atctatagcg tagtgataa acatgcagtg     240
tatctgcaga tgaatgatct gaatccggtt gaaaccggtg tttattattg caccgcagtg     300
gttgtgacca ccaccgcata tagcgattat tggggtcagg gtaccctggt taccgttacc     360
agtctcgagg cggccg                                                     376

<210> SEQ ID NO 68
<211> LENGTH: 121
<212> TYPE: PRT
<213> ORGANISM: Artificial Sequence
<220> FEATURE:
<223> OTHER INFORMATION: synthetic

<400> SEQUENCE: 68

Met Ala Asp Val Gln Leu Val Glu Ser Gly Gly Gly Leu Val Gln Pro
1               5                   10                  15

Gly Gly Ser Leu Arg Leu Ser Cys Ala Ala Ala Gly Ser Ile Phe Thr
                20                  25                  30

Ile Asn Ala Met Gly Trp Tyr Arg Gln Ala Pro Gly Lys Gln Arg Glu
            35                  40                  45

Glu Val Ala Ala Ile Thr Ser Gly Gly Ser Thr Asn Tyr Ala Asp Ser
        50                  55                  60

```
Val Lys Gly Arg Phe Thr Ile Tyr Ser Gly Ser Asp Lys His Ala Val
 65                  70                  75                  80

Tyr Leu Gln Met Asn Asp Leu Asn Pro Val Glu Thr Gly Val Tyr Tyr
                 85                  90                  95

Cys Thr Ala Val Val Thr Thr Ala Tyr Ser Asp Tyr Trp Gly
            100                 105                 110

Gln Gly Thr Leu Val Thr Val Ser
            115                 120
```

<210> SEQ ID NO 69
<211> LENGTH: 363
<212> TYPE: DNA
<213> ORGANISM: Artificial Sequence
<220> FEATURE:
<223> OTHER INFORMATION: synthetic

<400> SEQUENCE: 69

```
atggccgatg ttcagctggt tgaaagtggt ggcggcctgg ttcagccggg cggtagctta      60
cgcctgagtt gtgccagtag tggtagtatt tttacaatta atgctatggt ttggtaccgc     120
caggccccgg gcaaacagcg tgaagaagtg gccgcactga ccagcggcgg tagcacaaat     180
agcgccgata gcgtgaaagg tcgttttacc attagtcgca ataatgccaa aaataccgtt     240
tatcgcctgc gcaatagtct gaaaccggtt gataccgccg tttattatgc caaagccgtt     300
gttgttacca ccacccgta tgcagattat tgggcacagg ccaccccggt tagtgtgagc     360
agc                                                                  363
```

<210> SEQ ID NO 70
<211> LENGTH: 121
<212> TYPE: PRT
<213> ORGANISM: Artificial Sequence
<220> FEATURE:
<223> OTHER INFORMATION: synthetic

<400> SEQUENCE: 70

```
Met Ala Asp Val Gln Leu Val Glu Ser Gly Gly Gly Leu Val Gln Pro
  1               5                  10                  15

Gly Gly Ser Leu Arg Leu Ser Cys Ala Ser Ser Gly Ser Ile Phe Thr
             20                  25                  30

Ile Asn Ala Met Val Trp Tyr Arg Gln Ala Pro Gly Lys Gln Arg Glu
         35                  40                  45

Glu Val Ala Ala Leu Thr Ser Gly Gly Ser Thr Asn Ser Ala Asp Ser
     50                  55                  60

Val Lys Gly Arg Phe Thr Ile Ser Arg Asn Asn Ala Lys Asn Thr Val
 65                  70                  75                  80

Tyr Arg Leu Arg Asn Ser Leu Lys Pro Val Asp Thr Ala Val Tyr Tyr
                 85                  90                  95

Ala Lys Ala Val Val Val Thr Thr Thr Pro Tyr Ala Asp Tyr Trp Ala
            100                 105                 110

Gln Ala Thr Pro Val Ser Val Ser Ser
            115                 120
```

<210> SEQ ID NO 71
<211> LENGTH: 360
<212> TYPE: DNA
<213> ORGANISM: Artificial Sequence
<220> FEATURE:
<223> OTHER INFORMATION: synthetic

<400> SEQUENCE: 71

```
atggccgatg ttcagctggt ggaaagcggt ggtggtctgg ttcagccggg tggtagcctg      60
cgcctgagct gtgctgccag tggcagtatt tttacaatta atgctatggg ttggtaccgt     120
caggccccgg gtaaacagcg tgaagaagtg ccgccatta ccagcggtgg cagcaccaat      180
tatgcagata gcgttaaagg tcgttttacc attagtcgcg ataatgcaaa aaataccgtg     240
tatctgcaga tgaatagcct gaaaccggaa gataccgcag tttattattg taaagcagtg     300
gtggttacca ccccgtatag cgattattgg ggccagggta ccctggtgac cgtgagcagt     360
```

<210> SEQ ID NO 72
<211> LENGTH: 120
<212> TYPE: PRT
<213> ORGANISM: Artificial Sequence
<220> FEATURE:
<223> OTHER INFORMATION: synthetic

<400> SEQUENCE: 72

```
Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Lys Ala Val Val Val Thr Thr Pro Tyr Ser Asp Tyr Trp Gly Gln
            100                 105                 110

Gly Thr Leu Val Thr Val Ser Ser
        115                 120
```

<210> SEQ ID NO 73
<211> LENGTH: 486
<212> TYPE: DNA
<213> ORGANISM: Artificial Sequence
<220> FEATURE:
<223> OTHER INFORMATION: synthetic

<400> SEQUENCE: 73

```
atggccgatg tgcagctggt ggaaagcggt ggcggcctgg tgcagcctgg tggttcactg      60
cgcctgagct gcgccgctag cggtagtatt tttacaatta atgctatggg ttggtaccgt     120
caggccccgg gtaaacagcg tgaagaagtt gccgcaatta ccagtggtgg cagtaccaat     180
tatgccgata gcgtgaaagg ccgctttacc attagccgcg ataatgcaat gggttggtat     240
cgtcaggcac cgggtaaaca acgtgaagaa gtggcagcaa ttacctcagg cggcagtacc     300
aactatgccg attcagtgaa aggtcgtttt accattagtc gtgataatgc aaaaaacacc     360
gtttatctgc agatgaatag cctgaaaccg aagataccg cagtttatta ttgcaaagcc     420
gttgtggtta ccaccacccc gtatagtgat tattggggtc agggtaccct ggtgaccgtt     480
agtagc                                                                486
```

<210> SEQ ID NO 74
<211> LENGTH: 162
<212> TYPE: PRT

<213> ORGANISM: Artificial Sequence
<220> FEATURE:
<223> OTHER INFORMATION: synthetic

<400> SEQUENCE: 74

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Met Gly Trp Tyr
65                  70                  75                  80

Arg Gln Ala Pro Gly Lys Gln Arg Glu Glu Val Ala Ala Ile Thr Ser
                85                  90                  95

Gly Gly Ser Thr Asn Tyr Ala Asp Ser Val Lys Gly Arg Phe Thr Ile
            100                 105                 110

Ser Arg Asp Asn Ala Lys Asn Thr Val Tyr Leu Gln Met Asn Ser Leu
        115                 120                 125

Lys Pro Glu Asp Thr Ala Val Tyr Tyr Cys Lys Ala Val Val Val Thr
    130                 135                 140

Thr Thr Pro Tyr Ser Asp Tyr Trp Gly Gln Gly Thr Leu Val Thr Val
145                 150                 155                 160

Ser Ser

<210> SEQ ID NO 75
<211> LENGTH: 366
<212> TYPE: DNA
<213> ORGANISM: Artificial Sequence
<220> FEATURE:
<223> OTHER INFORMATION: synthetic

<400> SEQUENCE: 75
atggccgatg tgcagctggt ggaaagcggt ggcggtctgg ttcagccggg cggttcactg     60
cgcctgagct gtgcagccag cggctcaatt tttacaatta atgctatggc ttggttccgc    120
caggccccgg gtaaagaacg tgaaattgtg gcagccgtta atggtggcag tagtagcacc    180
tatgtggcag atagcgtgaa aggccgtttt accattagtc gcgataatgc aaaaatacc     240 gtgtatctgc agatgaatag tctgaaaccg gaagataccg ccgtgtatta ttgtaaagcc    300
gtggttgtta ccaccacccc gtatagcgat tattggggcc agggtaccct ggttaccgtt    360
agcagc                                                              366

<210> SEQ ID NO 76
<211> LENGTH: 122
<212> TYPE: PRT
<213> ORGANISM: Artificial Sequence
<220> FEATURE:
<223> OTHER INFORMATION: synthetic

<400> SEQUENCE: 76

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Ala Trp Phe Arg Gln Ala Pro Gly Lys Glu Arg Glu

```
                35                  40                  45

Ile Val Ala Ala Val Asn Gly Gly Ser Ser Thr Tyr Val Ala Asp
         50                  55                  60

Ser Val Lys Gly Arg Phe Thr Ile Ser Arg Asp Asn Ala Lys Asn Thr
 65                  70                  75                  80

Val Tyr Leu Gln Met Asn Ser Leu Lys Pro Glu Asp Thr Ala Val Tyr
                 85                  90                  95

Tyr Cys Lys Ala Val Val Thr Thr Thr Pro Tyr Ser Asp Tyr Trp
             100                 105                 110

Gly Gln Gly Thr Leu Val Thr Val Ser Ser
            115                 120
```

<210> SEQ ID NO 77
<211> LENGTH: 363
<212> TYPE: DNA
<213> ORGANISM: Artificial Sequence
<220> FEATURE:
<223> OTHER INFORMATION: synthetic

<400> SEQUENCE: 77

```
atggcctacg ttcagctggc cgaaagcggt ggtggtctgg ttcagccggg tggcagtctg      60
attctgagct gtgccgcaag cggcagtatt tgcacctcaa atgctatggg ttggtatcgc     120
ccggccctgt ggaaacagcg cgaagaagtg gccgatatta ccagcggtgg tagcaccaat     180
tatgccgata gcgttaaagg ccgctttacc attagccgtg ataatgccaa aaataccgtt     240
tatctgcaga tgaatagtct gaaaccgaaa gtgaccgcag tttattattg caaagcagtt     300
gttgttacca ccaccccgta tagtgattat tggggtcagg gcaccctggt taccgttagc     360
agt                                                                   363
```

<210> SEQ ID NO 78
<211> LENGTH: 121
<212> TYPE: PRT
<213> ORGANISM: Artificial Sequence
<220> FEATURE:
<223> OTHER INFORMATION: synthetic

<400> SEQUENCE: 78

```
Met Ala Tyr Val Gln Leu Ala Glu Ser Gly Gly Gly Leu Val Gln Pro
 1               5                  10                  15

Gly Gly Ser Leu Ile Leu Ser Cys Ala Ala Ser Gly Ser Ile Cys Thr
             20                  25                  30

Ser Asn Ala Met Gly Trp Tyr Arg Pro Ala Leu Trp Lys Gln Arg Glu
         35                  40                  45

Glu Val Ala Asp Ile Thr Ser Gly Gly Ser Thr Asn Tyr Ala Asp Ser
     50                  55                  60

Val Lys Gly Arg Phe Thr Ile Ser Arg Asp Asn Ala Lys Asn Thr Val
 65                  70                  75                  80

Tyr Leu Gln Met Asn Ser Leu Lys Pro Lys Val Thr Ala Val Tyr Tyr
                 85                  90                  95

Cys Lys Ala Val Val Val Thr Thr Thr Pro Tyr Ser Asp Tyr Trp Gly
             100                 105                 110

Gln Gly Thr Leu Val Thr Val Ser Ser
            115                 120
```

<210> SEQ ID NO 79
<211> LENGTH: 365
<212> TYPE: DNA

<213> ORGANISM: Artificial Sequence
<220> FEATURE:
<223> OTHER INFORMATION: synthetic

<400> SEQUENCE: 79

```
atggccgatg ttcagctggt ggaaagcggc ggtggcctgg tgcagcctgg tggtagtctg    60
cgtctgagct gtgccgcaag cggcctgacc tttagtattc gcgttatggg ttggtttcgc   120
caggcaccgg gcaaagacgt gattttgttg ccgcaattat gtggagcggc ggcgcaacct   180
attatgcaga tagcgtgaaa ggtcgtttta ccattagtcg tgataatgcc aaaaataccg   240
tgtatctgca gatgaatagt ctgaaaccgg aagataccgc cgtttattat tgcaaagccg   300
ttgttgttac caccacccct atagtgatt attggggcca gggcaccctg gttaccgtta    360
gtagc                                                              365
```

<210> SEQ ID NO 80
<211> LENGTH: 122
<212> TYPE: PRT
<213> ORGANISM: Artificial Sequence
<220> FEATURE:
<223> OTHER INFORMATION: synthetic

<400> SEQUENCE: 80

```
Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Leu Thr Phe Ser
            20                  25                  30

Ile Arg Val Met Gly Trp Phe Arg Gln Ala Pro Gly Lys Glu Arg Asp
        35                  40                  45

Phe Val Ala Ala Ile Met Trp Ser Gly Gly Ala Thr Tyr Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Lys Ala Val Val Val Thr Thr Thr Pro Tyr Ser Asp Tyr Trp
            100                 105                 110

Gly Gln Gly Thr Leu Val Thr Val Ser Ser
        115                 120
```

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81

```
atggccgatg ttcagctggt tgaaagtggc ggtggcctgg tgcagccggg tggtgtgtca    60
gaaaccctgc tgtgtagtct gtggaaacat ctgcattatc agtgtcatgg ctggtatcgt   120
caggccccgg gcaaacagcg tgaagaagtg gccgccatta ccagtggcgg cagtaccaat   180
tatgccgata cgttaaagg tcgtttttacc attagccgtg ataatgcaaa aaataccgtg   240
tatctgcaga tgaatagcct gaaaccggaa gataccgccg tttattattg caaagcagtg   300
gtggtgacca ccaccccgta tagcgattat tggggccagg gcaccctggt taccgttagc   360
agt                                                                363
```

```
<210> SEQ ID NO 82
<211> LENGTH: 121
<212> TYPE: PRT
<213> ORGANISM: Artificial Sequence
<220> FEATURE:
<223> OTHER INFORMATION: synthetic

<400> SEQUENCE: 82

Met Ala Asp Val Gln Leu Val Glu Ser Gly Gly Leu Val Gln Pro
1               5                   10                  15

Gly Gly Val Ser Glu Thr Leu Leu Cys Ser Leu Trp Lys His Leu His
            20                  25                  30

Tyr Gln Cys His Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Lys Ala Val Val Val Thr Thr Thr Pro Tyr Ser Asp Tyr Trp Gly
            100                 105                 110

Gln Gly Thr Leu Val Thr Val Ser Ser
        115                 120

<210> SEQ ID NO 83
<211> LENGTH: 444
<212> TYPE: DNA
<213> ORGANISM: Artificial Sequence
<220> FEATURE:
<223> OTHER INFORMATION: synthetic

<400> SEQUENCE: 83
atggccgatg tgcagctggt ggaaagtggt ggtggtctgg tgcagccggg tggctcactg      60
cgtctgagtt gcgccgccag cggtagcatt tttacaatta atgctatggg ttggtaccgc     120 caggcccccgg gtaaacagcg cgaagaagtt gccgcaatta ccagcggtgg cagcacaaat    180
aatgctatgg gttggtatcg ccaggcaccg ggtaaacaac gcgaagaagt ggcagcaatt     240
acctcaggcg gcagcaccaa ttatgccgat agcgttaaag gccgctttac cattagtcgc     300
gataatgcca aaaataccgt ttatctgcag atgaatagtc tgaaaccgga agataccgca     360
gtgtattatt gcaaagccgt tgtggttacc accccccgt atagtgatta ttggggtcag      420
ggcacccctg gttaccgtta gcagc                                           444

<210> SEQ ID NO 84
<211> LENGTH: 148
<212> TYPE: PRT
<213> ORGANISM: Artificial Sequence
<220> FEATURE:
<223> OTHER INFORMATION: synthetic

<400> SEQUENCE: 84

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Asn Ala Met Gly
```

```
                 50                  55                  60

Trp Tyr Arg Gln Ala Pro Gly Lys Gln Arg Glu Val Ala Ala Ile
 65                  70                  75                  80

Thr Ser Gly Gly Ser Thr Asn Tyr Ala Asp Ser Val Lys Gly Arg Phe
                 85                  90                  95

Thr Ile Ser Arg Asp Asn Ala Lys Asn Thr Val Tyr Leu Gln Met Asn
                100                 105                 110

Ser Leu Lys Pro Glu Asp Thr Ala Val Tyr Tyr Cys Lys Ala Val Val
            115                 120                 125

Val Thr Thr Thr Pro Tyr Ser Asp Tyr Trp Gly Gln Gly Thr Leu Val
        130                 135                 140

Thr Val Ser Ser
145

<210> SEQ ID NO 85
<211> LENGTH: 363
<212> TYPE: DNA
<213> ORGANISM: Artificial Sequence
<220> FEATURE:
<223> OTHER INFORMATION: synthetic

<400> SEQUENCE: 85
atggccgatg ttcagccggt ggaaagcggt ggcggcctgg ttcagccggg tggttcactg      60
cgcctgagtt gcgcagccag tgttagtatt tttacaatta atgctatggg ttggtaccgt     120
caggcaccgg gcaaacagcg cgaagaagtt gttgccaata ccagcggcgg tagcaccaat     180
tatgcagata gcgtgaaagg tcgttttacc attagtcgtg ataatgcaaa aaacaccgtt     240
tatctgcaga tgaatagcat gaaaccggaa gataccgcag tgtattattg taaagccgtt     300
gtggtgacca ccacccagta tagcgattat tggggtcagg gtaccctggt taccgtgagc     360
agc                                                                   363

<210> SEQ ID NO 86
<211> LENGTH: 121
<212> TYPE: PRT
<213> ORGANISM: Artificial Sequence
<220> FEATURE:
<223> OTHER INFORMATION: synthetic

<400> SEQUENCE: 86

Met Ala Asp Val Gln Pro Val Glu Ser Gly Gly Gly Leu Val Gln Pro
  1               5                  10                  15

Gly Gly Ser Leu Arg Leu Ser Cys Ala Ala Ser Val Ser Ile Phe Thr
                 20                  25                  30

Ile Asn Ala Met Gly Trp Tyr Arg Gln Ala Pro Gly Lys Gln Arg Glu
             35                  40                  45

Glu Val Val Ala Asn Thr Ser Gly Gly Ser Thr Asn Tyr Ala Asp Ser
         50                  55                  60

Val Lys Gly Arg Phe Thr Ile Ser Arg Asp Asn Ala Lys Asn Thr Val
 65                  70                  75                  80

Tyr Leu Gln Met Asn Ser Met Lys Pro Glu Asp Thr Ala Val Tyr Tyr
                 85                  90                  95

Cys Lys Ala Val Val Val Thr Thr Thr Gln Tyr Ser Asp Tyr Trp Gly
                100                 105                 110

Gln Gly Thr Leu Val Thr Val Ser Ser
            115                 120
```

```
<210> SEQ ID NO 87
<211> LENGTH: 447
<212> TYPE: DNA
<213> ORGANISM: Artificial Sequence
<220> FEATURE:
<223> OTHER INFORMATION: synthetic

<400> SEQUENCE: 87
atggccgtgg ttcagctggt tgaaagtggt ggtggcctgg ttcagccggg cggttcactg      60
cgtctgagtt gtgccgcaag tggtagtatt tttacaatta atgctatggg ttggtaccgc     120
caggcaccgg gtaaacagcg tgaagaagtg ccgcaatta ccagtggcgg cagcaccaat      180
tatgcagata gcgttaaagg ccgttttacc attagtcgcg ataatgccaa aaataccgtt     240
tatctgcaga tgaatagtct gaaaccggaa gataccgtga aaggccgttt caccattagc     300
cgtgataatg caaaaaataa ggtgtatctg cagatgaacc gtctgaatcc ggaagataca     360
gcagtttatt attgcaaagc agttgtggtg accaccaccc cgtatagtga ttattggggt     420
cagggtaccc tggttaccgt tagtagc                                         447

<210> SEQ ID NO 88
<211> LENGTH: 149
<212> TYPE: PRT
<213> ORGANISM: Artificial Sequence
<220> FEATURE:
<223> OTHER INFORMATION: synthetic

<400> SEQUENCE: 88

Met Ala Val Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Val Lys Gly Arg
                85                  90                  95

Phe Thr Ile Ser Arg Asp Asn Ala Lys Asn Lys Val Tyr Leu Gln Met
            100                 105                 110

Asn Arg Leu Asn Pro Glu Asp Thr Ala Val Tyr Tyr Cys Lys Ala Val
        115                 120                 125

Val Val Thr Thr Thr Pro Tyr Ser Asp Tyr Trp Gly Gln Gly Thr Leu
    130                 135                 140

Val Thr Val Ser Ser
145

<210> SEQ ID NO 89
<211> LENGTH: 363
<212> TYPE: DNA
<213> ORGANISM: Artificial Sequence
<220> FEATURE:
<223> OTHER INFORMATION: synthetic

<400> SEQUENCE: 89
atggccgatg ttcagctggt ggaaagcggt ggcggtagcg ttcagccggg tggtagtctg      60
cgtctgagct gtgcagccag tgcccgcatt tttagtagct atcataaagc atggttccgt     120
```

```
caggccccgg gcaaagaacg cgaagaagtt gcagccatta ccagtggtgg cagcaccaat    180
tatgcagata gcgttaaagg ccgtttttacc attagccgcg ataatgccaa aaataccgtt    240
tatctgcaga tgaatagcct gaaaccggaa gataccgcag tttattattg taaagccgtt    300
gtggtgacca ccaccccgta tagcgattat tggggtcagg gtaccctggt taccgtgagc    360
agt                                                                  363
```

<210> SEQ ID NO 90
<211> LENGTH: 121
<212> TYPE: PRT
<213> ORGANISM: Artificial Sequence
<220> FEATURE:
<223> OTHER INFORMATION: synthetic

<400> SEQUENCE: 90

```
Met Ala Asp Val Gln Leu Val Glu Ser Gly Gly Gly Ser Val Gln Pro
 1               5                  10                  15

Gly Gly Ser Leu Arg Leu Ser Cys Ala Ala Ser Ala Arg Ile Phe Ser
             20                  25                  30

Ser Tyr His Lys Ala Trp Phe Arg Gln Ala Pro Gly Lys Glu Arg Glu
         35                  40                  45

Glu Val Ala Ala Ile Thr Ser Gly Gly Ser Thr Asn Tyr Ala Asp Ser
     50                  55                  60

Val Lys Gly Arg Phe Thr Ile Ser Arg Asp Asn Ala Lys Asn Thr Val
 65                  70                  75                  80

Tyr Leu Gln Met Asn Ser Leu Lys Pro Glu Asp Thr Ala Val Tyr Tyr
                 85                  90                  95

Cys Lys Ala Val Val Val Thr Thr Thr Pro Tyr Ser Asp Tyr Trp Gly
            100                 105                 110

Gln Gly Thr Leu Val Thr Val Ser Ser
        115                 120
```

<210> SEQ ID NO 91
<211> LENGTH: 363
<212> TYPE: DNA
<213> ORGANISM: Artificial Sequence
<220> FEATURE:
<223> OTHER INFORMATION: synthetic

<400> SEQUENCE: 91

```
atggccgatg ttcagctggt ggaaagcggc ggcggcctgg ttcagcctgg tggttcactg    60
cgtctgagtt gtgcagcaag tgcagcctg tttacaatta atgctatggg ttggtatcgt   120
caggcaccgg gtaaacagcg cgaagaagtt gccgccatta ccagtggcgg tagcaccaat   180
tatgccgata gtgttaaagg tcgtttttacc tttagtcgcg ataccgcacg caataccgtg   240
tgcccgcaga tgaatagcct gaaaccggat cataccgccg tgtattattg caaagcactg   300
gtggttccgc cgaccccgta tagtgtgtat tggggccagg gtaccctggt gaccgtgagc   360
agc                                                                  363
```

<210> SEQ ID NO 92
<211> LENGTH: 121
<212> TYPE: PRT
<213> ORGANISM: Artificial Sequence
<220> FEATURE:
<223> OTHER INFORMATION: synthetic

<400> SEQUENCE: 92

```
Met Ala Asp Val Gln Leu Val Glu Ser Gly Gly Gly Leu Val Gln Pro
```

```
1               5                   10                  15
Gly Gly Ser Leu Arg Leu Ser Cys Ala Ala Ser Gly Ser Leu Phe Thr
                20                  25                  30

Ile Asn Ala Met Gly Trp Tyr Arg Gln Ala Pro Gly Lys Gln Arg Glu
            35                  40                  45

Glu Val Ala Ala Ile Thr Ser Gly Gly Ser Thr Asn Tyr Ala Asp Ser
    50                  55                  60

Val Lys Gly Arg Phe Thr Phe Ser Arg Asp Thr Ala Arg Asn Thr Val
65                  70                  75                  80

Cys Pro Gln Met Asn Ser Leu Lys Pro Asp His Thr Ala Val Tyr Tyr
                85                  90                  95

Cys Lys Ala Leu Val Val Pro Pro Thr Pro Tyr Ser Val Tyr Trp Gly
                100                 105                 110

Gln Gly Thr Leu Val Thr Val Ser Ser
            115                 120
```

<210> SEQ ID NO 93
<211> LENGTH: 342
<212> TYPE: DNA
<213> ORGANISM: Artificial Sequence
<220> FEATURE:
<223> OTHER INFORMATION: synthetic

<400> SEQUENCE: 93

```
atggccgatg tgcagctggt gcagccgggt ggtagcctgc gtctgagctg tgccgccagt    60
ggcagtattt ttacaattaa tgctatgggt tggtaccgcc aggcaccggg taaacagcgt   120
gaagaagttg cagccattac cagcggcggt agcaccaatt atgcagatag cgtgaaaggc   180
cgttttacca ttagtcgtga taatgccaaa ataccgtgt atctgcagat gaatagcctg    240
aaaccggaag ataccgcagt ttattattgc aaagccgttg ttgttaccac cccccgtat    300 agcgattatt ggggtcaggg caccctggtt accgttagca gt                      342
```

<210> SEQ ID NO 94
<211> LENGTH: 114
<212> TYPE: PRT
<213> ORGANISM: Artificial Sequence
<220> FEATURE:
<223> OTHER INFORMATION: synthetic

<400> SEQUENCE: 94

```
Met Ala Asp Val Gln Leu Val Gln Pro Gly Gly Ser Leu Arg Leu Ser
1               5                   10                  15

Cys Ala Ala Ser Gly Ser Ile Phe Thr Ile Asn Ala Met Gly Trp Tyr
                20                  25                  30

Arg Gln Ala Pro Gly Lys Gln Arg Glu Glu Val Ala Ala Ile Thr Ser
            35                  40                  45

Gly Gly Ser Thr Asn Tyr Ala Asp Ser Val Lys Gly Arg Phe Thr Ile
    50                  55                  60

Ser Arg Asp Asn Ala Lys Asn Thr Val Tyr Leu Gln Met Asn Ser Leu
65                  70                  75                  80

Lys Pro Glu Asp Thr Ala Val Tyr Tyr Cys Lys Ala Val Val Val Thr
                85                  90                  95

Thr Thr Pro Tyr Ser Asp Tyr Trp Gly Gln Gly Thr Leu Val Thr Val
                100                 105                 110

Ser Ser
```

```
<210> SEQ ID NO 95
<211> LENGTH: 363
<212> TYPE: DNA
<213> ORGANISM: Artificial Sequence
<220> FEATURE:
<223> OTHER INFORMATION: synthetic

<400> SEQUENCE: 95
atggccgatg tgcagctggt tgaaagtggc ggcggtctgg ttcagccggg cggtagctta     60
cgcctgagtt gcgcagcaag tggcagtatt tttacaatta atgctatggg ttggtaccgt    120
caggccccgg gtaaacagcg tgaagaagtg gccgccagta ccagcggcgg tagccctaat    180
tatgatgata gcgttaaagg cccgtttaat ctgagtaaag ataatgcaaa aaacaccgtt    240
tacctgcaga ttaatcgtct gaaaccggaa gataccgccg tgtatttctt taaagcaggc    300
ggtggcagca gtaccccgga tagtgattat tggggtcagg gcaccctggt taccgttagt    360
agc                                                                  363

<210> SEQ ID NO 96
<211> LENGTH: 121
<212> TYPE: PRT
<213> ORGANISM: Artificial Sequence
<220> FEATURE:
<223> OTHER INFORMATION: synthetic

<400> SEQUENCE: 96

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ser Thr Ser Gly Gly Ser Pro Asn Tyr Asp Asp Ser
    50                  55                  60

Val Lys Gly Pro Phe Asn Leu Ser Lys Asp Asn Ala Lys Asn Thr Val
65                  70                  75                  80

Tyr Leu Gln Ile Asn Arg Leu Lys Pro Glu Asp Thr Ala Val Tyr Phe
                85                  90                  95

Phe Lys Ala Gly Gly Gly Ser Ser Thr Pro Asp Ser Asp Tyr Trp Gly
            100                 105                 110

Gln Gly Thr Leu Val Thr Val Ser Ser
        115                 120

<210> SEQ ID NO 97
<211> LENGTH: 498
<212> TYPE: DNA
<213> ORGANISM: Artificial Sequence
<220> FEATURE:
<223> OTHER INFORMATION: synthetic

<400> SEQUENCE: 97
atggccgatg ttcagctggt tgaaagcggt ggcggcctgg ttcagccggg tggtagtctg     60
cgcctgagct gcgctgcaag cggtagcatt tttacctcaa atgctatggg ttggtatcgt    120
caggccccgg gcaaacagcg cgaagaagtg gccgcaatta ccagtggcgg cagtaccaat    180
tatgccgata gcgtgaaagg ccgttttacc attagccgcg ataatgccaa aaataaggat    240
atgggttggt accgccaggc accgggtaaa cagcgtgaag aagtggcagc cattaccagc    300
ggcggtagca ccaattatgc ggatagcgtt aaaggtcgct ttaccattag tcgtgataat    360
```

```
gccaagaata ccgtgtatct gcagatgaat agtctgaaac cggaagatac cgccgtgtat      420
tattgtaaag cagtggtggt taccaccacc ccgtatagcg attattgggg tcagggtacc      480
ctggtgaccg tgagcagt                                                   498
```

<210> SEQ ID NO 98
<211> LENGTH: 166
<212> TYPE: PRT
<213> ORGANISM: Artificial Sequence
<220> FEATURE:
<223> OTHER INFORMATION: synthetic

<400> SEQUENCE: 98

```
Met Ala Asp Val Gln Leu Val Glu Ser Gly Gly Gly Leu Val Gln Pro
1               5                  10                  15

Gly Gly Ser Leu Arg Leu Ser Cys Ala Ala Ser Gly Ser Ile Phe Thr
            20                  25                  30

Ser Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Lys Asn Lys Asp
65                  70                  75                  80

Met Gly Trp Tyr Arg Gln Ala Pro Gly Lys Gln Arg Glu Glu Val Ala
                85                  90                  95

Ala Ile Thr Ser Gly Gly Ser Thr Asn Tyr Ala Asp Ser Val Lys Gly
            100                 105                 110

Arg Phe Thr Ile Ser Arg Asp Asn Ala Lys Asn Thr Val Tyr Leu Gln
        115                 120                 125

Met Asn Ser Leu Lys Pro Glu Asp Thr Ala Val Tyr Tyr Cys Lys Ala
    130                 135                 140

Val Val Val Thr Thr Thr Pro Tyr Ser Asp Tyr Trp Gly Gln Gly Thr
145                 150                 155                 160

Leu Val Thr Val Ser Ser
            165
```

<210> SEQ ID NO 99
<211> LENGTH: 414
<212> TYPE: DNA
<213> ORGANISM: Artificial Sequence
<220> FEATURE:
<223> OTHER INFORMATION: synthetic

<400> SEQUENCE: 99

```
atggccgatg tgcagccggt ggaaagtggt ggcggtctgg tgcagccggg tggttcactg      60
cgtctgagtt gcgcagccag tggcagcatt tttacaatta atgctatggg ttggtaccgt     120
caggcaccgg gcaaacagcg tgaagaagtt gcagcaatta ccagcggcgg cagtaccaat     180
tatgccgata gtgtgaaagg ccgctttacc attagccgtg ataatgccaa aaataccgtg     240
tatctgcaga tgaatagcct gaaaccggaa gataccgcca aaatacagt ttatctgaaa     300 atgaacagcc tgaaacctga agaaaccgcc gtgtattatt gcaaagccgt tgttgttacc     360 accacccgt atagcgatta ttggggccag ggcacccctgg ttaccgtgtg tagc           414
```

<210> SEQ ID NO 100
<211> LENGTH: 138
<212> TYPE: PRT
<213> ORGANISM: Artificial Sequence
<220> FEATURE:

<223> OTHER INFORMATION: synthetic

<400> SEQUENCE: 100

Met Ala Asp Val Gln Pro Val Glu Ser Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Lys Asn Thr
                85                  90                  95

Val Tyr Leu Lys Met Asn Ser Leu Lys Pro Glu Glu Thr Ala Val Tyr
            100                 105                 110

Tyr Cys Lys Ala Val Val Val Thr Thr Thr Pro Tyr Ser Asp Tyr Trp
        115                 120                 125

Gly Gln Gly Thr Leu Val Thr Val Cys Ser
    130                 135

<210> SEQ ID NO 101
<211> LENGTH: 453
<212> TYPE: DNA
<213> ORGANISM: Artificial Sequence
<220> FEATURE:
<223> OTHER INFORMATION: synthetic

<400> SEQUENCE: 101
atggccgatg ttcagctggt tgaaagtggt ggcggcctgg tgcagccggg ttggagctta    60
cgcctgagtt gcgccgcaag tggtagcatt tttacaatta atgctatggg ttggtaccgt   120
caggcaccgg ttaaacagcg tgaagaagtt gccgccatta ccagcggtgg cagcaccaat   180
tatgccgatc cggtgaaagg ttggtatcgt caggcacctg gtaaacagcg tgaggaagtt   240
gccgcgatta ccctggtggg tagtaccaat tatgcggata gtgtgaaagg ccgctttaat   300
attagtcgtg ataatgcaaa aaacaccgtt tatctgcaga tgaatagcct gaaaccggaa   360
gataccgcag tgtattattg taaagcagtg gttgtgacca ccaccccgga agcagattat   420
tggggccagg gcaccctggt gaccgttagt agt                                 453

<210> SEQ ID NO 102
<211> LENGTH: 151
<212> TYPE: PRT
<213> ORGANISM: Artificial Sequence
<220> FEATURE:
<223> OTHER INFORMATION: synthetic

<400> SEQUENCE: 102

Met Ala Asp Val Gln Leu Val Glu Ser Gly Gly Gly Leu Val Gln Pro
1               5                   10                  15

Gly Trp Ser Leu Arg Leu Ser Cys Ala Ala Ser Gly Ser Ile Phe Thr
            20                  25                  30

Ile Asn Ala Met Gly Trp Tyr Arg Gln Ala Pro Val Lys Gln Arg Glu
        35                  40                  45

Glu Val Ala Ala Ile Thr Ser Gly Gly Ser Thr Asn Tyr Ala Asp Pro
    50                  55                  60

Val Lys Gly Trp Tyr Arg Gln Ala Pro Gly Lys Gln Arg Glu Val
 65                  70                  75                  80

Ala Ala Ile Thr Leu Val Gly Ser Thr Asn Tyr Ala Asp Ser Val Lys
                 85                  90                  95

Gly Arg Phe Asn Ile Ser Arg Asp Asn Ala Lys Asn Thr Val Tyr Leu
            100                 105                 110

Gln Met Asn Ser Leu Lys Pro Glu Asp Thr Ala Val Tyr Tyr Cys Lys
        115                 120                 125

Ala Val Val Val Thr Thr Thr Pro Glu Ala Asp Tyr Trp Gly Gln Gly
    130                 135                 140

Thr Leu Val Thr Val Ser Ser
145                 150

<210> SEQ ID NO 103
<211> LENGTH: 342
<212> TYPE: DNA
<213> ORGANISM: Artificial Sequence
<220> FEATURE:
<223> OTHER INFORMATION: synthetic

<400> SEQUENCE: 103
atggccgatg ttcagctggt ggaaagtggt ggtagcctgc gtctgagttg cgcagccagt       60
ggtagcattt ttacaattaa tgctatgggt tggtaccgcc aggcaccggg taaacagcgc      120
gaagaagttg ccgcaattac cagcggtggt agtaccaatt atgcagatag cgtgaaaggt      180
cgttttacca ttagtcgtga taatgcaaaa acaccgttt atctgcagat gaatagtctg       240
aaaccggaag ataccgccgt gtattattgc aaagcagttg ttgttaccac cacccctat       300 agtgattatt ggggtcaggg caccctggtg accgtgagta gt                        342

<210> SEQ ID NO 104
<211> LENGTH: 114
<212> TYPE: PRT
<213> ORGANISM: Artificial Sequence
<220> FEATURE:
<223> OTHER INFORMATION: synthetic

<400> SEQUENCE: 104

Met Ala Asp Val Gln Leu Val Glu Ser Gly Gly Ser Leu Arg Leu Ser
1               5                   10                  15

Cys Ala Ala Ser Gly Ser Ile Phe Thr Ile Asn Ala Met Gly Trp Tyr
            20                  25                  30

Arg Gln Ala Pro Gly Lys Gln Arg Glu Glu Val Ala Ala Ile Thr Ser
        35                  40                  45

Gly Gly Ser Thr Asn Tyr Ala Asp Ser Val Lys Gly Arg Phe Thr Ile
    50                  55                  60

Ser Arg Asp Asn Ala Lys Asn Thr Val Tyr Leu Gln Met Asn Ser Leu
65                  70                  75                  80

Lys Pro Glu Asp Thr Ala Val Tyr Tyr Cys Lys Ala Val Val Val Thr
                85                  90                  95

Thr Thr Pro Tyr Ser Asp Tyr Trp Gly Gln Gly Thr Leu Val Thr Val
            100                 105                 110

Ser Ser

<210> SEQ ID NO 105
<211> LENGTH: 396
<212> TYPE: DNA
<213> ORGANISM: Artificial Sequence
<220> FEATURE:

<223> OTHER INFORMATION: synthetic

<400> SEQUENCE: 105

```
atggccgatg ttcagctggt ggaaagcggt ggtggtctgg ttcagccggg tggtagcctg      60
cgcctgagct gtgcagccag tggtagcatt tttacaatta atgctatggg ttggtaccgt     120
caggccccgg gtaaacagcg tgaagaagtg gccgcaatta ccagtggtgg cagtaccaat     180
tatgaagata gcgttaccgg tcgctttacc attagccgcg ataccgttaa aggtcgcttt     240
acaattaccc gtgataatgc aaaaaacacc gtgtatctgc agatgaatag cctgaaaccg     300
gaagataccg cagttttatta ttgtaaagcc gttgttgtta ccaccacccc gtatagcgat     360
tattggggcc agggcaccct ggtgaccgtg tcaagc                                396
```

<210> SEQ ID NO 106
<211> LENGTH: 132
<212> TYPE: PRT
<213> ORGANISM: Artificial Sequence
<220> FEATURE:
<223> OTHER INFORMATION: synthetic

<400> SEQUENCE: 106

Met Ala Asp Val Gln Leu Val Glu Ser Gly Gly Gly Leu Val Gln Pro
1               5                   10                  15
Gly Gly Ser Leu Arg Leu Ser Cys Ala Ala Ser Gly Ser Ile Phe Thr
            20                  25                  30
Ile Asn Ala Met Gly Trp Tyr Arg Gln Ala Pro Gly Lys Gln Arg Glu
        35                  40                  45
Glu Val Ala Ala Ile Thr Ser Gly Gly Ser Thr Asn Tyr Glu Asp Ser
    50                  55                  60
Val Thr Gly Arg Phe Thr Ile Ser Arg Asp Thr Val Lys Gly Arg Phe
65                  70                  75                  80
Thr Ile Thr Arg Asp Asn Ala Lys Asn Thr Val Tyr Leu Gln Met Asn
                85                  90                  95
Ser Leu Lys Pro Glu Asp Thr Ala Val Tyr Tyr Cys Lys Ala Val Val
            100                 105                 110
Val Thr Thr Thr Pro Tyr Ser Asp Tyr Trp Gly Gln Gly Thr Leu Val
        115                 120                 125
Thr Val Ser Ser
    130

<210> SEQ ID NO 107
<211> LENGTH: 363
<212> TYPE: DNA
<213> ORGANISM: Artificial Sequence
<220> FEATURE:
<223> OTHER INFORMATION: synthetic

<400> SEQUENCE: 107

```
atggccgatg tgcagctggt ggaaagcggc ggtggcctgg tgcagcctgg tggttcactg      60
cgcctgagtt gtgcagcaag tggtagcatt tttacaatta atgctatggg ttggtaccgc     120
caggccccgg gtaaacagcg cgaagaagtt gccgccatta ccagcggtgg ccgcaccaat     180
tatgcagata gtgtgaaagg tcgctttacc attccgcgtg ataatgcacg taataccgtg     240
tatctgcaga tgaatagtct gaatccggaa ggcgccgatg tgtatagctg taaagccgtt     300
gttgttacca ccaccccgta tagcgatagt tggggtcagg gtccgctggt gaccgtttat     360
agt                                                                    363
```

<210> SEQ ID NO 108
<211> LENGTH: 121
<212> TYPE: PRT
<213> ORGANISM: Artificial Sequence
<220> FEATURE:
<223> OTHER INFORMATION: synthetic

<400> SEQUENCE: 108

```
Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Thr
            20                  25                  30

Ile Asn Ala Met Gly Trp Tyr Arg Gln Ala Pro Gly Lys Gln Arg Glu
        35                  40                  45

Glu Val Ala Ala Ile Thr Ser Gly Gly Arg Thr Asn Tyr Ala Asp Ser
50                  55                  60

Val Lys Gly Arg Phe Thr Ile Pro Arg Asp Asn Ala Arg Asn Thr Val
65                  70                  75                  80

Tyr Leu Gln Met Asn Ser Leu Asn Pro Glu Gly Ala Asp Val Tyr Ser
                85                  90                  95

Cys Lys Ala Val Val Val Thr Thr Pro Tyr Ser Asp Ser Trp Gly
            100                 105                 110

Gln Gly Pro Leu Val Thr Val Tyr Ser
        115                 120
```

<210> SEQ ID NO 109
<211> LENGTH: 17
<212> TYPE: PRT
<213> ORGANISM: Artificial Sequence
<220> FEATURE:
<223> OTHER INFORMATION: synthetic

<400> SEQUENCE: 109

```
Ala His His Ser Glu Asp Pro Ser Ser Lys Ala Pro Lys Ala Pro Met
1               5                   10                  15

Ala
```

<210> SEQ ID NO 110
<211> LENGTH: 15
<212> TYPE: PRT
<213> ORGANISM: Artificial Sequence
<220> FEATURE:
<223> OTHER INFORMATION: synthetic

<400> SEQUENCE: 110

```
Gly Gly Gly Gly Ser Gly Gly Gly Gly Ser Gly Gly Gly Gly Ser
1               5                   10                  15
```

<210> SEQ ID NO 111
<211> LENGTH: 363
<212> TYPE: DNA
<213> ORGANISM: Artificial Sequence
<220> FEATURE:
<223> OTHER INFORMATION: synthetic

<400> SEQUENCE: 111

```
atggcccagg ttcagctgca agagagcggt gggggcctgg tacagccggg cgggagcttg    60
cgcctgtcct gtgcggcatc aggtaatatc ttttcaatta acgcgattgg atggtaccgc   120
caagccccgg ggaaacagcg tgagctggtg gccaccatta ccctctcagg ttccaccaac   180
tacgctgatt ctgtcaaagg cgctttagc atttcacgcg acaatgcaaa aaataccgtg   240
```

```
tacctgcaaa tgaattctct taaaccagaa gacactgccg tctattattg caacgcgaac    300
acatattcgg acagtgacgt gtatggttat tggggacagg gtacgcaggt caccgtctcg    360
agc                                                                  363
```

<210> SEQ ID NO 112
<211> LENGTH: 121
<212> TYPE: PRT
<213> ORGANISM: Artificial Sequence
<220> FEATURE:
<223> OTHER INFORMATION: synthetic

<400> SEQUENCE: 112

```
Met Ala Gln Val Gln Leu Gln Glu Ser Gly Gly Gly Leu Val Gln Pro
1               5                   10                  15

Gly Gly Ser Leu Arg Leu Ser Cys Ala Ala Ser Gly Asn Ile Phe Ser
            20                  25                  30

Ile Asn Ala Ile Gly Trp Tyr Arg Gln Ala Pro Gly Lys Gln Arg Glu
        35                  40                  45

Leu Val Ala Thr Ile Thr Leu Ser Gly Ser Thr Asn Tyr Ala Asp Ser
    50                  55                  60

Val Lys Gly Arg Phe Ser Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Ala Asn Thr Tyr Ser Asp Ser Asp Val Tyr Gly Tyr Trp Gly
            100                 105                 110

Gln Gly Thr Gln Val Thr Val Ser Ser
        115                 120
```

<210> SEQ ID NO 113
<211> LENGTH: 45
<212> TYPE: DNA
<213> ORGANISM: Artificial Sequence
<220> FEATURE:
<223> OTHER INFORMATION: synthetic

<400> SEQUENCE: 113

```
gcacaccata gtgaagatcc ctcgtccaaa gcccccaaag caccg                    45
```

<210> SEQ ID NO 114
<211> LENGTH: 639
<212> TYPE: DNA
<213> ORGANISM: Artificial Sequence
<220> FEATURE:
<223> OTHER INFORMATION: synthetic

<400> SEQUENCE: 114

```
atggcaatca catgcccgcc gccgatgtca gtcgaacatg cggacatttg gtcaaaagc     60 tactccttat acagtcgcga gcgttatatc tgcaactccg gcttcaagcg caaagcgggc   120
accagttctc tgacggaatg tgtactgaat aaagctacaa atgtggctca ctggacgacc   180
cctagcctga atgtattcg cgaccccggcc ctggtacatc agcgtccggc gccgccgtca   240
ggggggtccg gtggcggagg ctccggggga ggatctggcg ggggaggtag cttacaaaat   300
tgggtcaacg ttatcagcga tctgaagaaa attgaagact taattcagag catgcacatc   360
gacgccaccc tgtacacgga aagcgatgtg cacccatcct gtaaagtcac agccatgaaa   420
tgctttctct tggaacttca ggtaattagc ctggaatccg gtgatgcaag cattcatgat   480
```

```
acggtcgaaa atttgattat tcttgcgaac aattctctgt ccagtaatgg gaacgtcacg      540
gaaagcggct gtaaggagtg cgaagaactg gaggagaaaa acattaaaga atttctgcag      600
agcttcgtgc atatcgtgca gatgttcatc aacacatca                             639
```

<210> SEQ ID NO 115
<211> LENGTH: 213
<212> TYPE: PRT
<213> ORGANISM: Artificial Sequence
<220> FEATURE:
<223> OTHER INFORMATION: synthetic

<400> SEQUENCE: 115

```
Met Ala Ile Thr Cys Pro Pro Met Ser Val Glu His Ala Asp Ile
1               5                   10                  15

Trp Val Lys Ser Tyr Ser Leu Tyr Ser Arg Glu Arg Tyr Ile Cys Asn
            20                  25                  30

Ser Gly Phe Lys Arg Lys Ala Gly Thr Ser Ser Leu Thr Glu Cys Val
        35                  40                  45

Leu Asn Lys Ala Thr Asn Val Ala His Trp Thr Thr Pro Ser Leu Lys
    50                  55                  60

Cys Ile Arg Asp Pro Ala Leu Val His Gln Arg Pro Ala Pro Pro Ser
65                  70                  75                  80

Gly Gly Ser Gly Gly Gly Gly Ser Gly Gly Gly Ser Gly Gly Gly Gly
                85                  90                  95

Ser Leu Gln Asn Trp Val Asn Val Ile Ser Asp Leu Lys Lys Ile Glu
            100                 105                 110

Asp Leu Ile Gln Ser Met His Ile Asp Ala Thr Leu Tyr Thr Glu Ser
        115                 120                 125

Asp Val His Pro Ser Cys Lys Val Thr Ala Met Lys Cys Phe Leu Leu
    130                 135                 140

Glu Leu Gln Val Ile Ser Leu Glu Ser Gly Asp Ala Ser Ile His Asp
145                 150                 155                 160

Thr Val Glu Asn Leu Ile Ile Leu Ala Asn Asn Ser Leu Ser Ser Asn
                165                 170                 175

Gly Asn Val Thr Glu Ser Gly Cys Lys Glu Cys Glu Glu Leu Glu Glu
            180                 185                 190

Lys Asn Ile Lys Glu Phe Leu Gln Ser Phe Val His Ile Val Gln Met
        195                 200                 205

Phe Ile Asn Thr Ser
    210
```

<210> SEQ ID NO 116
<211> LENGTH: 348
<212> TYPE: DNA
<213> ORGANISM: Artificial Sequence
<220> FEATURE:
<223> OTHER INFORMATION: synthetic

<400> SEQUENCE: 116

```
atggcaaaact gggtgaacgt tatcagcgac ctgaagaaaa tcgaggatct gattcagagc      60
atgcacattg acgcgaccct gtacaccgaa agcgatgtgc acccgagctg caaggttacc     120
gcgatgaaat gcttcctgct ggagctgcaa gtgatcagcc tggaaagcgg tgacgcgagc     180
attcacgata ccgttgagaa cctgatcatt ctggcgaaca acagcctgag cagcaacggt     240
aacgtgaccg agagcggctg caaggaatgc gaggaactgg aggaaaagaa catcaaagaa     300
ttcctgcaga gctttgtgca catcgttcaa atgtttatta acaccagc                  348
```

<210> SEQ ID NO 117
<211> LENGTH: 116
<212> TYPE: PRT
<213> ORGANISM: Artificial Sequence
<220> FEATURE:
<223> OTHER INFORMATION: synthetic

<400> SEQUENCE: 117

```
Met Ala Asn Trp Val Asn Val Ile Ser Asp Leu Lys Lys Ile Glu Asp
1               5                   10                  15

Leu Ile Gln Ser Met His Ile Asp Ala Thr Leu Tyr Thr Glu Ser Asp
            20                  25                  30

Val His Pro Ser Cys Lys Val Thr Ala Met Lys Cys Phe Leu Leu Glu
        35                  40                  45

Leu Gln Val Ile Ser Leu Glu Ser Gly Asp Ala Ser Ile His Asp Thr
    50                  55                  60

Val Glu Asn Leu Ile Ile Leu Ala Asn Asn Ser Leu Ser Ser Asn Gly
65                  70                  75                  80

Asn Val Thr Glu Ser Gly Cys Lys Glu Cys Glu Glu Leu Glu Glu Lys
                85                  90                  95

Asn Ile Lys Glu Phe Leu Gln Ser Phe Val His Ile Val Gln Met Phe
            100                 105                 110

Ile Asn Thr Ser
        115
```

<210> SEQ ID NO 118
<211> LENGTH: 408
<212> TYPE: DNA
<213> ORGANISM: Artificial Sequence
<220> FEATURE:
<223> OTHER INFORMATION: synthetic

<400> SEQUENCE: 118

```
atggcagcgc cgaccagcag cagcaccaag aaaacccagc tgcaactgga acacctgctg      60
ctggacctgc agatgattct gaacggtatc aacaactaca agaacccgaa actgacccgt     120
atgctgacct tcaagtttta tatgccgaag aaagcgaccg agctgaagca cctgcagtgc     180
ctggaggaag agctgaaacc gctggaagag gtgctgaacc tggcgcaaag caagaacttc     240
cacctgcgtc cgcgtgacct gatcagcaac attaacgtga cgttctggaa actgaaaggc     300
agcgaaacca ccttttatgt cgaatacgcg gatgaaaccg cgaccattgt tgaattcctg     360
aaccgttgga tcacctttg ccaaagcatc attagcaccc tgaccgag                   408
```

<210> SEQ ID NO 119
<211> LENGTH: 136
<212> TYPE: PRT
<213> ORGANISM: Artificial Sequence
<220> FEATURE:
<223> OTHER INFORMATION: synthetic

<400> SEQUENCE: 119

```
Met Ala Ala Pro Thr Ser Ser Ser Thr Lys Lys Thr Gln Leu Gln Leu
1               5                   10                  15

Glu His Leu Leu Leu Asp Leu Gln Met Ile Leu Asn Gly Ile Asn Asn
            20                  25                  30

Tyr Lys Asn Pro Lys Leu Thr Arg Met Leu Thr Phe Lys Phe Tyr Met
        35                  40                  45

Pro Lys Lys Ala Thr Glu Leu Lys His Leu Gln Cys Leu Glu Glu Glu
```

```
            50                  55                  60
Leu Lys Pro Leu Glu Glu Val Leu Asn Leu Ala Gln Ser Lys Asn Phe
 65                  70                  75                  80

His Leu Arg Pro Arg Asp Leu Ile Ser Asn Ile Asn Val Ile Val Leu
                 85                  90                  95

Glu Leu Lys Gly Ser Glu Thr Thr Phe Met Cys Glu Tyr Ala Asp Glu
            100                 105                 110

Thr Ala Thr Ile Val Gly Phe Leu Asn Arg Trp Ile Thr Phe Ala Gln
        115                 120                 125

Ser Ile Ile Ser Thr Leu Thr Glu
        130                 135

<210> SEQ ID NO 120
<211> LENGTH: 785
<212> TYPE: DNA
<213> ORGANISM: Artificial Sequence
<220> FEATURE:
<223> OTHER INFORMATION: synthetic

<400> SEQUENCE: 120
atggaagtgc aactggtgga gagcggcggt ggtctggtgc aaccgggtcg tagcctgaaa      60
ctgagctgcg cggcgagcgg ctttaccttt agcaactacg atatggcgtg ggttcgtcag     120
gcgccggata ccaagtgcct ggagtgggtt gcgagcatca gcccgagcgg tgatatcacc     180
tattaccgtg atagcgtgaa aggtcgtttt accgttagcc gtgataacac caaaagcacc     240
ctgtttctgc agatggatag cctgcgtagc gaagataccg cgacctatta ctgcgcgcgt     300
cacggcccga ccgaagcgcc ggatattatg acgcgtgggg tcaaggcgc gagcgttacc      360 gtgagcagcg ctggtggtgg cagcggtggt ggcggtagcg gtggcggtgg tagcggcccg     420
cacatcctgg cggtgctgga tttctgggac attgtgatga cccaaagccc gagcagcctg     480
gcggttagcg cgggcgaaac cgttaccatc aactgcaaaa gcagccagag cctgctgtac     540
agcggtaacc agaagaacta cctggcgtgg taccagcaaa aaccgggtca gagcccgaag     600
ctgctgatcc actgggcgag cacccgtcaa agcggcgttc cggaccgttt cattggcagc     660
ggtagcggca ccgacttcac cctgaccatt agcagcgtgc aagcggagga tctggcgatc     720
tattactgcc agcaatatta cgacagcccg ctgacctttg gtagcggtac caagctggag     780
attaa                                                                  785

<210> SEQ ID NO 121
<211> LENGTH: 262
<212> TYPE: PRT
<213> ORGANISM: Artificial Sequence
<220> FEATURE:
<223> OTHER INFORMATION: synthetic

<400> SEQUENCE: 121

Met Glu Val Gln Leu Val Glu Ser Gly Gly Gly Leu Val Gln Pro Gly
 1               5                  10                  15

Arg Ser Leu Lys Leu Ser Cys Ala Ala Ser Gly Phe Thr Phe Ser Asn
             20                  25                  30

Tyr Asp Met Ala Trp Val Arg Gln Ala Pro Asp Thr Lys Cys Leu Glu
         35                  40                  45

Trp Val Ala Ser Ile Ser Pro Ser Gly Asp Ile Thr Tyr Tyr Arg Asp
     50                  55                  60

Ser Val Lys Gly Arg Phe Thr Val Ser Arg Asp Asn Thr Lys Ser Thr
 65                  70                  75                  80
```

```
Leu Phe Leu Gln Met Asp Ser Leu Arg Ser Glu Asp Thr Ala Thr Tyr
                85                  90                  95

Tyr Cys Ala Arg His Gly Pro Thr Glu Ala Pro Asp Ile Met Asp Ala
            100                 105                 110

Trp Gly Gln Gly Ala Ser Val Thr Val Ser Ser Gly Gly Gly Gly Ser
        115                 120                 125

Gly Gly Gly Gly Ser Gly Gly Gly Ser Gly Pro His Ile Leu Ala
    130                 135                 140

Val Leu Asp Phe Trp Asp Ile Val Met Thr Gln Ser Pro Ser Ser Leu
145                 150                 155                 160

Ala Val Ser Ala Gly Glu Thr Val Thr Ile Asn Cys Lys Ser Ser Gln
                165                 170                 175

Ser Leu Leu Tyr Ser Gly Asn Gln Lys Asn Tyr Leu Ala Trp Tyr Gln
            180                 185                 190

Gln Lys Pro Gly Gln Ser Pro Lys Leu Leu Ile His Trp Ala Ser Thr
        195                 200                 205

Arg Gln Ser Gly Val Pro Asp Arg Phe Ile Gly Ser Gly Ser Gly Thr
    210                 215                 220

Asp Phe Thr Leu Thr Ile Ser Ser Val Gln Ala Glu Asp Leu Ala Ile
225                 230                 235                 240

Tyr Tyr Cys Gln Gln Tyr Tyr Asp Ser Pro Leu Thr Phe Gly Ser Gly
                245                 250                 255

Thr Lys Leu Glu Ile Lys
            260

<210> SEQ ID NO 122
<211> LENGTH: 124
<212> TYPE: PRT
<213> ORGANISM: Artificial Sequence
<220> FEATURE:
<223> OTHER INFORMATION: synthetic

<400> SEQUENCE: 122

Met Ala Gln Val Gln Leu Gln Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Asn Tyr Tyr Met Gly Trp Phe Arg Gln Ala Pro Gly Lys Glu Arg Glu
        35                  40                  45

Phe Val Ala Thr Ile Ser Gln Ser Gly Ser Ile Thr Tyr Tyr Ala Asp
    50                  55                  60

Ser Val Lys Gly Arg Phe Thr Ile Ser Arg Asp Asn Ala Lys Asn Thr
65                  70                  75                  80

Val Ser Leu Gln Met Asn Ser Leu Lys Pro Glu Asp Thr Ala Val Tyr
                85                  90                  95

Tyr Cys Ala Gly Asn Ser Phe Lys Ser Asn Asp His Trp Ala Ser Thr
            100                 105                 110

Tyr Trp Gly Gln Gly Thr Gln Val Thr Val Ser Ser
        115                 120

<210> SEQ ID NO 123
<211> LENGTH: 372
<212> TYPE: DNA
<213> ORGANISM: Artificial Sequence
<220> FEATURE:
<223> OTHER INFORMATION: synthetic
```

<400> SEQUENCE: 123

```
atggcgcaag ttcaactgca agaaagcggc ggtggtctgg ttcaagcggg cggtagcctg      60
cgtctgagct gcgcggcgag cggtcgtacc ttcagcaact actatatggg ctggtttcgt     120
caagcgccgg gcaaggagcg tgaattcgtg gcgaccatca gccagagcgg cagcattacc     180
tactatgcgg acagcgttaa gggtcgtttt accatcagcc gtgataacgc gaaaaacacc     240
gtgagcctgc aaatgaacag cctgaagccg gaggacaccg cggtttacta ttgcgcgggc     300
aacagcttca aaagcaacga tcattgggcg agcaccTatt ggggccaagg tacccaggtg     360
accgtttctt ct                                                          372
```

<210> SEQ ID NO 124
<211> LENGTH: 471
<212> TYPE: DNA
<213> ORGANISM: Artificial Sequence
<220> FEATURE:
<223> OTHER INFORMATION: synthetic

<400> SEQUENCE: 124

```
aacttcggtc gtctgcactg caccaccgcg gttatccgta atatcaatga ccaggttctg      60
ttcgtggaca gcgccagcc ggttttcgaa gatatgaccg acatcgatca gagcgcgagc     120
gaaccgcaaa cccgtctgat tatctacatg tataaggata gcgaagttcg tggtctggcg     180
gttaccctga gcgtgaaaga cagcaagatg agcaccctga gctgcaaaaa caagatcatt     240
agcttcgagg aaatggaccc gccggaaaac atcgacgata tccaaagcga cctgatcttc     300
tttcagaagc gtgttccggg tcacaacaag atggaattcg agagcagcct gtacgaaggt     360
cacttcctgg cgtgccagaa agaggacgat gcgtttaagc tgatcctgaa gaagaaagac     420
gagaatggcg acaagagcgt tatgttcacc ctgaccaacc tgcaccaaag c              471
```

<210> SEQ ID NO 125
<211> LENGTH: 157
<212> TYPE: PRT
<213> ORGANISM: Artificial Sequence
<220> FEATURE:
<223> OTHER INFORMATION: synthetic

<400> SEQUENCE: 125

```
Asn Phe Gly Arg Leu His Cys Thr Thr Ala Val Ile Arg Asn Ile Asn
1               5                   10                  15
Asp Gln Val Leu Phe Val Asp Lys Arg Gln Pro Val Phe Glu Asp Met
            20                  25                  30
Thr Asp Ile Asp Gln Ser Ala Ser Glu Pro Gln Thr Arg Leu Ile Ile
        35                  40                  45
Tyr Met Tyr Lys Asp Ser Glu Val Arg Gly Leu Ala Val Thr Leu Ser
    50                  55                  60
Val Lys Asp Ser Lys Met Ser Thr Leu Ser Cys Lys Asn Lys Ile Ile
65                  70                  75                  80
Ser Phe Glu Glu Met Asp Pro Pro Glu Asn Ile Asp Asp Ile Gln Ser
                85                  90                  95
Asp Leu Ile Phe Phe Gln Lys Arg Val Pro Gly His Asn Lys Met Glu
            100                 105                 110
Phe Glu Ser Ser Leu Tyr Glu Gly His Phe Leu Ala Cys Gln Lys Glu
        115                 120                 125
Asp Asp Ala Phe Lys Leu Ile Leu Lys Lys Lys Asp Glu Asn Gly Asp
    130                 135                 140
```

-continued

Lys Ser Val Met Phe Thr Leu Thr Asn Leu His Gln Ser
145                 150                 155

<210> SEQ ID NO 126
<211> LENGTH: 408
<212> TYPE: DNA
<213> ORGANISM: Artificial Sequence
<220> FEATURE:
<223> OTHER INFORMATION: synthetic

<400> SEQUENCE: 126

| | |
|---|---|
| atggcagcgc cgaccagcag cagcaccaag aaaacccagc tgcaactgga acacctgctg | 60 |
| ctggacctgc agatgattct gaacggtatc aacaactaca agaacccgaa actgacccgt | 120 |
| atgctgacct tcaagtttta tgccgaaag aaagcgaccg agctgaagca cctgcagtgc | 180 |
| ctggaggaag agctgaaacc gctggaagag gtgctgaacc tggcgcaaag caagaacttc | 240 |
| cacctgcgtc cgcgtgacct gatcagcaac attaacgtga tcgttctgga actgaaaggc | 300 |
| agcgaaacca cctttatgtg cgaatacgcg gatgaaaccg cgaccattgt tgaattcctg | 360 |
| aaccgttgga tcacctttgc gcaaagcatc attagcaccc tgaccgag | 408 |

<210> SEQ ID NO 127
<211> LENGTH: 136
<212> TYPE: PRT
<213> ORGANISM: Artificial Sequence
<220> FEATURE:
<223> OTHER INFORMATION: synthetic

<400> SEQUENCE: 127

Met Ala Ala Pro Thr Ser Ser Thr Lys Lys Thr Gln Leu Gln Leu
1               5                   10                  15

Glu His Leu Leu Leu Asp Leu Gln Met Ile Leu Asn Gly Ile Asn Asn
            20                  25                  30

Tyr Lys Asn Pro Lys Leu Thr Arg Met Leu Thr Phe Lys Phe Tyr Met
        35                  40                  45

Pro Lys Lys Ala Thr Glu Leu Lys His Leu Gln Cys Leu Glu Glu Glu
    50                  55                  60

Leu Lys Pro Leu Glu Glu Val Leu Asn Leu Ala Gln Ser Lys Asn Phe
65                  70                  75                  80

His Leu Arg Pro Arg Asp Leu Ile Ser Asn Ile Asn Val Ile Leu
            85                  90                  95

Glu Leu Lys Gly Ser Glu Thr Thr Phe Met Cys Glu Tyr Ala Asp Glu
            100                 105                 110

Thr Ala Thr Ile Val Glu Phe Leu Asn Arg Trp Ile Thr Phe Ala Gln
        115                 120                 125

Ser Ile Ile Ser Thr Leu Thr Glu
    130                 135

<210> SEQ ID NO 128
<211> LENGTH: 480
<212> TYPE: DNA
<213> ORGANISM: Artificial Sequence
<220> FEATURE:
<223> OTHER INFORMATION: synthetic

<400> SEQUENCE: 128

| | |
|---|---|
| atggcagtgc gtagcagcag ccgtaccccg agcgacaagc cggttgcgca tgtggttgcg | 60 |
| aacccgcagg cggagggtca gctgcaatgg ctgaaccgtc gtgcgaacgc gctgctggcg | 120 |
| aacggtgtgg aactgcgtga taaccaactg gtggttccga gcgagggcct gtacctgatc | 180 |

```
tatagccagg tgctgttcaa aggtcaaggc tgcccgagca cccacgttct gctgacccac      240
accatcagcc gtattgcggt gagctaccag accaaggtta acctgctgag cgcgattaaa      300
agcccgtgcc aacgtgaaac cccggagggt gcggaggcga agccgtggta cgaaccgatc      360
tatctgggtg gcgtgtttca gctggaaaaa ggcgaccgtc tgagcgcgga gattaaccgt      420
ccggactacc tggatttcgc ggagagcggt caagtttatt ttggcatcat tgcgctggag      480
```

<210> SEQ ID NO 129
<211> LENGTH: 160
<212> TYPE: PRT
<213> ORGANISM: Artificial Sequence
<220> FEATURE:
<223> OTHER INFORMATION: synthetic

<400> SEQUENCE: 129

```
Met Ala Val Arg Ser Ser Arg Thr Pro Ser Asp Lys Pro Val Ala
1               5                   10                  15

His Val Val Ala Asn Pro Gln Ala Glu Gly Gln Leu Gln Trp Leu Asn
            20                  25                  30

Arg Arg Ala Asn Ala Leu Leu Ala Asn Gly Val Glu Leu Arg Asp Asn
        35                  40                  45

Gln Leu Val Val Pro Ser Glu Gly Leu Tyr Leu Ile Tyr Ser Gln Val
    50                  55                  60

Leu Phe Lys Gly Gln Gly Cys Pro Ser Thr His Val Leu Leu Thr His
65                  70                  75                  80

Thr Ile Ser Arg Ile Ala Val Ser Tyr Gln Thr Lys Val Asn Leu Leu
                85                  90                  95

Ser Ala Ile Lys Ser Pro Cys Gln Arg Glu Thr Pro Glu Gly Ala Glu
            100                 105                 110

Ala Lys Pro Trp Tyr Glu Pro Ile Tyr Leu Gly Gly Val Phe Gln Leu
        115                 120                 125

Glu Lys Gly Asp Arg Leu Ser Ala Glu Ile Asn Arg Pro Asp Tyr Leu
    130                 135                 140

Asp Phe Ala Glu Ser Gly Gln Val Tyr Phe Gly Ile Ile Ala Leu Glu
145                 150                 155                 160
```

<210> SEQ ID NO 130
<211> LENGTH: 465
<212> TYPE: DNA
<213> ORGANISM: Artificial Sequence
<220> FEATURE:
<223> OTHER INFORMATION: synthetic

<400> SEQUENCE: 130

```
atggcagact gcgatatcga gggcaaggac ggcaaacagt acgaaagcgt gctgatggtt      60
agcatcgacc aactgctgga tagcatgaag gagattggta gcaactgcct gaacaacgaa      120
ttcaacttct ttaagcgtca catttgcgat gcgaacaaag agggcatgtt cctgtttcgt      180
gcggcgcgta agctgcgtca gttcctgaaa atgaacagca ccggtgactt tgatctgcac      240
ctgctgaagg tgagcgaagg caccaccatc ctgctgaact gcaccggtca ggttaaaggt      300
cgtaaaccgg cggcgctggg cgaggcgcaa ccgaccaaaa gcctggagga aaacaagagc      360
ctgaaagaac agaagaaact gaacgacctg tgctttctga gcgtctgct gcaagagatc      420 aagacctgct ggaacaaaat tctgatgggc accaagaac acgag                       465
```

<210> SEQ ID NO 131

<211> LENGTH: 155
<212> TYPE: PRT
<213> ORGANISM: Artificial Sequence
<220> FEATURE:
<223> OTHER INFORMATION: synthetic

<400> SEQUENCE: 131

Met Ala Asp Cys Asp Ile Glu Gly Lys Asp Gly Lys Gln Tyr Glu Ser
1               5                   10                  15
Val Leu Met Val Ser Ile Asp Gln Leu Leu Asp Ser Met Lys Glu Ile
            20                  25                  30
Gly Ser Asn Cys Leu Asn Asn Glu Phe Asn Phe Phe Lys Arg His Ile
        35                  40                  45
Cys Asp Ala Asn Lys Glu Gly Met Phe Leu Phe Arg Ala Ala Arg Lys
    50                  55                  60
Leu Arg Gln Phe Leu Lys Met Asn Ser Thr Gly Asp Phe Asp Leu His
65                  70                  75                  80
Leu Leu Lys Val Ser Glu Gly Thr Thr Ile Leu Leu Asn Cys Thr Gly
                85                  90                  95
Gln Val Lys Gly Arg Lys Pro Ala Ala Leu Gly Glu Ala Gln Pro Thr
            100                 105                 110
Lys Ser Leu Glu Glu Asn Lys Ser Leu Lys Glu Gln Lys Lys Leu Asn
        115                 120                 125
Asp Leu Cys Phe Leu Lys Arg Leu Leu Gln Glu Ile Lys Thr Cys Trp
    130                 135                 140
Asn Lys Ile Leu Met Gly Thr Lys Glu His Glu
145                 150                 155

<210> SEQ ID NO 132
<211> LENGTH: 381
<212> TYPE: DNA
<213> ORGANISM: Artificial Sequence
<220> FEATURE:
<223> OTHER INFORMATION: synthetic

<400> SEQUENCE: 132
atggcacagg gtccggaccg tctgctgatc cgtctgcgtc acctgatcga tattgtggag      60
caactgaaaa tttacgaaaa cgacctggat ccggagctgc tgagcgcgcc gcaggacgtt     120
aagggtcact gcgaacacgc ggcgttcgcg tgctttcaaa aggcgaaact gaagccgagc     180
aacccgggca caacaaaac cttcatcatt gacctggttg cgcagctgcg tcgtcgtctg     240
ccggcgcgtc gtggtggcaa gaaacaaaaa cacatcgcga agtgcccgag ctgcgatagc     300
tatgagaaac gtaccccgaa ggagtttctg gaacgtctga atggctgct gcagaagatg     360
attcaccaac acctgagcga g                                              381

<210> SEQ ID NO 133
<211> LENGTH: 127
<212> TYPE: PRT
<213> ORGANISM: Artificial Sequence
<220> FEATURE:
<223> OTHER INFORMATION: synthetic

<400> SEQUENCE: 133

Met Ala Gln Gly Pro Asp Arg Leu Leu Ile Arg Leu Arg His Leu Ile
1               5                   10                  15
Asp Ile Val Glu Gln Leu Lys Ile Tyr Glu Asn Asp Leu Asp Pro Glu
            20                  25                  30
Leu Leu Ser Ala Pro Gln Asp Val Lys Gly His Cys Glu His Ala Ala

```
                35                  40                  45
Phe Ala Cys Phe Gln Lys Ala Lys Leu Lys Pro Ser Asn Pro Gly Asn
         50                  55                  60
Asn Lys Thr Phe Ile Ile Asp Leu Val Ala Gln Leu Arg Arg Arg Leu
 65                  70                  75                  80
Pro Ala Arg Arg Gly Gly Lys Lys Gln Lys His Ile Ala Lys Cys Pro
                 85                  90                  95
Ser Cys Asp Ser Tyr Glu Lys Arg Thr Pro Lys Glu Phe Leu Glu Arg
            100                 105                 110
Leu Lys Trp Leu Leu Gln Lys Met Ile His Gln His Leu Ser Glu
            115                 120                 125
```

<210> SEQ ID NO 134
<211> LENGTH: 507
<212> TYPE: DNA
<213> ORGANISM: Artificial Sequence
<220> FEATURE:
<223> OTHER INFORMATION: synthetic

<400> SEQUENCE: 134

```
atggcatgcg acctgccgca gacccacaac ctgcgtaaca agcgtgcgct gaccctgctg      60
gtgcaaatgc gtcgtctgag cccgctgagc tgcctgaagg accgtaaaga tttcggtttt     120
ccgcaggaga aggtggacgc gcagcaaatc aagaaagcgc aagcgattcc ggttctgagc     180
gaactgaccc agcaaatcct gaacattttc accagcaaag atagcagcgc ggcgtggaac     240
accaccctgc tggacagctt ttgcaacgat ctgcaccagc aactgaacga cctgcagggt     300
tgcctgatgc agcaagtggg cgttcaggag ttcccgctga cccaagaaga tgcgctgctg     360
gcggtgcgta agtactttca ccgtatcacc gtttatctgc gtgagaagaa acacagcccg     420
tgcgcgtggg aagtggttcg tgcggaagtg tggcgtgcgc tgagcagcag cgcgaacgtt     480
ctgggccgtc tgcgtgagga aaaagag                                         507
```

<210> SEQ ID NO 135
<211> LENGTH: 167
<212> TYPE: PRT
<213> ORGANISM: Artificial Sequence
<220> FEATURE:
<223> OTHER INFORMATION: synthetic

<400> SEQUENCE: 135

```
Met Ala Cys Asp Leu Pro Gln Thr His Asn Leu Arg Asn Lys Arg Ala
  1               5                  10                  15
Leu Thr Leu Leu Val Gln Met Arg Arg Leu Ser Pro Leu Ser Cys Leu
                 20                  25                  30
Lys Asp Arg Lys Asp Phe Gly Phe Pro Gln Glu Lys Val Asp Ala Gln
             35                  40                  45
Gln Ile Lys Lys Ala Gln Ala Ile Pro Val Leu Ser Glu Leu Thr Gln
         50                  55                  60
Gln Ile Leu Asn Ile Phe Thr Ser Lys Asp Ser Ser Ala Ala Trp Asn
 65                  70                  75                  80
Thr Thr Leu Leu Asp Ser Phe Cys Asn Asp Leu His Gln Gln Leu Asn
                 85                  90                  95
Asp Leu Gln Gly Cys Leu Met Gln Gln Val Gly Val Gln Glu Phe Pro
            100                 105                 110
Leu Thr Gln Glu Asp Ala Leu Leu Ala Val Arg Lys Tyr Phe His Arg
            115                 120                 125
```

```
Ile Thr Val Tyr Leu Arg Glu Lys Lys His Ser Pro Cys Ala Trp Glu
        130                 135                 140

Val Val Arg Ala Glu Val Trp Arg Ala Leu Ser Ser Ser Ala Asn Val
145                 150                 155                 160

Leu Gly Arg Leu Arg Glu Glu
                165

<210> SEQ ID NO 136
<211> LENGTH: 411
<212> TYPE: DNA
<213> ORGANISM: Artificial Sequence
<220> FEATURE:
<223> OTHER INFORMATION: synthetic

<400> SEQUENCE: 136
atggccatcg tgaaagcggg tatcaccatt ccgcgtaacc cgggctgccc gaacagcgaa      60
gataagaact tccgcgtac cgtgatggtt aacctgaaca ttcacaaccg taacaccaac     120
accaacccga aacgtagcag cgactactat aaccgtagca ccagcccgtg gaacctgcac     180
cgtaacgagg atccggaacg ttacccgagc gtgatctggg aggcgaagtg ccgtcacctg     240
ggttgcatta acgcggacgg caacgtggat tatcacatga acagcgttcc gatccagcaa     300
gagattctgg ttctgcgtcg tgaaccgccg cactgcccga acagcttccg tctggaaaaa     360
attctggtta cgttggttg cacctgcgtg accccgattg ttcatcatgt g                411

<210> SEQ ID NO 137
<211> LENGTH: 137
<212> TYPE: PRT
<213> ORGANISM: Artificial Sequence
<220> FEATURE:
<223> OTHER INFORMATION: synthetic

<400> SEQUENCE: 137

Met Ala Ile Val Lys Ala Gly Ile Thr Ile Pro Arg Asn Pro Gly Cys
1               5                   10                  15

Pro Asn Ser Glu Asp Lys Asn Phe Pro Arg Thr Val Met Val Asn Leu
            20                  25                  30

Asn Ile His Asn Arg Asn Thr Asn Thr Asn Pro Lys Arg Ser Ser Asp
        35                  40                  45

Tyr Tyr Asn Arg Ser Thr Ser Pro Trp Asn Leu His Arg Asn Glu Asp
    50                  55                  60

Pro Glu Arg Tyr Pro Ser Val Ile Trp Glu Ala Lys Cys Arg His Leu
65                  70                  75                  80

Gly Cys Ile Asn Ala Asp Gly Asn Val Asp Tyr His Met Asn Ser Val
                85                  90                  95

Pro Ile Gln Gln Glu Ile Leu Val Leu Arg Arg Glu Pro Pro His Cys
            100                 105                 110

Pro Asn Ser Phe Arg Leu Glu Lys Ile Leu Val Ser Val Gly Cys Thr
        115                 120                 125

Cys Val Thr Pro Ile Val His His Val
    130                 135

<210> SEQ ID NO 138
<211> LENGTH: 756
<212> TYPE: DNA
<213> ORGANISM: Artificial Sequence
<220> FEATURE:
<223> OTHER INFORMATION: synthetic

<400> SEQUENCE: 138
```

```
atggcccagg ttcagctgca agagagcggt gggggcctgg tacagccggg cgggagcttg    60
cgcctgtcct gtgcggcatc aggtaatatc ttttcaatta acgcgattgg atggtaccgc   120
caagccccgg ggaaacagcg tgagctggtg gccaccatta ccctctcagg ttccaccaac   180
tacgctgatt ctgtcaaagg cgctttagc atttcacgcg acaatgcaaa aaataccgtg    240
tacctgcaaa tgaattctct taaaccagaa gacactgccg tctattattg caacgcgaac   300
acatattcgg acagtgacgt gtatggttat tggggacagg gtacgcaggt caccgtctcg   360
agcgcacacc atagtgaaga tccctcgtcc aaagccccca agcaccgat ggcaaactgg    420 gtgaacgtta tcagcgacct gaagaaaatc gaggatctga ttcagagcat gcacattgac   480
gcgaccctgt acaccgaaag cgatgtgcac ccgagctgca aggttaccgc gatgaaatgc   540
ttcctgctgg agctgcaagt gatcagcctg gaaagcggtg acgcgagcat tcacgatacc   600
gttgagaacc tgatcattct ggcgaacaac agcctgagca gcaacggtaa cgtgaccgag   660
agcggctgca aggaatgcga ggaactggag gaaaagaaca tcaaagaatt cctgcagagc   720
tttgtgcaca tcgttcaaat gtttattaac accagc                             756

<210> SEQ ID NO 139
<211> LENGTH: 816
<212> TYPE: DNA
<213> ORGANISM: Artificial Sequence
<220> FEATURE:
<223> OTHER INFORMATION: synthetic

<400> SEQUENCE: 139
atggcccagg ttcagctgca agagagcggt gggggcctgg tacagccggg cgggagcttg    60
cgcctgtcct gtgcggcatc aggtaatatc ttttcaatta acgcgattgg atggtaccgc   120
caagccccgg ggaaacagcg tgagctggtg gccaccatta ccctctcagg ttccaccaac   180
tacgctgatt ctgtcaaagg cgctttagc atttcacgcg acaatgcaaa aaataccgtg    240
tacctgcaaa tgaattctct taaaccagaa gacactgccg tctattattg caacgcgaac   300
acatattcgg acagtgacgt gtatggttat tggggacagg gtacgcaggt caccgtctcg   360
agcgcacacc atagtgaaga tccctcgtcc aaagccccca agcaccgat ggcagcgccg    420 accagcagca gcaccaagaa acccagctg caactggaac acctgctgct ggacctgcag   480
atgattctga acggtatcaa caactacaag aacccgaaac tgacccgtat gctgaccttc   540 aagtttata tgccgaagaa agcgaccgag ctgaagcacc tgcagtgcct ggaggaagag    600
ctgaaaccgc tggaagaggt gctgaacctg gcgcaaagca gaacttcca cctgcgtccg    660 cgtgacctga tcagcaacat taacgtgatc gttctggaac tgaaaggcag cgaaaccacc   720
tttatgtgcg aatacgcgga tgaaaccgcg accattgttg aattcctgaa ccgttggatc   780
accttttgcc aaagcatcat tagcaccctg accgag                             816

<210> SEQ ID NO 140
<211> LENGTH: 1491
<212> TYPE: DNA
<213> ORGANISM: Artificial Sequence
<220> FEATURE:
<223> OTHER INFORMATION: synthetic

<400> SEQUENCE: 140
atggaagtgc aactggtgga gagcggcggt ggtctggtgc aaccgggtcg tagcctgaaa    60
ctgagctgcg cggcgagcgg ctttaccttt agcaactacg atatggcgtg ggttcgtcag   120
```

| | |
|---|---|
| gcgccggata ccaagtgcct ggagtgggtt gcgagcatca gcccgagcgg tgatatcacc | 180 |
| tattaccgtg atagcgtgaa aggtcgtttt accgttagcc gtgataacac caaaagcacc | 240 |
| ctgtttctgc agatggatag cctgcgtagc gaagataccg cgacctatta ctgcgcgcgt | 300 |
| cacggcccga ccgaagcgcc ggatattatg gacgcgtggg gtcaaggcgc gagcgttacc | 360 |
| gtgagcagcg gtggtggtgg cagcggtggt ggcggtagcg gtggcggtgg tagcggcccg | 420 |
| cacatcctgg cggtgctgga tttctgggac attgtgatga cccaaagccc gagcagcctg | 480 |
| gcggttagcg cgggcgaaac cgttaccatc aactgcaaaa gcagccagag cctgctgtac | 540 |
| agcggtaacc agaagaacta cctggcgtgg taccagcaaa aaccgggtca gagcccgaag | 600 |
| ctgctgatcc actgggcgag cacccgtcaa agcggcgttc cggaccgttt cattggcagc | 660 |
| ggtagcggca ccgacttcac cctgaccatt agcagcgtgc aagcggagga tctggcgatc | 720 |
| tattactgcc agcaatatta cgacagcccg ctgacctttg gtagcggtac caagctggag | 780 |
| attaagcgtc tggaaggtgg cggcggcagc ggcggcggtg gcagcggtgg cggcggtagc | 840 |
| ccgaaggcgc cgatggcgat cacctgcccg ccgccgatga gcgtggaaca cgcggacatt | 900 |
| tgggtgaaga gctacagcct gtacagccgt gaacgttaca tctgcaacag cggtttcaag | 960 |
| cgtaaagcgg gtaccagcag cctgaccgaa tgcgtgctga caaaagcgac caacgttgcg | 1020 |
| cactggacca ccccgagcct gaaatgcatc cgtgacccgg cgctggttca ccagcgtccg | 1080 |
| gcgccgccga gcgtggtag cggcggcggc ggtagcggcg gtggcagcgg cggtggtggt | 1140 |
| agcctgcaaa actgggttaa cgtgatcagc gatctgaaga aaatcgaaga cctgattcag | 1200 |
| agcatgcaca tcgacgcgac cctgtacacc gaaagcgacg ttcacccgag ctgcaaggtt | 1260 |
| accgcgatga agtgcttcct gctggaactg caagttatca gcctggaaag cggcgacgcg | 1320 |
| agcattcacg acaccgttga gaacctgatc attctggcga caacagcct gagcagcaac | 1380 |
| ggcaacgtta ccgaaagcgg ttgcaaagag tgcgaggaac tggaggaaaa gaatatcaaa | 1440 |
| gagtttctgc aaagcttcgt tcacatcgtt caaatgttca tcaataccag c | 1491 |

```
<210> SEQ ID NO 141
<211> LENGTH: 1056
<212> TYPE: DNA
<213> ORGANISM: Artificial Sequence
<220> FEATURE:
<223> OTHER INFORMATION: synthetic

<400> SEQUENCE: 141
```

| | |
|---|---|
| atggcgcaag ttcaactgca agaaagcggc ggtggtctgg ttcaagcggg cggtagcctg | 60 |
| cgtctgagct gcgcggcgag cggtcgtacc ttcagcaact actatatggg ctggtttcgt | 120 |
| caagcgccgg gcaaggagcg tgaattcgtg gcgaccatca gccagagcgg cagcattacc | 180 |
| tactatgcgg acagcgttaa gggtcgtttt accatcagcc gtgataacgc gaaaaacacc | 240 |
| gtgagcctgc aaatgaacag cctgaagccg gaggacaccg cggtttacta ttgcgcgggc | 300 |
| aacagcttca aagcaacga tcattgggcg agcacctatt ggggccaagg tacccaggtg | 360 |
| accgtttctt ctgcacacca tagtgaagat ccctcgtcca agcccccaa agcaccgatg | 420 |
| gcaatcacat gcccgccgcc gatgtcagtc gaacatgcgg acatttgggt caaaagctac | 480 |
| tccttataca gtcgcgagcg ttatatctgc aactccggct tcaagcgcaa agcgggcacc | 540 |
| agttctctga cggaatgtgt actgaataaa gctacaaatg tggctcactg gacgacccct | 600 |
| agcctgaaat gtattcgcga cccggccctg gtacatcagc gtccggcgcc gccgtcaggg | 660 |
| gggtccggtg gcggaggctc cggggagga tctggcgggg gaggtagctt acaaaaattgg | 720 |

| | |
|---|---|
| gtcaacgtta tcagcgatct gaagaaaatt gaagacttaa ttcagagcat gcacatcgac | 780 |
| gccaccctgt acacggaaag cgatgtgcac ccatcctgta aagtcacagc catgaaatgc | 840 |
| tttctcttgg aacttcaggt aattagcctg gaatccggtg atgcaagcat tcatgatacg | 900 |
| gtcgaaaatt tgattattct tgcgaacaat tctctgtcca gtaatgggaa cgtcacggaa | 960 |
| agcggctgta aggagtgcga agaactggag gagaaaaaca ttaaagaatt tctgcagagc | 1020 |
| ttcgtgcata tcgtgcagat gttcatcaac acatca | 1056 |

<210> SEQ ID NO 142
<211> LENGTH: 825
<212> TYPE: DNA
<213> ORGANISM: Artificial Sequence
<220> FEATURE:
<223> OTHER INFORMATION: synthetic

<400> SEQUENCE: 142

| | |
|---|---|
| atggcgcaag ttcaactgca agaaagcggc ggtggtctgg ttcaagcggg cggtagcctg | 60 |
| cgtctgagct gcgcggcgag cggtcgtacc ttcagcaact actatatggg ctggtttcgt | 120 |
| caagcgccgg gcaaggagcg tgaattcgtg gcgaccatca gccagagcgg cagcattacc | 180 |
| tactatgcgg acagcgttaa gggtcgtttt accatcagcc gtgataacgc gaaaaacacc | 240 |
| gtgagcctgc aaatgaacag cctgaagccg gaggacaccg cggtttacta ttgcgcgggc | 300 |
| aacagcttca aaagcaacga tcattgggcg agcacctatt ggggccaagg tacccaggtg | 360 |
| accgtttctt ctgcacacca tagtgaagat ccctcgtcca aagcccccaa agcaccgatg | 420 |
| gcagcgccga ccagcagcag caccaagaaa acccagctgc aactggaaca cctgctgctg | 480 |
| gacctgcaga tgattctgaa cggtatcaac aactacaaga cccgaaact gacccgtatg | 540 |
| ctgaccttca gttttatat gccgaagaaa gcgaccgagc tgaagcacct gcagtgcctg | 600 |
| gaggaagagc tgaaaccgct ggaagaggtg ctgaacctgg cgcaaagcaa gaacttccac | 660 |
| ctgcgtccgc gtgacctgat cagcaacatt aacgtgatcg ttctggaact gaaaggcagc | 720 |
| gaaaccacct ttatgtgcga atacgcggat gaaaccgcga ccattgttga attcctgaac | 780 |
| cgttggatca cctttttgcca aagcatcatt agcaccctga ccgag | 825 |

<210> SEQ ID NO 143
<211> LENGTH: 1047
<212> TYPE: DNA
<213> ORGANISM: Artificial Sequence
<220> FEATURE:
<223> OTHER INFORMATION: synthetic

<400> SEQUENCE: 143

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccaccccgta tagtgattat tggggtcagg gcaccctggt taccgttagc | 360 |
| agtgcacacc atagtgaaga tccctcgtcc aaagccccca agcaccgat ggcaatcaca | 420 |
| tgcccgccgc cgtgtcagt cgaacatgcg gacatttggg tcaaaagcta ctccttatac | 480 |
| agtcgcgagc gttatatctg caactccggc ttcaagcgca aagcgggcac cagttctctg | 540 |

| | |
|---|---|
| acggaatgtg tactgaataa agctacaaat gtggctcact ggacgacccc tagcctgaaa | 600 |
| tgtattcgcg acccggccct ggtacatcag cgtccggcgc cgccgtcagg ggggtccggt | 660 |
| ggcggaggct ccggggagg atctggcggg ggaggtagct acaaaattg ggtcaacgtt | 720 |
| atcagcgatc tgaagaaaat tgaagactta attcagagca tgcacatcga cgccaccctg | 780 |
| tacacggaaa gcgatgtgca cccatcctgt aaagtcacag ccatgaaatg ctttctcttg | 840 |
| gaacttcagg taattagcct ggaatccggt gatgcaagca ttcatgatac ggtcgaaaat | 900 |
| ttgattattc ttgcgaacaa ttctctgtcc agtaatggga acgtcacgga aagcggctgt | 960 |
| aaggagtgcg aagaactgga ggagaaaaac attaaagaat tctgcagag cttcgtgcat | 1020 |
| atcgtgcaga tgttcatcaa cacatca | 1047 |

```
<210> SEQ ID NO 144
<211> LENGTH: 756
<212> TYPE: DNA
<213> ORGANISM: Artificial Sequence
<220> FEATURE:
<223> OTHER INFORMATION: synthetic

<400> SEQUENCE: 144
```

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccaccccgta tagtgattat tggggtcagg gcaccctggt taccgttagc | 360 |
| agtgcacacc atagtgaaga tccctcgtcc aaagcccca aagcaccgat ggcaaactgg | 420 |
| gtgaacgtta tcagcgacct gaagaaaatc gaggatctga ttcagagcat gcacattgac | 480 |
| gcgaccctgt acaccgaaag cgatgtgcac ccgagctgca aggttaccgc gatgaaatgc | 540 |
| ttcctgctgg agctgcaagt gatcagcctg gaaagcggtg acgcgagcat tcacgatacc | 600 |
| gttgagaacc tgatcattct ggcgaacaac agcctgagca gcaacggtaa cgtgaccgag | 660 |
| agcggctgca aggaatgcga ggaactggag gaaaagaaca tcaaagaatt cctgcagagc | 720 |
| tttgtgcaca tcgttcaaat gtttattaac accagc | 756 |

```
<210> SEQ ID NO 145
<211> LENGTH: 816
<212> TYPE: DNA
<213> ORGANISM: Artificial Sequence
<220> FEATURE:
<223> OTHER INFORMATION: synthetic

<400> SEQUENCE: 145
```

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccaccccgta tagtgattat tggggtcagg gcaccctggt taccgttagc | 360 |
| agtgcacacc atagtgaaga tccctcgtcc aaagcccca aagcaccgat ggcagcgccg | 420 |
| accagcagca gcaccaagaa aacccagctg caactggaac acctgctgct ggacctgcag | 480 |

```
atgattctga acggtatcaa caactacaag aacccgaaac tgacccgtat gctgaccttc    540 aagtttata tgccgaagaa agcgaccgag ctgaagcacc tgcagtgcct ggaggaagag     600
ctgaaaccgc tggaagaggt gctgaacctg gcgcaaagca agaacttcca cctgcgtccg    660
cgtgacctga tcagcaacat taacgtgatc gttctgaac tgaaaggcag cgaaaccacc    720
tttatgtgcg aatacgcgga tgaaaccgcg accattgttg aattcctgaa ccgttggatc    780
accttttgcc aaagcatcat tagcaccctg accgag                              816
```

<210> SEQ ID NO 146
<211> LENGTH: 16
<212> TYPE: PRT
<213> ORGANISM: Homo sapiens

<400> SEQUENCE: 146

Ser Pro Ser Thr Pro Pro Thr Pro Ser Pro Ser Thr Pro Pro Ala Ser
1               5                   10                  15

<210> SEQ ID NO 147
<211> LENGTH: 23
<212> TYPE: DNA
<213> ORGANISM: Artificial Sequence
<220> FEATURE:
<223> OTHER INFORMATION: synthetic

<400> SEQUENCE: 147
gtcctggctg ctcttctaca agg                                            23

<210> SEQ ID NO 148
<211> LENGTH: 23
<212> TYPE: DNA
<213> ORGANISM: Artificial Sequence
<220> FEATURE:
<223> OTHER INFORMATION: synthetic

<400> SEQUENCE: 148
ggtacgtgct gttgaactgt tcc                                            23

<210> SEQ ID NO 149
<211> LENGTH: 29
<212> TYPE: DNA
<213> ORGANISM: Artificial Sequence
<220> FEATURE:
<223> OTHER INFORMATION: synthetic

<400> SEQUENCE: 149
gatgtgcagc tgcaggagtc tggrggagg                                      29

<210> SEQ ID NO 150
<211> LENGTH: 32
<212> TYPE: DNA
<213> ORGANISM: Artificial Sequence
<220> FEATURE:
<223> OTHER INFORMATION: synthetic

<400> SEQUENCE: 150
ctagtgcggc cgctggagac ggtgacctgg gt                                  32

<210> SEQ ID NO 151
<211> LENGTH: 20
<212> TYPE: PRT
<213> ORGANISM: Artificial Sequence
<220> FEATURE:
<223> OTHER INFORMATION: synthetic

<400> SEQUENCE: 151

Met Lys Ser Leu Leu Pro Thr Ala Ala Ala Gly Leu Leu Leu Leu Ala
1               5                   10                  15

Ala Gln Pro Ala
            20

<210> SEQ ID NO 152
<211> LENGTH: 879
<212> TYPE: DNA
<213> ORGANISM: Artificial Sequence
<220> FEATURE:
<223> OTHER INFORMATION: synthetic

<400> SEQUENCE: 152

| | | | | | |
|---|---|---|---|---|---|
| atggccgatg | ttcagctggt | tgaaagcggc | ggcggtctgg | tgcagccggg | tggtagctta | 60 |
| cgtctgagct | gcgcagccag | tggtagtatt | tttacaatta | atgctatggg | ttggtaccgt | 120 |
| caggcaccgg | gcaaacagcg | cgaagaagtt | gcagcaatta | ccagcggtgg | tagtaccaat | 180 |
| tatgccgata | gcgtgaaagg | tcgttttacc | attagtcgcg | ataatgcaaa | aaataccgtt | 240 |
| tatctgcaga | tgaatagcct | gaaaccggaa | gataccgcag | tttattattg | caaagccgtt | 300 |
| gtggtgacca | ccaccccgta | tagtgattat | tggggtcagg | gcaccctggt | taccgttagc | 360 |
| agtgcacacc | atagtgaaga | tccctcgtcc | aaagccccca | agcaccgta | cttcggaaag | 420 |
| ctggagtcaa | aacttagcgt | catccgcaac | ctgaatgacc | aagttttatt | cattgatcaa | 480 |
| ggaaatcgcc | ctctgtttga | agacatgacc | gatagtgact | gtcgcgataa | cgcgcctcgt | 540 |
| acaatcttta | tcatcagcat | gtataaagat | tcgcaacctc | gtggcatggc | cgtgaccatc | 600 |
| tctgtaaaat | gcgagaaaat | ctcgacactt | agctgtgaga | ataagatcat | ctcattcaaa | 660 |
| gaaatgaatc | cgcccgacaa | cattaaggac | accaaaagcg | acattatttt | cttccaacgc | 720 |
| tcagtaccgg | gccatgataa | taagatgcag | ttcgagagta | gctcatacga | agggtatttt | 780 |
| ctggcatgtg | aaaaggaacg | tgatttattc | aagttgattc | tgaagaaaga | ggatgaatta | 840 |
| ggagaccgca | gcattatgtt | cacagtccag | aatgaggac | | | 879 |

<210> SEQ ID NO 153
<211> LENGTH: 873
<212> TYPE: DNA
<213> ORGANISM: Artificial Sequence
<220> FEATURE:
<223> OTHER INFORMATION: synthetic

<400> SEQUENCE: 153

| | | | | | |
|---|---|---|---|---|---|
| atggccgatg | ttcagctggt | tgaaagcggc | ggcggtctgg | tgcagccggg | tggtagctta | 60 |
| cgtctgagct | gcgcagccag | tggtagtatt | tttacaatta | atgctatggg | ttggtaccgt | 120 |
| caggcaccgg | gcaaacagcg | cgaagaagtt | gcagcaatta | ccagcggtgg | tagtaccaat | 180 |
| tatgccgata | gcgtgaaagg | tcgttttacc | attagtcgcg | ataatgcaaa | aaataccgtt | 240 |
| tatctgcaga | tgaatagcct | gaaaccggaa | gataccgcag | tttattattg | caaagccgtt | 300 |
| gtggtgacca | ccaccccgta | tagtgattat | tggggtcagg | gcaccctggt | taccgttagc | 360 |
| agtgcacacc | atagtgaaga | tccctcgtcc | aaagccccca | agcaccgat | ggcagactgc | 420 |
| gatatcgagg | gcaaggacgg | caaacagtac | gaaagcgtgc | tgatggttag | catcgaccaa | 480 |
| ctgctggata | gcatgaagga | gattggtagc | aactgcctga | caacgaatt | caacttcttt | 540 |
| aagcgtcaca | tttgcgatgc | gaacaaagag | ggcatgttcc | tgtttcgtgc | ggcgcgtaag | 600 |

```
ctgcgtcagt tcctgaaaat gaacagcacc ggtgactttg atctgcacct gctgaaggtg    660
agcgaaggca ccaccatcct gctgaactgc accggtcagg ttaaaggtcg taaaccggcg    720
gcgctgggcg aggcgcaacc gaccaaaagc ctggaggaaa acaagagcct gaaagaacag    780
aagaaactga cgacctgtgt ctttctgaag cgtctgctgc aagagatcaa gacctgctgg    840
aacaaaattc tgatgggcac caaagaacac gag                                 873
```

<210> SEQ ID NO 154
<211> LENGTH: 888
<212> TYPE: DNA
<213> ORGANISM: Artificial Sequence
<220> FEATURE:
<223> OTHER INFORMATION: synthetic

<400> SEQUENCE: 154

```
atggccgatg ttcagctggt tgaaagcggc ggcggtctgg tgcagccggg tggtagctta     60
cgtctgagct gcgcagccag tggtagtatt tttacaatta atgctatggg ttggtaccgt    120
caggcaccgg gcaaacagcg cgaagaagtt gcagcaatta ccagcggtgg tagtaccaat    180
tatgccgata gcgtgaaagg tcgttttacc attagtcgcg ataatgcaaa aaataccgtt    240
tatctgcaga tgaatagcct gaaaccggaa gataccgcag tttattattg caaagccgtt    300
gtggtgacca ccaccccgta tagtgattat tggggtcagg gcaccctggt taccgttagc    360
agtgcacacc atagtgaaga tcccctcgtcc aaagccccca agcaccgat ggcagtgcgt    420 agcagcagcc gtaccccgag cgacaagccg gttgcgcatg tggttgcgaa cccgcaggcg    480
gagggtcagc tgcaatggct gaaccgtcgt gcgaacgcgc tgctggcgaa cggtgtggaa    540
ctgcgtgata accaactggt ggttccgagc gagggcctgt acctgatcta tagccaggtg    600
ctgttcaaag gtcaaggctg cccgagcacc cacgttctgc tgacccacac catcagccgt    660
attgcggtga gctaccagac caaggttaac ctgctgagcg cgattaaaag cccgtgccaa    720
cgtgaaaccc cggagggtgc ggaggcgaag ccgtggtacg aaccgatcta tctgggtggc    780
gtgtttcagc tggaaaaagg cgaccgtctg agcgcggaga ttaaccgtcc ggactacctg    840
gatttcgcgg agagcggtca gtttatttt ggcatcattg cgctggag                  888
```

<210> SEQ ID NO 155
<211> LENGTH: 903
<212> TYPE: DNA
<213> ORGANISM: Artificial Sequence
<220> FEATURE:
<223> OTHER INFORMATION: synthetic

<400> SEQUENCE: 155

```
atggccgatg ttcagctggt tgaaagcggc ggcggtctgg tgcagccggg tggtagctta     60
cgtctgagct gcgcagccag tggtagtatt tttacaatta atgctatggg ttggtaccgt    120
caggcaccgg gcaaacagcg cgaagaagtt gcagcaatta ccagcggtgg tagtaccaat    180
tatgccgata gcgtgaaagg tcgttttacc attagtcgcg ataatgcaaa aaataccgtt    240
tatctgcaga tgaatagcct gaaaccggaa gataccgcag tttattattg caaagccgtt    300
gtggtgacca ccaccccgta tagtgattat tggggtcagg gcaccctggt taccgttagc    360
agtgcacacc atagtgaaga tcccctcgtcc aaagccccca agcaccgtg cgaccttccg    420 caaacccatt cgttagggtc ccgccgtact cttatgctgc ttgctcagat gcgtaagatt    480
tccctgttca gttgccttaa ggaccgtcac gattttggtt ttcctcagga ggagtttgga    540
aaccagtttc agaaagcaga aacgattcca gtcctgcatg agatgatcca gcaaatttc    600
```

```
aacctgtttt cgactaagga ctccagtgca gcatgggacg agactttgtt ggacaaattt      660
tatacggagc tgtatcaaca attgaatgat ctggaggctt gcgttattca aggcgtcgga      720
gtgacggaga ctccgctgat gaaagaggac tcaattttag cagtgcgtaa atattttcaa      780
cgtattacac tgtatttgaa ggaaaagaaa tactcaccgt gtgcctggga ggtggtacgt      840
gccgagatca tgcgttcttt ctcgctgtct accaaccttc aggaaagctt gcgtagcaag      900
gag                                                                   903

<210> SEQ ID NO 156
<211> LENGTH: 804
<212> TYPE: DNA
<213> ORGANISM: Artificial Sequence
<220> FEATURE:
<223> OTHER INFORMATION: synthetic

<400> SEQUENCE: 156
atggccgatg ttcagctggt tgaaagcggc ggcggtctgg tgcagccggg tggtagctta       60
cgtctgagct gcgcagccag tggtagtatt tttacaatta atgctatggg ttggtaccgt      120
caggcaccgg gcaaacagcg cgaagaagtt gcagcaatta ccagcggtgg tagtaccaat      180
tatgccgata gcgtgaaagg tcgttttacc attagtcgcg ataatgcaaa aaataccgtt      240
tatctgcaga tgaatagcct gaaaccggaa gataccgcag tttattattg caaagccgtt      300
gtggtgacca ccaccccgta tagtgattat tggggtcagg gcaccctggt taccgttagc      360
agtgcacacc atagtgaaga tccctcgtcc aaagccccca agcaccgat gcaagaccgc      420 cacatgatcc gcatgcgcca attgattgac attgtagatc agttgaagaa ttacgtgaac      480
gatcttgtgc ctgagttcct gccggctccg gaggatgtag aaaccaattg cgaatggtct      540
gctttctcgt gcttccagaa agctcaattg aagagtgcta cactggaaa taacgaacgc      600 atcatcaatg tgagcattaa aaagctgaag cgtaaacctc cttcaactaa tgctggacgc      660
cgtcagaaac atcgcttaac ctgcccatcg tgtgactctt atgagaaaaa accgccgaag      720
gaattttggg agcgtttcaa atcacttctg cagaagatga ttcatcaaca tttatcctcc      780
cgtactcatg ggtccgaaga cagc                                            804

<210> SEQ ID NO 157
<211> LENGTH: 888
<212> TYPE: DNA
<213> ORGANISM: Artificial Sequence
<220> FEATURE:
<223> OTHER INFORMATION: synthetic

<400> SEQUENCE: 157
atggcgcaag ttcaactgca agaaagcggc ggtggtctgg ttcaagcggg cggtagcctg       60
cgtctgagct gcgcggcgag cggtcgtacc ttcagcaact actatatggg ctggtttcgt      120
caagcgccgg gcaaggagcg tgaattcgtg gcgaccatca gccagagcgg cagcattacc      180
tactatgcgg acagcgttaa gggtcgtttt accatcagcc gtgataacgc gaaaaacacc      240
gtgagcctgc aaatgaacag cctgaagccg gaggacaccg cggtttacta ttgcgcgggc      300
aacagcttca aaagcaacga tcattgggcg agcacctatt ggggccaagg tacccaggtg      360
accgtttctt ctgcacacca tagtgaagat ccctcgtcca aagcccccaa agcaccgtac      420
ttcggaaagc tggagtcaaa acttagcgtc atccgcaacc tgaatgacca gttttattc      480 attgatcaag gaaatcgccc tctgtttgaa gacatgaccg atagtgactg tcgcgataac      540
```

```
gcgcctcgta caatctttat catcagcatg tataaagatt cgcaacctcg tggcatggcc    600
gtgaccatct ctgtaaaatg cgagaaaatc tcgacactta gctgtgagaa taagatcatc    660
tcattcaaag aaatgaatcc gcccgacaac attaaggaca ccaaaagcga cattattttc    720
ttccaacgct cagtaccggg ccatgataat aagatgcagt tcgagagtag ctcatacgaa    780
gggtattttc tggcatgtga aaaggaacgt gatttattca agttgattct gaagaaagag    840
gatgaattag agaccgcag cattatgttc acagtccaga atgaggac                  888
```

<210> SEQ ID NO 158
<211> LENGTH: 882
<212> TYPE: DNA
<213> ORGANISM: Artificial Sequence
<220> FEATURE:
<223> OTHER INFORMATION: synthetic

<400> SEQUENCE: 158

```
atggcgcaag ttcaactgca agaaagcggc ggtggtctgg ttcaagcggg cggtagcctg     60
cgtctgagct gcgcggcgag cggtcgtacc ttcagcaact actatatggg ctggtttcgt    120
caagcgccgg gcaaggagcg tgaattcgtg gcgaccatca gccagagcgg cagcattacc    180
tactatgcga cagcgttaa gggtcgtttt accatcagcc gtgataacgc gaaaaacacc    240
gtgagcctgc aaatgaacag cctgaagccg gaggacaccg cggtttacta ttgcgcgggc    300
aacagcttca aaagcaacga tcattgggcg agcacctatt ggggccaagg tacccaggtg    360
accgtttctt ctgcacacca tagtgaagat ccctcgtcca agcccccaa agcaccgatg    420 gcagactgcg atatcgaggg caaggacggc aaacagtacg aaagcgtgct gatggttagc    480
atcgaccaac tgctggatag catgaaggag attggtagca actgcctgaa caacgaattc    540
aacttcttta gcgtcacat ttgcgatgcg aacaaagagg gcatgttcct gtttcgtgcg    600
gcgcgtaagc tgcgtcagtt cctgaaaatg aacagcaccg gtgactttga tctgcacctg    660
ctgaaggtga gcaaggcac caccatcctg ctgaactgca ccggtcaggt taaaggtcgt    720
aaaccggcgg cgctgggcga ggcgcaaccg accaaaagcc tggaggaaaa caagagcctg    780
aaagaacaga gaaactgaa cgacctgtgc tttctgaagc gtctgctgca agagatcaag    840
acctgctgga acaaaattct gatgggcacc aaagaacacg ag                       882
```

<210> SEQ ID NO 159
<211> LENGTH: 897
<212> TYPE: DNA
<213> ORGANISM: Artificial Sequence
<220> FEATURE:
<223> OTHER INFORMATION: synthetic

<400> SEQUENCE: 159

```
atggcgcaag ttcaactgca agaaagcggc ggtggtctgg ttcaagcggg cggtagcctg     60
cgtctgagct gcgcggcgag cggtcgtacc ttcagcaact actatatggg ctggtttcgt    120
caagcgccgg gcaaggagcg tgaattcgtg gcgaccatca gccagagcgg cagcattacc    180
tactatgcgg acagcgttaa gggtcgtttt accatcagcc gtgataacgc gaaaaacacc    240
gtgagcctgc aaatgaacag cctgaagccg gaggacaccg cggtttacta ttgcgcgggc    300
aacagcttca aaagcaacga tcattgggcg agcacctatt ggggccaagg tacccaggtg    360
accgtttctt ctgcacacca tagtgaagat ccctcgtcca agcccccaa agcaccgatg    420 gcagtgcgta gcagcagccg taccccgagc gacaagccgg ttgcgcatgt ggttgcgaac    480
ccgcaggcgg agggtcagct gcaatggctg aaccgtcgtg cgaacgcgct gctggcgaac    540
```

```
ggtgtggaac tgcgtgataa ccaactggtg gttccgagcg agggcctgta cctgatctat      600
agccaggtgc tgttcaaagg tcaaggctgc ccgagcaccc acgttctgct gacccacacc      660
atcagccgta ttgcggtgag ctaccagacc aaggttaacc tgctgagcgc gattaaaagc      720
ccgtgccaac gtgaaacccc ggagggtgcg gaggcgaagc cgtggtacga accgatctat      780
ctgggtggcg tgtttcagct ggaaaaaggc gaccgtctga gcgcggagat taaccgtccg      840
gactacctgg atttcgcgga gagcggtcaa gtttattttg gcatcattgc gctggag        897

<210> SEQ ID NO 160
<211> LENGTH: 912
<212> TYPE: DNA
<213> ORGANISM: Artificial Sequence
<220> FEATURE:
<223> OTHER INFORMATION: synthetic

<400> SEQUENCE: 160
atggcgcaag ttcaactgca agaaagcggc ggtggtctgg ttcaagcggg cggtagcctg       60
cgtctgagct gcgcggcgag cggtcgtacc ttcagcaact actatatggg ctggtttcgt      120
caagcgccgg gcaaggagcg tgaattcgtg gcgaccatca gccagagcgg cagcattacc      180
tactatgcgg acagcgttaa gggtcgtttt accatcagcc gtgataacgc gaaaaacacc      240
gtgagcctgc aaatgaacag cctgaagccg gaggacaccg cggtttacta ttgcgcgggc      300
aacagcttca aaagcaacga tcattgggcg agcacctatt ggggccaagg tacccaggtg      360
accgtttctt ctgcacacca tagtgaagat ccctcgtcca aagcccccaa agcaccgtgc      420
gaccttccgc aaacccattc gttagggtcc cgccgtactc ttatgctgct tgctcagatg      480
cgtaagattt ccctgttcag ttgccttaag gaccgtcacg attttggttt tcctcaggag      540
gagtttggaa accagtttca gaaagcagaa acgattccag tcctgcatga gatgatccag      600
caaattttca acctgttttc gactaaggac tccagtgcag catgggacga gactttgttg      660
gacaaatttt atacggagct gtatcaacaa ttgaatgatc tggaggcttg cgttattcaa      720
ggcgtcggag tgacggagac tccgctgatg aaagaggact caattttagc agtgcgtaaa      780
tattttcaac gtattacact gtatttgaag gaaaagaaat actcaccgtg tgcctgggag      840
gtggtacgtg ccgagatcat gcgttctttc tcgctgtcta ccaaccttca ggaaagcttg      900
cgtagcaagg ag                                                         912

<210> SEQ ID NO 161
<211> LENGTH: 813
<212> TYPE: DNA
<213> ORGANISM: Artificial Sequence
<220> FEATURE:
<223> OTHER INFORMATION: synthetic

<400> SEQUENCE: 161
atggcgcaag ttcaactgca agaaagcggc ggtggtctgg ttcaagcggg cggtagcctg       60
cgtctgagct gcgcggcgag cggtcgtacc ttcagcaact actatatggg ctggtttcgt      120
caagcgccgg gcaaggagcg tgaattcgtg gcgaccatca gccagagcgg cagcattacc      180
tactatgcgg acagcgttaa gggtcgtttt accatcagcc gtgataacgc gaaaaacacc      240
gtgagcctgc aaatgaacag cctgaagccg gaggacaccg cggtttacta ttgcgcgggc      300
aacagcttca aaagcaacga tcattgggcg agcacctatt ggggccaagg tacccaggtg      360
accgtttctt ctgcacacca tagtgaagat ccctcgtcca aagcccccaa agcaccgatg      420
```

| | |
|---|---|
| caagaccgcc acatgatccg catgcgccaa ttgattgaca ttgtagatca gttgaagaat | 480 |
| tacgtgaacg atcttgtgcc tgagttcctg ccggctccgg aggatgtaga aaccaattgc | 540 |
| gaatggtctg ctttctcgtg cttccagaaa gctcaattga agagtgctaa cactggaaat | 600 |
| aacgaacgca tcatcaatgt gagcattaaa aagctgaagc gtaaacctcc ttcaactaat | 660 |
| gctggacgcc gtcagaaaca tcgcttaacc tgcccatcgt gtgactctta tgagaaaaaa | 720 |
| ccgccgaagg aattttttgga gcgtttcaaa tcacttctgc agaagatgat tcatcaacat | 780 |
| ttatcctccc gtactcatgg gtccgaagac agc | 813 |

<210> SEQ ID NO 162
<211> LENGTH: 960
<212> TYPE: DNA
<213> ORGANISM: Artificial Sequence
<220> FEATURE:
<223> OTHER INFORMATION: synthetic

<400> SEQUENCE: 162

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccaccccgta tagtgattat tggggtcagg gcaccctggt taccgttagc | 360 |
| agtgcacacc atagtgaaga tccctcgtcc aaagccccca agcaccgat gcgcgaaggg | 420 |
| ccggagttat caccgacga ccccgctgga cttctggacc ttcgccaagg tatgtttgct | 480 |
| caattagtcg ctcagaacgt cttgctgatt gatggcccac tgtcttggta ctctgatcca | 540 |
| ggattagccg gggtttcgtt aacgggggga ctgtcttata aggaagacac caaagaattg | 600 |
| gtggtagcaa aggccgggt ttactatgtt tttttccagt tagaattacg tcgtgttgta | 660 |
| gctggcgagg gtagcggttc cgtgagcctg ctctgcatt tgcaaccatt gcgtagtgca | 720 |
| gctggggccg ccgccttagc ccttacggta gacttaccgc tgcatctag cgaagcccgt | 780 |
| aattcagcat ttggttttca ggggcgtttg ttgcatttaa gtgcgggcca acgcctggga | 840 |
| gtgcatttgc atacggaggc tcgtgctcgt cacgcctggc aacttacgca gggtgcgacc | 900 |
| gtattgggct tgtttcgtgt gactcctgag atcccagcgg gacttccctc tcctcgtagc | 960 |

<210> SEQ ID NO 163
<211> LENGTH: 969
<212> TYPE: DNA
<213> ORGANISM: Artificial Sequence
<220> FEATURE:
<223> OTHER INFORMATION: synthetic

<400> SEQUENCE: 163

| | |
|---|---|
| atggcgcaag ttcaactgca agaaagcggc ggtggtctgg ttcaagcggg cggtagcctg | 60 |
| cgtctgagct gcgcggcgag cggtcgtacc ttcagcaact actatatggg ctggttccgt | 120 |
| caagcgccgg gcaaggagcg tgaattcgtg gcgaccatca gccagagcgg cagcattacc | 180 |
| tactatgcgg acagcgttaa gggtcgtttt accatcagcc gtgataacgc gaaaaacacc | 240 |
| gtgagcctgc aaatgaacag cctgaagccg gaggacaccg cggtttacta ttgcgcgggc | 300 |
| aacagcttca aaagcaacga tcattgggcg agcacctatt ggggccaagg tacccaggtg | 360 |
| accgtttctt ctgcacacca tagtgaagat ccctcgtcca aagcccccaa agcaccgatg | 420 |

| | |
|---|---|
| cgcgaagggc cggagttatc acccgacgac cccgctggac ttctggacct tcgccaaggt | 480 |
| atgtttgctc aattagtcgc tcagaacgtc ttgctgattg atggcccact gtcttggtac | 540 |
| tctgatccag gattagccgg ggtttcgtta acgggggac tgtcttataa ggaagacacc | 600 |
| aaagaattgg tggtagcaaa ggccgggtt tactatgttt ttttccagtt agaattacgt | 660 |
| cgtgttgtag ctggcgaggg tagcggttcc gtgagcctgg ctctgcattt gcaaccattg | 720 |
| cgtagtgcac tggggccgc cgccttagcc cttacggtag acttaccgcc tgcatctagc | 780 |
| gaagcccgta attcagcatt tggttttcag gggcgtttgt tgcatttaag tgcgggccaa | 840 |
| cgcctgggag tgcatttgca tacgaggct cgtgctcgtc acgcctggca acttacgcag | 900 |
| ggtgcgaccg tattgggctt gtttcgtgtg actcctgaga tcccagcggg acttccctct | 960 |
| cctcgtagc | 969 |

<210> SEQ ID NO 164
<211> LENGTH: 807
<212> TYPE: DNA
<213> ORGANISM: Artificial Sequence
<220> FEATURE:
<223> OTHER INFORMATION: synthetic

<400> SEQUENCE: 164

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccacccccgta tagtgattat tggggtcagg gcaccctggt taccgttagc | 360 |
| agtgcacacc atagtgaaga tccctcgtcc aaagccccca aagcaccgca ggtgagccat | 420 |
| cgctatcccc gtattcaaag tatcaaggta caattcacag agtataagaa agaaaagggc | 480 |
| tttatcttga cctcacaaaa agaggacgaa attatgaagg tgcagaataa ctcagtaatt | 540 |
| atcaactgtg atgggttcta cttaattagt ttgaaaggtt acttctcaca ggaggttaat | 600 |
| atctctctgc attaccaaaa agacgaggag ccgcttttc aattaaaaaa ggttcgcagt | 660 |
| gtaaattcac tgatggtcgc gtctttaact tataaggaca aagtttacct taatgtcacg | 720 |
| acagacaata catcacttga tgactttcac gtcaacggag gggagctgat tctgattcac | 780 |
| cagaaccctg gcgaattctg tgtactg | 807 |

<210> SEQ ID NO 165
<211> LENGTH: 816
<212> TYPE: DNA
<213> ORGANISM: Artificial Sequence
<220> FEATURE:
<223> OTHER INFORMATION: synthetic

<400> SEQUENCE: 165

| | |
|---|---|
| atggcgcaag ttcaactgca agaaagcggc ggtggtctgg ttcaagcggg cggtagcctg | 60 |
| cgtctgagct gcgcggcgag cggtcgtacc ttcagcaact actatatggg ctggtttcgt | 120 |
| caagcgccgg gcaaggagcg tgaattcgtg gcgaccatca gccagagcgg cagcattacc | 180 |
| tactatgcgg acagcgttaa gggtcgtttt accatcagcc gtgataacgc gaaaaacacc | 240 |
| gtgagcctgc aaatgaacag cctgaagccg gaggacaccg cggtttacta ttgcgcgggc | 300 |

| | |
|---|---|
| aacagcttca aaagcaacga tcattgggcg agcacctatt ggggccaagg tacccaggtg | 360 |
| accgtttctt ctgcacacca tagtgaagat ccctcgtcca aagcccccaa agcaccgcag | 420 |
| gtgagccatc gctatccccg tattcaaagt atcaaggtac aattcacaga gtataagaaa | 480 |
| gaaaagggct ttatcttgac ctcacaaaaa gaggacgaaa ttatgaaggt gcagaataac | 540 |
| tcagtaatta tcaactgtga tgggttctac ttaattagtt tgaaaggtta cttctcacag | 600 |
| gaggttaata tctctctgca ttaccaaaaa gacgaggagc cgcttttcca attaaaaaag | 660 |
| gttcgcagtg taaattcact gatggtcgcg tctttaactt ataaggacaa agtttacctt | 720 |
| aatgtcacga cagacaatac atcacttgat gactttcacg tcaacggagg ggagctgatt | 780 |
| ctgattcacc agaaccctgg cgaattctgt gtactg | 816 |

<210> SEQ ID NO 166
<211> LENGTH: 855
<212> TYPE: DNA
<213> ORGANISM: Artificial Sequence
<220> FEATURE:
<223> OTHER INFORMATION: synthetic

<400> SEQUENCE: 166

| | |
|---|---|
| atggccgatg ttcagctggt tgaaagcggc ggcggtctgg tgcagccggg tggtagctta | 60 |
| cgtctgagct gcgcagccag tggtagtatt tttacaatta atgctatggg ttggtaccgt | 120 |
| caggcaccgg gcaaacagcg cgaagaagtt gcagcaatta ccagcggtgg tagtaccaat | 180 |
| tatgccgata gcgtgaaagg tcgttttacc attagtcgcg ataatgcaaa aaataccgtt | 240 |
| tatctgcaga tgaatagcct gaaaccggaa gataccgcag tttattattg caaagccgtt | 300 |
| gtggtgacca ccaccccgta tagtgattat tggggtcagg gcaccctggt taccgttagc | 360 |
| agtgcacacc atagtgaaga tccctcgtcc aaagccccca agcaccgat gcaaaagggg | 420 |
| gaccaaaatc ctcaaattgc cgcccacgtc atttccgagg caagttcaaa gactacgtcg | 480 |
| gtacttcagt gggcggagaa aggatactac accatgtcaa caaccttgt gacgttggag | 540 |
| aatggcaaac aactgactgt caaacgccaa ggtttatatt atatttacgc gcaggtgaca | 600 |
| ttctgtagta atcgtgaagc ctctagtcaa gcgccttttca tcgcttcttt atggttgaag | 660 |
| tcgcctggtc gttttgagcg tattcttta cgtgcggcca atacacacag tagtgccaag | 720 |
| ccgtgtggtc agcaaagcat tcacttaggt ggcgtatttg agttacaacc tggagcaagc | 780 |
| gtctttgtaa acgtgacaga tccctctcag gtgtcccatg ggacgggttt caccagcttt | 840 |
| ggcctgctga agctg | 855 |

<210> SEQ ID NO 167
<211> LENGTH: 864
<212> TYPE: DNA
<213> ORGANISM: Artificial Sequence
<220> FEATURE:
<223> OTHER INFORMATION: synthetic

<400> SEQUENCE: 167

| | |
|---|---|
| atggcgcaag ttcaactgca agaaagcggc ggtggtctgg ttcaagcggg cggtagcctg | 60 |
| cgtctgagct gcgcggcgag cggtcgtacc ttcagcaact actatatggg ctggtttcgt | 120 |
| caagcgccgg gcaaggagcg tgaattcgtg gcgaccatca gccagagcgg cagcattacc | 180 |
| tactatgcgg acagcgttaa gggtcgtttt accatcagcc gtgataacgc gaaaaacacc | 240 |
| gtgagcctgc aaatgaacag cctgaagccg gaggacaccg cggtttacta ttgcgcgggc | 300 |
| aacagcttca aaagcaacga tcattgggcg agcacctatt ggggccaagg tacccaggtg | 360 |

```
accgtttctt ctgcacacca tagtgaagat ccctcgtcca aagcccccaa agcaccgatg    420
caaaaagggg accaaaatcc tcaaattgcc gcccacgtca tttccgaggc aagttcaaag    480
actacgtcgg tacttcagtg ggcggagaaa ggatactaca ccatgtcaaa caaccttgtg    540
acgttggaga atggcaaaca actgactgtc aaacgccaag gtttatatta tatttacgcg    600
caggtgacat tctgtagtaa tcgtgaagcc tctagtcaag cgcctttcat cgcttcttta    660
tggttgaagt cgcctggtcg ttttgagcgt attcttttac gtgcggccaa tacacacagt    720
agtgccaagc cgtgtggtca gcaaagcatt cacttaggtg gcgtatttga gttacaacct    780
ggagcaagcg tctttgtaaa cgtgacagat ccctctcagg tgtcccatgg gacgggtttc    840
accagctttg gcctgctgaa gctg                                           864
```

```
<210> SEQ ID NO 168
<211> LENGTH: 870
<212> TYPE: DNA
<213> ORGANISM: Artificial Sequence
<220> FEATURE:
<223> OTHER INFORMATION: synthetic

<400> SEQUENCE: 168
atggccgatg ttcagctggt tgaaagcggc ggcggtctgg tgcagccggg tggtagctta     60
cgtctgagct gcgcagccag tggtagtatt tttacaatta atgctatggg ttggtaccgt    120
caggcaccgg gcaaacagcg cgaagaagtt gcagcaatta ccagcggtgg tagtaccaat    180
tatgccgata gcgtgaaagg tcgttttacc attagtcgcg ataatgcaaa aaataccgtt    240
tatctgcaga tgaatagcct gaaaccggaa gataccgcag tttattattg caaagccgtt    300
gtggtgacca ccaccccgta tagtgattat tggggtcagg gcaccctggt taccgttagc    360
agtgcacacc atagtgaaga tccctcgtcc aaagccccca agcaatggc agactgcgat    420 atcgagggca aggacggcaa acagtacgaa agcgtgctga tggttagcat cgaccaactg    480
ctggatagca tgaaggagat tggtagcaac tgcctgaaca acgaattcaa cttctttaag    540
cgtcacattt gcgatgcgaa caaagagggc atgttcctgt tcgtgcggc gcgtaagctg    600 cgtcagttcc tgaaaatgaa cagcaccggt gactttgatc tgcacctgct gaaggtgagc    660
gaaggcacca ccatcctgct gaactgcacc ggtcaggtta aggtcgtaa accggcggcg    720 ctgggcgagg cgcaaccgac caaaagcctg gaggaaaaca gagcctgaa agaacagaag    780 aaactgaacg acctgtgctt tctgaagcgt ctgctgcaag agatcaagac ctgctggaac    840
aaaattctga tgggcaccaa agaacacgag                                     870
```

```
<210> SEQ ID NO 169
<211> LENGTH: 879
<212> TYPE: DNA
<213> ORGANISM: Artificial Sequence
<220> FEATURE:
<223> OTHER INFORMATION: synthetic

<400> SEQUENCE: 169
atggcgcaag ttcaactgca agaaagcggc ggtggtctgg ttcaagcggg cggtagcctg     60
cgtctgagct gcgcggcgag cggtcgtacc ttcagcaact actatatggg ctggtttcgt    120
caagcgccgg gcaaggagcg tgaattcgtg gcgaccatca gccagagcgg cagcattacc    180
tactatgcgg acagcgttaa gggtcgtttt accatcagcc gtgataacgc gaaaaacacc    240
gtgagcctgc aaatgaacag cctgaagccg gaggacaccg cggtttacta ttgcgcgggc    300
```

```
aacagcttca aaagcaacga tcattgggcg agcacctatt ggggccaagg tacccaggtg    360
accgtttctt ctgcacacca tagtgaagat ccctcgtcca aagcccccaa agcaatggca    420
gactgcgata tcgagggcaa ggacggcaaa cagtacgaaa gcgtgctgat ggttagcatc    480
gaccaactgc tggatagcat gaaggagatt ggtagcaact gcctgaacaa cgaattcaac    540
ttctttaagc gtcacatttg cgatgcgaac aaagagggca tgttcctgtt tcgtgcggcg    600
cgtaagctgc gtcagttcct gaaaatgaac agcaccggtg actttgatct gcacctgctg    660
aaggtgagcg aaggcaccac catcctgctg aactgcaccg gtcaggttaa aggtcgtaaa    720
ccggcggcgc tgggcgaggc gcaaccgacc aaaagcctgg aggaaaacaa gagcctgaaa    780
gaacagaaga aactgaacga cctgtgcttt ctgaagcgtc tgctgcaaga gatcaagacc    840
tgctggaaca aaattctgat gggcaccaaa gaacacgag                           879
```

```
<210> SEQ ID NO 170
<211> LENGTH: 7
<212> TYPE: PRT
<213> ORGANISM: Artificial Sequence
<220> FEATURE:
<223> OTHER INFORMATION: synthetic

<400> SEQUENCE: 170

Gly Ser Ile Phe Thr Ile Asn
1               5

<210> SEQ ID NO 171
<211> LENGTH: 8
<212> TYPE: PRT
<213> ORGANISM: Artificial Sequence
<220> FEATURE:
<223> OTHER INFORMATION: synthetic

<400> SEQUENCE: 171

Ile Thr Ser Gly Gly Ser Thr Asn
1               5

<210> SEQ ID NO 172
<211> LENGTH: 11
<212> TYPE: PRT
<213> ORGANISM: Artificial Sequence
<220> FEATURE:
<223> OTHER INFORMATION: synthetic

<400> SEQUENCE: 172

Val Val Val Thr Thr Thr Pro Tyr Ser Asp Tyr
1               5                   10

<210> SEQ ID NO 173
<211> LENGTH: 7
<212> TYPE: PRT
<213> ORGANISM: Artificial Sequence
<220> FEATURE:
<223> OTHER INFORMATION: synthetic

<400> SEQUENCE: 173

Ala Arg Ile Phe Ser Ser Tyr
1               5

<210> SEQ ID NO 174
<211> LENGTH: 8
<212> TYPE: PRT
<213> ORGANISM: Artificial Sequence
<220> FEATURE:
<223> OTHER INFORMATION: synthetic
```

<400> SEQUENCE: 174

Val Asn Gly Gly Ser Ser Ser Thr
1               5

<210> SEQ ID NO 175
<211> LENGTH: 15
<212> TYPE: PRT
<213> ORGANISM: Artificial Sequence
<220> FEATURE:
<223> OTHER INFORMATION: synthetic

<400> SEQUENCE: 175

Ala Gly Arg Ala Gly Pro Leu Ala Ala Ser Tyr Arg Tyr Asp Tyr
1               5                   10                  15

<210> SEQ ID NO 176
<211> LENGTH: 8
<212> TYPE: PRT
<213> ORGANISM: Artificial Sequence
<220> FEATURE:
<223> OTHER INFORMATION: synthetic

<400> SEQUENCE: 176

Ile Thr Arg Gly Gly Ser Thr Asn
1               5

<210> SEQ ID NO 177
<211> LENGTH: 11
<212> TYPE: PRT
<213> ORGANISM: Artificial Sequence
<220> FEATURE:
<223> OTHER INFORMATION: synthetic

<400> SEQUENCE: 177

Val Val Val Thr Thr Thr Ala Tyr Ser Asp Tyr
1               5                   10

<210> SEQ ID NO 178
<211> LENGTH: 8
<212> TYPE: PRT
<213> ORGANISM: Artificial Sequence
<220> FEATURE:
<223> OTHER INFORMATION: synthetic

<400> SEQUENCE: 178

Leu Thr Ser Gly Gly Ser Thr Asn
1               5

<210> SEQ ID NO 179
<211> LENGTH: 11
<212> TYPE: PRT
<213> ORGANISM: Artificial Sequence
<220> FEATURE:
<223> OTHER INFORMATION: synthetic

<400> SEQUENCE: 179

Val Val Val Thr Thr Thr Pro Tyr Ala Asp Tyr
1               5                   10

<210> SEQ ID NO 180
<211> LENGTH: 10
<212> TYPE: PRT
<213> ORGANISM: Artificial Sequence
<220> FEATURE:
<223> OTHER INFORMATION: synthetic

```
<400> SEQUENCE: 180

Val Val Val Thr Thr Pro Tyr Ser Asp Tyr
1               5                   10

<210> SEQ ID NO 181
<211> LENGTH: 7
<212> TYPE: PRT
<213> ORGANISM: Artificial Sequence
<220> FEATURE:
<223> OTHER INFORMATION: synthetic

<400> SEQUENCE: 181

Gly Ser Ile Cys Thr Ser Asn
1               5

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Gly Leu Thr Phe Ser Ile Arg
1               5

<210> SEQ ID NO 183
<211> LENGTH: 8
<212> TYPE: PRT
<213> ORGANISM: Artificial Sequence
<220> FEATURE:
<223> OTHER INFORMATION: synthetic

<400> SEQUENCE: 183

Ile Met Trp Ser Gly Gly Ala Thr
1               5

<210> SEQ ID NO 184
<211> LENGTH: 6
<212> TYPE: PRT
<213> ORGANISM: Artificial Sequence
<220> FEATURE:
<223> OTHER INFORMATION: synthetic

<400> SEQUENCE: 184

Trp Lys His Leu His Tyr
1               5

<210> SEQ ID NO 185
<211> LENGTH: 7
<212> TYPE: PRT
<213> ORGANISM: Artificial Sequence
<220> FEATURE:
<223> OTHER INFORMATION: synthetic

<400> SEQUENCE: 185

Val Ser Ile Phe Thr Ile Asn
1               5

<210> SEQ ID NO 186
<211> LENGTH: 8
<212> TYPE: PRT
<213> ORGANISM: Artificial Sequence
<220> FEATURE:
<223> OTHER INFORMATION: synthetic

<400> SEQUENCE: 186
```

Asn Thr Ser Gly Gly Ser Thr Asn
1               5

<210> SEQ ID NO 187
<211> LENGTH: 7
<212> TYPE: PRT
<213> ORGANISM: Artificial Sequence
<220> FEATURE:
<223> OTHER INFORMATION: synthetic

<400> SEQUENCE: 187

Gly Ser Leu Phe Thr Ile Asn
1               5

<210> SEQ ID NO 188
<211> LENGTH: 11
<212> TYPE: PRT
<213> ORGANISM: Artificial Sequence
<220> FEATURE:
<223> OTHER INFORMATION: synthetic

<400> SEQUENCE: 188

Leu Val Val Pro Pro Thr Pro Tyr Ser Val Tyr
1               5                   10

<210> SEQ ID NO 189
<211> LENGTH: 8
<212> TYPE: PRT
<213> ORGANISM: Artificial Sequence
<220> FEATURE:
<223> OTHER INFORMATION: synthetic

<400> SEQUENCE: 189

Ser Thr Ser Gly Gly Ser Pro Asn
1               5

<210> SEQ ID NO 190
<211> LENGTH: 11
<212> TYPE: PRT
<213> ORGANISM: Artificial Sequence
<220> FEATURE:
<223> OTHER INFORMATION: synthetic

<400> SEQUENCE: 190

Gly Gly Gly Ser Ser Thr Pro Asp Ser Asp Tyr
1               5                   10

<210> SEQ ID NO 191
<211> LENGTH: 7
<212> TYPE: PRT
<213> ORGANISM: Artificial Sequence
<220> FEATURE:
<223> OTHER INFORMATION: synthetic

<400> SEQUENCE: 191

Gly Ser Ile Phe Thr Ser Asn
1               5

<210> SEQ ID NO 192
<211> LENGTH: 11
<212> TYPE: PRT
<213> ORGANISM: Artificial Sequence
<220> FEATURE:
<223> OTHER INFORMATION: synthetic

<400> SEQUENCE: 192

-continued

Val Val Val Thr Thr Thr Pro Glu Ala Asp Tyr
1               5                   10

<210> SEQ ID NO 193
<211> LENGTH: 11
<212> TYPE: PRT
<213> ORGANISM: Artificial Sequence
<220> FEATURE:
<223> OTHER INFORMATION: synthetic

<400> SEQUENCE: 193

Val Val Val Thr Thr Thr Gln Tyr Ser Asp Tyr
1               5                   10

<210> SEQ ID NO 194
<211> LENGTH: 7
<212> TYPE: PRT
<213> ORGANISM: Artificial Sequence
<220> FEATURE:
<223> OTHER INFORMATION: synthetic

<400> SEQUENCE: 194

Gly Arg Thr Phe Ser Asn Tyr
1               5

<210> SEQ ID NO 195
<211> LENGTH: 9
<212> TYPE: PRT
<213> ORGANISM: Artificial Sequence
<220> FEATURE:
<223> OTHER INFORMATION: synthetic

<400> SEQUENCE: 195

Ile Ser Gln Ser Gly Ser Ile Thr Tyr
1               5

<210> SEQ ID NO 196
<211> LENGTH: 14
<212> TYPE: PRT
<213> ORGANISM: Artificial Sequence
<220> FEATURE:
<223> OTHER INFORMATION: synthetic

<400> SEQUENCE: 196

Gly Asn Ser Phe Lys Ser Asn Asp His Trp Ala Ser Thr Tyr
1               5                   10

<210> SEQ ID NO 197
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: X=any amino acid

<400> SEQUENCE: 197

Phe Gly Xaa Gly
1

<210> SEQ ID NO 198
<211> LENGTH: 4
<212> TYPE: PRT
<213> ORGANISM: Artificial sequence
<220> FEATURE:
<223> OTHER INFORMATION: synthetic

```
<220> FEATURE:
<221> NAME/KEY: Xaa
<222> LOCATION: (2)..(4)
<223> OTHER INFORMATION: X=any amino acid

<400> SEQUENCE: 198

Cys Xaa Xaa Xaa
1

<210> SEQ ID NO 199
<211> LENGTH: 5
<212> TYPE: PRT
<213> ORGANISM: Artificial sequence
<220> FEATURE:
<223> OTHER INFORMATION: synthetic

<400> SEQUENCE: 199

Leu Glu Trp Ile Gly
1               5

<210> SEQ ID NO 200
<211> LENGTH: 12
<212> TYPE: PRT
<213> ORGANISM: Artificial sequence
<220> FEATURE:
<223> OTHER INFORMATION: synthetic

<400> SEQUENCE: 200

Lys Arg Leu Ile Val Phe Thr Ala Thr Ser Ile Ala
1               5                   10

<210> SEQ ID NO 201
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: X=any amino acid

<400> SEQUENCE: 201

Trp Gly Xaa Gly
1
```